United States Patent [19]

Alyfuku et al.

[11] Patent Number: 5,410,471
[45] Date of Patent: Apr. 25, 1995

[54] NETWORKED HEALTH CARE AND MONITORING SYSTEM

[75] Inventors: Kiyoshi Alyfuku; Yoshiki Hiruta, both of Kanagawa, Japan

[73] Assignee: Toto, Ltd., Fukuoka, Japan

[21] Appl. No.: 16,366

[22] Filed: Feb. 11, 1993

[30] Foreign Application Priority Data

Feb. 24, 1992 [JP] Japan ................................. 4-072895

[51] Int. Cl.$^6$ ........................................... G06F 15/00
[52] U.S. Cl. ........................... 364/413.02; 364/413.04; 364/413.06; 4/314; 4/420; 4/661; 128/766; 128/708; 128/709; 128/736
[58] Field of Search .............. 364/413.02, 413.04, 364/413.06; 436/56; 4/314, 420, 661; 128/760, 771, 25 R, 32, 33, 707

[56] References Cited

U.S. PATENT DOCUMENTS

| | | |
|---|---|---|
| 4,962,550 | 10/1990 | Ikenaga et al. |
| 5,039,616 | 8/1991 | Copelan .......................... 436/56 |
| 5,241,958 | 9/1993 | Noeidner ......................... 607/87 |

FOREIGN PATENT DOCUMENTS

| | | |
|---|---|---|
| 0278631A1 | 1/1988 | European Pat. Off. |
| 292311A | 11/1988 | European Pat. Off. |
| 0323901A1 | 1/1989 | European Pat. Off. |
| 9103737 U | of 1991 | Germany |
| 2-54031 | 2/1990 | Japan |
| 2-116351 | 5/1990 | Japan |
| 2-140875 | 5/1990 | Japan |
| 2-164336 | 6/1990 | Japan |
| 2-299632 | 12/1990 | Japan |
| 2187554 | 9/1987 | United Kingdom |
| WO91/05311 | 4/1991 | WIPO |

OTHER PUBLICATIONS

S. Sawai et al "Estimation of Body Fat by Near Infrared Spectroscopic Technique" Japanese Phys. Fitness Sports, Med, 1990 39:155-163.

*Primary Examiner*—Robert A. Weinhardt
*Assistant Examiner*—Frantzy Poinvil
*Attorney, Agent, or Firm*—Lowe, Price, LeBlanc & Becker

[57] ABSTRACT

A networked health care and monitoring system (10) capable of providing an updated reliable vital information on the health condition of individuals and adapted to support home health care and maintenance. The system includes testing and measuring instruments (39; 43; 46; 49; 56) associated with certain household appliances such as a toilet system (12) and adapted to monitor the vital information passively in response to the use thereof in connection with routine living activities of the individuals. The system may further include control devices (39; 46; 49; 56) associated with certain household appliances, such as an ergometer (15), having health care and maintenance functions and adapted to control the appliances based on the vital information monitored by the testing and measuring instruments in the system. In one embodiment wherein the system is arranged in the centralized network configuration, the testing and measuring instruments and the control devices are connected via a local area network with a data controller (20) wherein all the vital information obtained in the system is stored. Instruments and devices (39; 43; 46; 49; 56) are permitted to access the controller through the network to retrieve necessary vital information therefrom. In another embodiment arranged in the distributed network configuration, the vital information obtained by respective measuring instruments is stored therein and is furnished upon request to the other appliances.

45 Claims, 54 Drawing Sheets

FIG. 3A

| I HOUSEHOLD APPLIANCES | II INHERENT FUNCTION | III ADDITIONAL VITAL INFO MEASURING FUNCTION | IV ADDITIONAL HEALTH-CARE FUNCTION | V PARAMETER OF RECOGNITION OF INDIVIDUALS | VI DATA TRANSMITTED FROM CONTROLLER |
|---|---|---|---|---|---|
| WC | EXCRETION | URINALYSIS ELECTROCARDIOGRAPHY BLOOD PRESS/ PULSE MSMNT BODY FAT MSMNT WEIGHT MSMNT | — | BODY WEIGHT | STATURE SEXUALITY |
| BED | SLEEPING | BASAL BODY TEMPERATURE MSMNT | — | STATURE | NONE |
| BATH | BATHING | MSMNT OF R-R INTERVAL OF ELECTROCARDIOGRAM | MASSAGING TEMPERATURE CONTROL | DISPLACEMENT | BODY FAT % BLOOD PRESSURE /PULSE RATE AMOUNT OF EXERCISE R-R INTERVAL |
| ERGOMETER | EXERCISE | BLOOD PRESS/ PULSE MSMNT AMOUNT OF EXERCISE WEIGHT MSMNT | CONTROL OF PROPER AMOUNT OF EXERCISE | BODY WEIGHT | BODY FAT % BLOOD PRESSURE /PULSE RATE BASAL BODY TEMPERATURE |
| EASY CHAIR | REST | ELECTROCARDIOGRAPHY BLOOD PRESS/ PULSE MSMNT WEIGHT MSMNT | MASSAGING | BODY WEIGHT | R-R INTERVAL |

FIG. 3B

| I HOUSEHOLD APPLIANCES | II INHERENT FUNCTION | III ADDITIONAL VITAL INFO MEASURING FUNCTION | IV ADDITIONAL HEALTH-CARE FUNCTION | V PARAMETER OF RECOGNITION OF INDIVIDUALS | VI DATA TRANSMITTED FROM CONTROLLER |
|---|---|---|---|---|---|
| MENU PROCESSOR | PRESENTATION OF MENU | — | HEALTH MAINTENANCE AND ALIMENTARY THERAPY OF DISEASE | — | URINALYSIS DATA AMOUNT OF EXERCISE BODY FAT % BODY WEIGHT |
| TELEPHONE | COMMUNICATION | — | TRANSMISSION OF VITAL INFORMATION | — | URINALYSIS DATA AMOUNT OF EXERCISE BODY FAT % BLOOD PRESSURE /PULSE RATE BASAL BODY TEMPERATURE R-R INTERVAL |
| MONITOR | DISPLAY | — | MONITORING OF HEALTH CONDITIONS AND EARLY DETECTION OF DISEASE | — | URINALYSIS DATA AMOUNT OF EXERCISE BODY FAT % BLOOD PRESSURE /PULSE RATE BASAL BODY TEMPERATURE R-R INTERVAL |

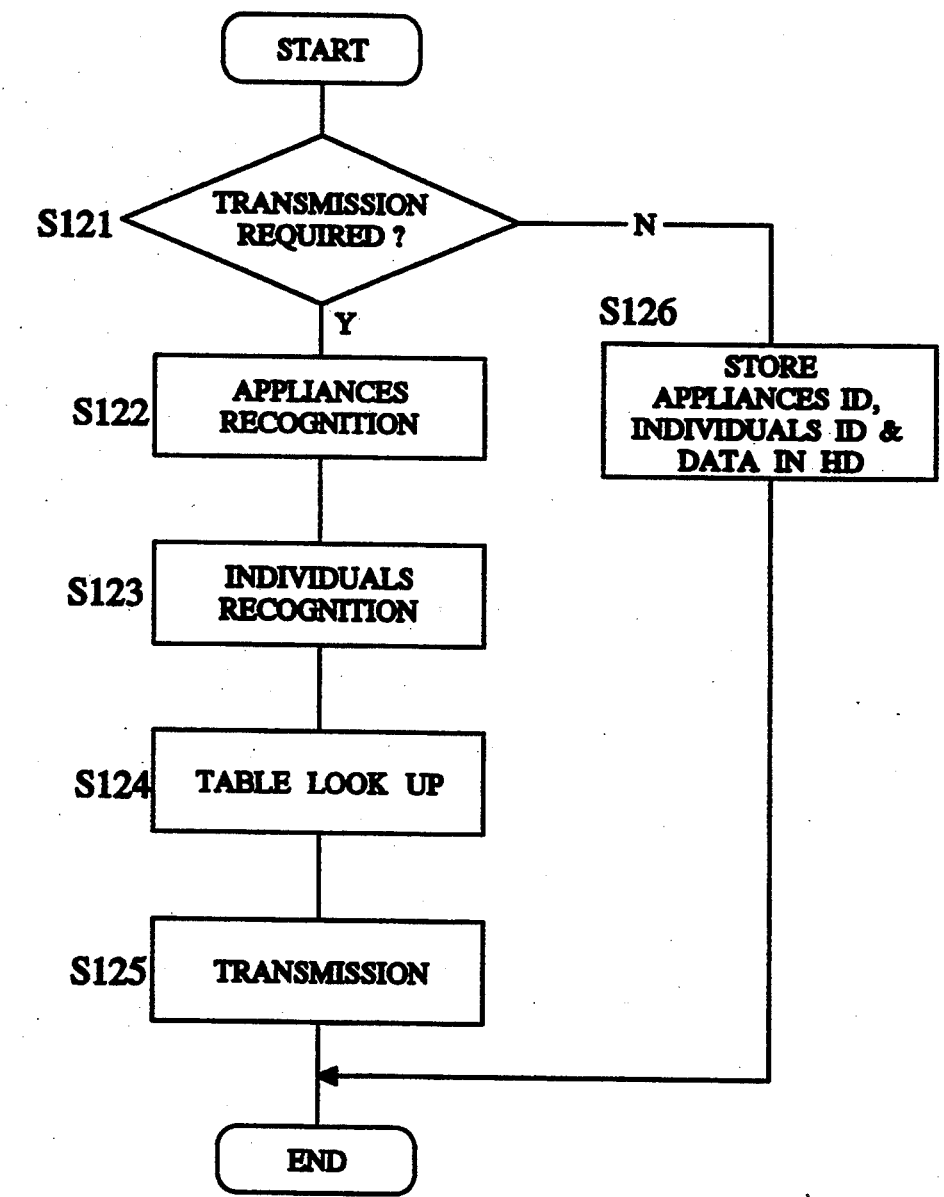

NETWORKED HEALTH CARE AND MONITORING SYSTEM

BACKGROUND OF THE INVENTION

1. Field of the Invention

The present invention relates to a health care and monitoring system which is capable of detecting and monitoring vital signs and information of individuals during the course of routine living activities of individuals taking place in routine living environments such as homes and offices and wherein the vital information thus obtained is used in connection with routine health care and maintenance activities of individuals for the purposes of health care and maintenance, including prophylactic medicine, early detection of diseases and continuation of therapy.

2. Description of the Prior Art

Due to recent trends for longevity, the importance of self health care and maintenance has been receiving increasing attention irrespective of age of people. Today, many people, elderly or young, not only periodically consult professional medical institutions such as hospitals and clinics for diagnostic and various professional advices helpful in prevention and early detection of diseases, but also are constantly rendering considerable effort by themselves to maintain their health by making use of non-medical health maintenance facilities such as gymnastic or sport clubs. Also, a variety of home health care and monitoring instruments, such as home sphygmomanometer and home urinal assay assemblies, are available to enable people's home health check in support of professional medical monitoring as well as to assist in continuation of home care.

Primarily, the vital information useful in health care and maintenance of individuals is monitored at professional medical institutions such as hospitals wherein various medical testing and measuring instruments are provided. In certain occasions, the vital signs and information detected thereby are forwarded through a local area network or telemetry to a host computer or work station of the hospital for centralized storage and processing, as described, for example, in Japanese Patent Kokai Publication Nos. 2-140875(1990); 2-116351(1990); 2-164336(1990); 2-299632(1990); and European Patent Publication No. 269,907 A1.

The medical services for testing and vital information monitoring at such professional institutions are generally available whenever required to inpatients who are under hospital care. Therefore, the inpatients have the benefit of increased chance of testing and monitoring and may thus be subjected to a continuous and updated care.

Outpatients, home care patients and those individuals who desire a periodical health check, however, must visit the hospital from time to time in order to have their health condition monitored. This will involve considerable economical burden and time loss. In the case of home care patients, in particular, a visit to hospital may often involve substantial physical and mental exhaustion. As a result, there is a tendency that people are discouraged from visiting hospitals adequately frequently whereby the occasions of sampling and monitoring of the vital data are limited to the minimum. This results in the disadvantage that it is difficult to obtain and accumulate the latest vital information due to failure of updating.

Another important problem associated with vital data monitoring at the professional institutions is related to the possible insufficiency or lack of reliability of obtained data. It has been experienced by skilled medical professionals that, during electrocardiography and measurement of the artery blood pressure, for example, a patient who has realized measurement is apt to be overly excited and becomes hypertonic so that the resulting data often exhibits unusual value. Accordingly, repeated measurements are often necessary until a reliable data is resulted.

It is known in the art to arrange a testing and measuring instrument within the residence of a patient and to transmit the obtained vital information to a host computer of professional medical care institutions via public telecommunication line as disclosed, for example, in Japanese Patent Kokai Publication Nos. 2-54031(1990); 2-279056(1990); 2-121627(1990); U.S. Pat. No. 4,962,550; and European Patent Publication No. 292,311 A2. For example, U.S. Pat. No. 4,962,550 assigned to the assignee of the present invention describes a home health monitoring system associated with a toilet system incorporating a built-in apparatus for urinalysis which is adapted to transmit the obtained urinalysis data to a remote computer. Home health monitoring device is also described in International Patent Publication No. WO 91/05311. This publication proposes a medication delivery system adapted to support home care of patients wherein a terminal equipment having a physical measuring device such as sphygmomanometer is provided in the home of a patient. In response to instructions from a central station, the patient wears and operates the sphygmomanometer to permit measurement of the artery blood pressure, the resulting data being in turn forwarded to the central station for professional decision and instructions on medication.

Advantageously, these household testing and measuring systems ensures monitoring of the latest daily health information because measurement at home may be carried out readily and more frequently. Furthermore, measurements may be performed under adequately relaxed conditions. However, the problem encountered with these household systems is that a series of testing and measuring procedures must be performed by the individuals by themselves on their own judgement and manipulation. In contrast to health monitoring conducted at hospitals wherein testing and measuring instruments are operated by a physician or nurse skilled in their manipulation and procedures, a patient or user of the household measuring system must be positively engaged in electronic dialogue with a computer of the measuring system by manipulating a man-machine interface such as a computer keyboard in order to cause the measuring system to successfully perform a predetermined program of testing and measurement. To perform automated urinalysis, for example, it is necessary for the user to manipulate the keyboard to select the program menu, to input his or her name, date and time of measurement and so on, and then to depress a start button at a proper timing. Such electronic dialogue by way of the man-machine interface is cumbersome even for ordinary person and is especially difficult to perform for elderly individuals who are encountering loss of memory, degradation in eyesight and decreasing muscle response.

Manipulation of the man-machine interface is also necessary to operate those household appliances which are used in homes for the purposes of health care and maintenance of individuals and which require a certain vital information for their intended operation. For example, an indoor exercise apparatus such as a bicycle-simulated ergometer requires that various parameters including the stature, body weight, age, sexuality, body fat content and desired amount of exercise of the user be input through an input device. Similarly, for measurement of the body fat content, it is desirable to input a vital data on the stature, body weight, age, sexuality and the amount of daily exercise. A conventional computerized menu processor adapted to provide alimentary menu requires input of vital information on the body weight, the results of urinalysis, the amount of exercise, etc. As information input operation of all these data must be performed by the manipulation of the man-machine interface such as a keyboard device, it has been cumbersome to set up the health care and maintenance appliances.

BRIEF SUMMARY OF THE INVENTION

Accordingly, an object of the present invention is to provide a networked vital information monitoring system which is capable of detecting and monitoring vital signs passively in response to routine living activities of individuals thereby to provide updated latest vital information.

Another object of the invention is to provide a networked vital information monitoring system which is capable of detecting and measuring vital signs during the course of day-to-day living activities of individuals without causing the individuals to realize measurement, thereby to provide a reliable vital information.

A still another object of the invention is to provide a networked vital information monitoring system which is user-friendly even for those individuals such as elderly people who have difficulties in manipulating a man-machine interface and wherein vital information is detected and monitored passively in response to routine living activities of individuals without requiring positive intervention on the part of the individuals.

A further object of the invention is to provide a health monitoring system which is adapted to monitor vital signs of individuals in connection with their day-to-day physiological activities and which is capable of providing a compiled updated vital information which is reliable and is suitable to be brought to professional medical institutions for analysis by medical professionals.

Another object of the invention is to provide a networked health care and monitoring system which is adapted to monitor vital signs of individuals in their routine living environments such as homes and offices and which is capable of providing a compiled vital information which, in combination with advices of medical professionals, is useful in supporting home health care and maintenance for the purposes of prevention and early detection of diseases and continuation of therapy.

Another object of the invention is to provide a networked health care and monitoring system which is adapted to monitor vital information on individuals in connection with their routine living activities and wherein the vital information thus obtained is used in connection with day-to-day health care and maintenance activities of individuals.

The networked health care and monitoring system according to the present invention is designed to detect and monitor vital signs and information of individuals in routine or day-to-day living environments, such as homes and offices, passively in response to their routine living activities such as excretion, bathing, sleeping, resting and indoor exercise. To this end, various testing and measuring instruments are arranged as associated with various household appliances so as to passively detect the vital signs and features of the individuals in response to the use of the household appliances thereby to derive the vital information on the individuals. The term "household appliances" as used in the following description and the appended claims is intended to mean those apparatus and devices which are arranged in a building, including residence and office, for use in ordinary living activities of individuals such as excretion, bathing, sleeping, resting, indoor exercise and ingestion. Typically, the household appliances with which various testing and measuring instruments are associated may include water closet system, bed and bath system. For example, the water closet system may be provided with a measuring device for detecting the body weight, an assay apparatus for performing urinalysis, an electrocardiograph, a sphygmomanometer for measuring an artery blood pressure and pulse rate, and a non-destructive measuring instrument for detecting the body fat content. Similarly, the bed may be provided with a measuring system for detecting the basal body temperature of the user. The bath system may incorporate an electrocardiograph which is adapted to detect the degree of mental stress of the bather.

As the household appliances such as water closet and bed are used at least once everyday during regular course of living activities of the individuals and because the testing and measuring instruments is associated with the household appliances so as to sample and monitor the vital data each time the household appliances are used, the latest vital information updated on a daily basis is obtainable by the health care and monitoring system according to the invention.

The networked health care and monitoring system may further comprise various control devices associated with the household appliances in order to assist in the health care and maintenance activities of the individuals. These control devices are designed to control the health care and maintenance functions of the associated household appliances based on the vital information obtained by the testing and measuring instruments of the system. For example, a bicycle-simulated ergometer may be designed to control the conditions of exercise based on the body fat content detected by the testing and measuring instrument associated with the water closet system. Similarly, the bath system may be provided with a massaging function which is controlled in accordance with the degree of mental stress of the bather as detected by the electrocardiograph associated with the bath system.

As in this manner the health care and maintenance functions of the household appliances are controlled based on the latest vital information detected in the system, a high degree of health care is attainable.

In one embodiment of the invention, various testing and measuring instruments and control devices associated with the household appliances are networked in form of the so-called "centralized" communications network configuration so that the vital information obtained by respective testing and measuring instruments in the network is transmitted via a data communication medium arranged in the building to a data controller which is adapted to store in a data storage memory thereof the vital information for centralized storage and control of the vital information. The vital information once stored in the controller memory is furnished upon request to the testing and measuring instruments as well as to control devices associated with any of the household appliances in the network to enable the instruments and devices to perform their intended function.

In another embodiment, the testing and measuring instruments and control devices associated with the household appliances are networked in form of the "distributed" communications network configuration. In the distributed network topography, the vital information obtained by respective testing and measuring instruments in the network is stored in the storage memories of respective instruments. Those testing and measuring instruments and control devices which requires, for the purposes of performing their own function, the vital information stored in other instruments may access via the data communication medium such other instruments to retrieve therefrom the necessary vital information.

These features and advantages of the invention, as well as other features and advantages thereof, will become apparent from the following description made in conjunction with the preferred embodiments thereof with reference to the accompanying drawings.

BRIEF DESCRIPTION OF THE DRAWINGS

FIGS. 3A and 3B show a table indicating various functions of respective household appliances incorporated in the health care and monitoring system of the invention, with column II showing the conventional and inherent functions of various appliances, columns III and IV showing the additional functions thereof provided according to the invention, column V showing the parameter used for individuals recognition, column VI showing various data furnished by the data controller to permit respective appliances to perform the additional functions when the health care and monitoring system is networked in the centralized network configuration;

FIG. 7 is a flowchart showing the operation of the controller the centralized network configuration;

FIG. 8 illustrates an example of serial data transmission format used in data communication between the controller and the household appliances;

DESCRIPTION OF THE PREFERRED EMBODIMENTS

The present invention will now be described in more detail with reference to various embodiments thereof illustrated in the accompanying drawings.

Referring first to FIGS. 1-46, the health care and monitoring system, according to the invention, of the "centralized" communications network configuration will be described.

Figure 1:
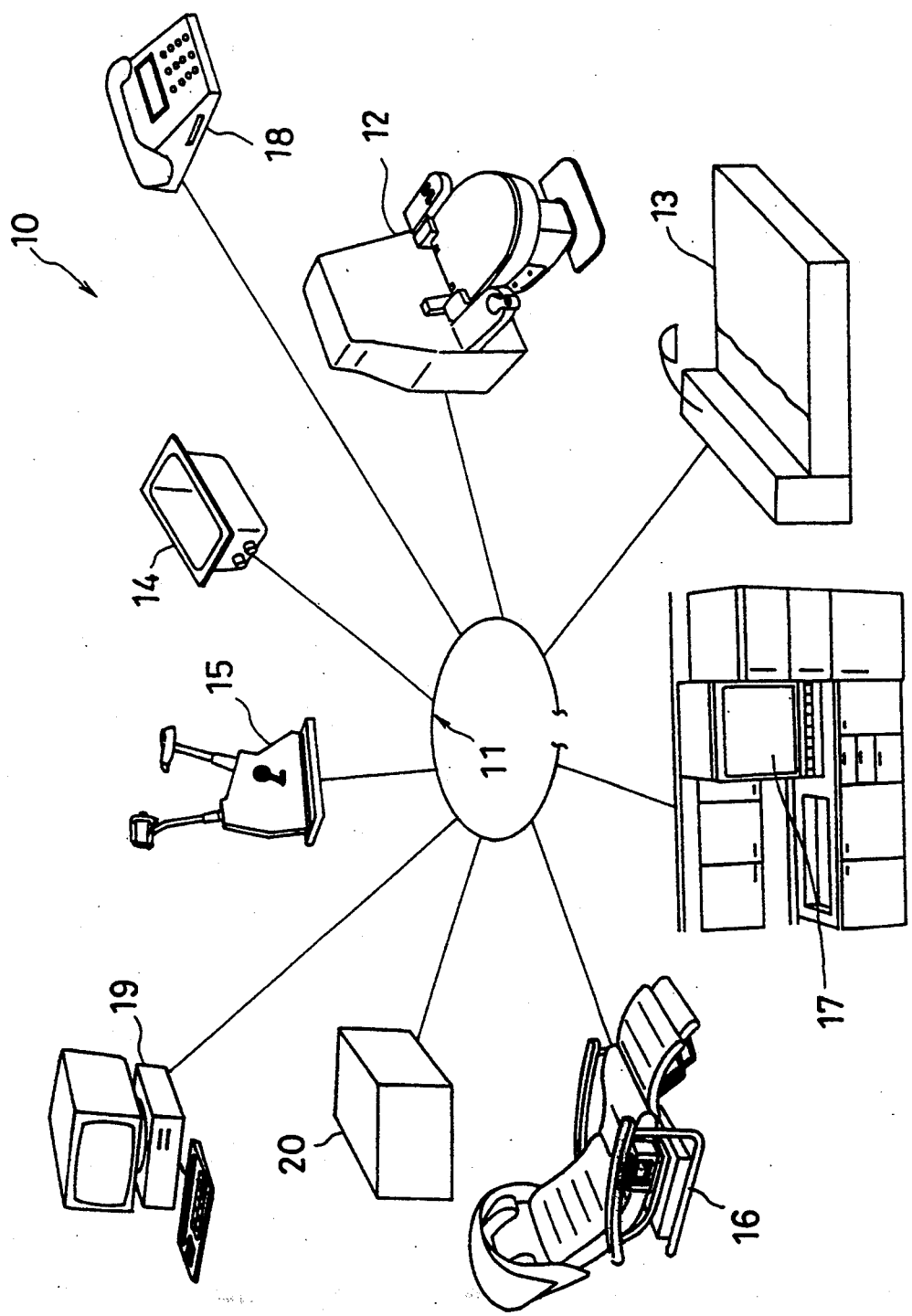
FIG. 1 is a schematic representation of the health care and monitoring system of the centralized network configuration according to invention.
Figure 2:
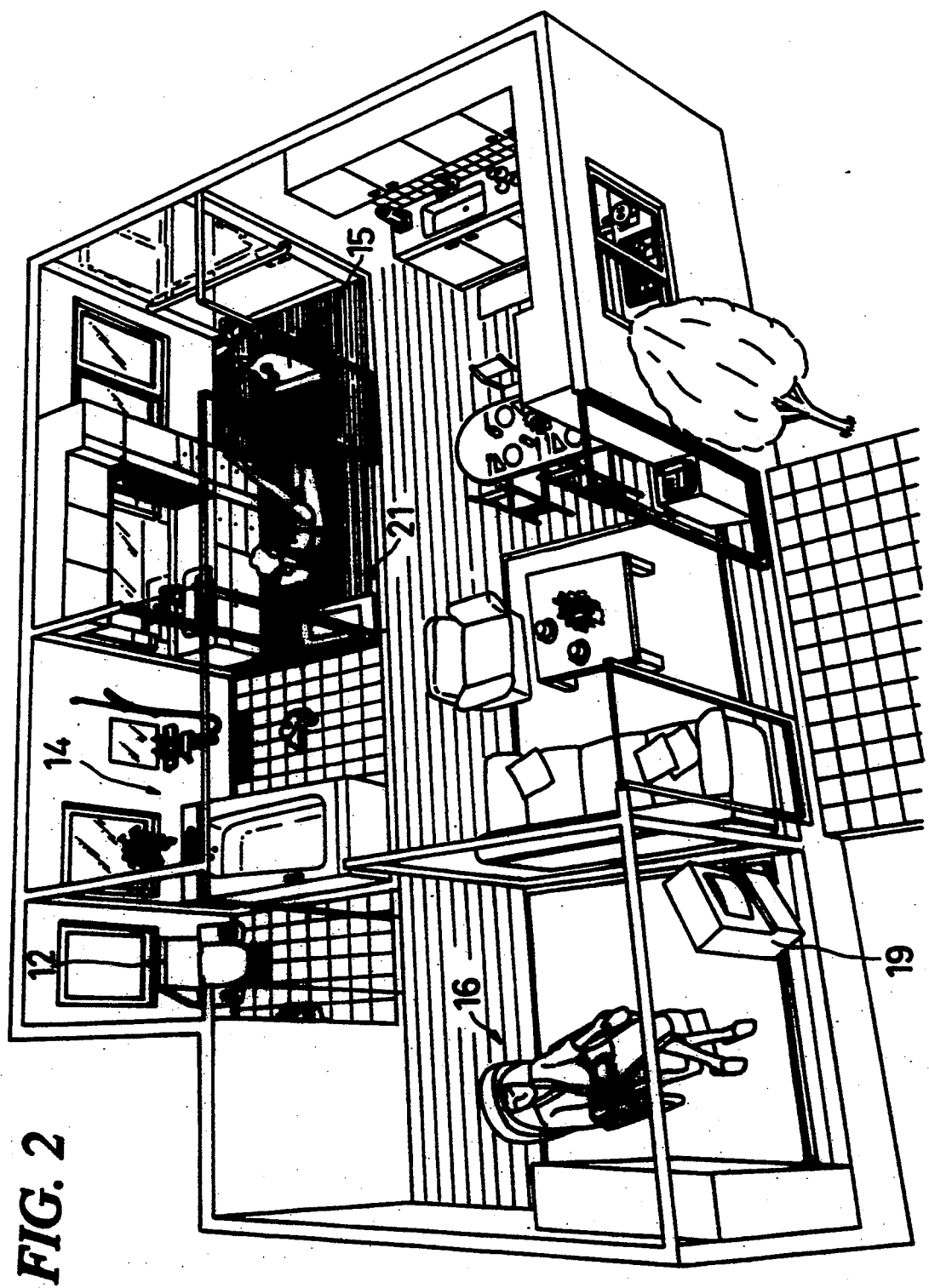
FIG. 2 is a perspective view showing part of a residence wherein the health care and monitoring system of FIG. 1 is provided.

FIGS. 1 and 2 illustrate the networked health care and monitoring system of the invention as arranged in a residence of individuals. As shown in FIG. 1, the networked health care and monitoring system 10 comprises a conventional data communication medium 11 in the form of coaxial or twist-pair cable which is arranged in the residence shown in part in FIG. 2. Various testing and measuring instruments and/or control devices associated respectively with a plurality of household appliances are connected to the data communication medium 11 in such a manner as to form a local area network (LAN).

In the illustrated embodiment, the household appliances may include a water closet facility 12, one or more beds 13, bathing installations 14, a bicycle-simulated ergometer 15, an easy chair 16, a computerized menu processor 17, a telephone 18 with modulator-demodulator (MODEM) and a video monitor 19. As indicated in columns I-IV of the table shown in FIGS. 3A and 3B, these household appliances are provided, in addition to their inherent functions associated with routine living activities of the individuals, with various additional functions of monitoring and deriving vital information representing the health conditions of the individuals and/or additional health care functions to support and assist in health care of the individuals. To this end, various testing and measuring instruments as well as control devices are operatively associated with respective household appliances according to the nature of the appliances.

More specifically, the water closet system 12, which inherently is intended for use in excretion, is additionally provided with vital information measuring and monitoring functions which include an automated urinalysis apparatus for sampling and analyzing urine released from the user thereof, an electrocardiograph for detecting and recording the electrocardiogram while the individual is sitting on the toilet stool, an instrument for the measurement of the artery blood pressure and pulse rate, a non-destructive testing and measuring instrument for detecting the body fat percentage of the user, and a weight detector for measuring the body weight of the individual. Similarly, the bed 13 is generally used during sleep but incorporates as the additional vital information measuring function thereof a built-in device for measuring the body temperature of the user to derive the basal body temperature. The bath system 14 is originally intended for bathing purposes but is provided in its turn with a built-in electrocardiograph for measuring and detecting during bathing the R—R interval of electrocardiogram, described later, in order to determine the degree of mental stress of the individuals. The bath system 14 further incorporates additional health care functions including arrangements for providing the bather with massaging effect and for controlling the bath temperature as described later in more detail. The ergometer 15 is a loaded in-door training equipment simulating a bicycle and is primarily intended for use in in-door exercise for the purposes of health maintenance. The ergometer 15 is designed to provide the additional vital information deriving functions of measuring the blood pressure and pulse rate, the amount of exercise and the body weight of the exerciser and is further designed to control the imposed load during exercise in accordance with the vital information so as to provide the health care function of sustaining the proper amount of exercise. The easy chair 16 is provided as the additional vital information measuring functions thereof with an electrocardiograph, a sphygmomanometer for measuring the artery blood pressure and pulse rate and a body weight detector, and is further provided as the additional health care function with a built-in vibratory massaging mechanism. The menu processor 17 is comprised of a general purpose personal computer having a data base compiling a variety of menu and is programmed to advise and formulate proper menu suitable for the health care and alimentary therapy of the individuals according to the vital information concerning the health conditions of respective individuals. The telephone 18 with MODEM may be used to transmit the vital information obtained in the networked health care system 10 via public telecommunications lines toward host computers of professional medical institutions or computerized monitoring centers. The video monitor 19 comprises a personal computer with a video display device and may be used to visually check the vital information so as to monitor the health conditions of the members of the family for early detection of diseases, if any.

Connected further to the data communication medium 11 is a data controller 20 having an electronic data storage memory. In the "centralized" network topography shown in FIG. 1, the function of the data controller 20 is to provide a centralized storage and control of the vital information acquired by respective testing and measuring devices associated with the household appliances in the network and to furnish the testing and measuring devices as well as the control devices of various household appliances with any vital information required for their intended operation. For example, as listed in column VI 35 of the table of FIGS. 3A and 3B, the controller 20 provides those household appliances having the health care functions, such as the bath system 14, the ergometer 15, the easy chair 16, the menu processor 17 and the monitor 19, with the vital data necessary for their operation, as described later in a greater detail. Also, the controller 20 furnishes the body fat measuring instrument of the toilet system 12 with an information necessary for the computation of body fat percentage.

FIG. 2 schematically illustrates part of the residence provided with the health care and health monitoring network system 10 according to the invention. As shown, the water closet 12 and the bath system 14 are disposed in the residence, with an electric bathroom scale 21 for detecting the body weight of the bather being positioned at the entrance to the bath room, the bicycle-simulated ergometer 15 being arranged in a health room. A person seated on the easy chair 16 in a living room is relaxed and looks into the video monitor 19 to check the health conditions of the members of his family.

Figure 4:
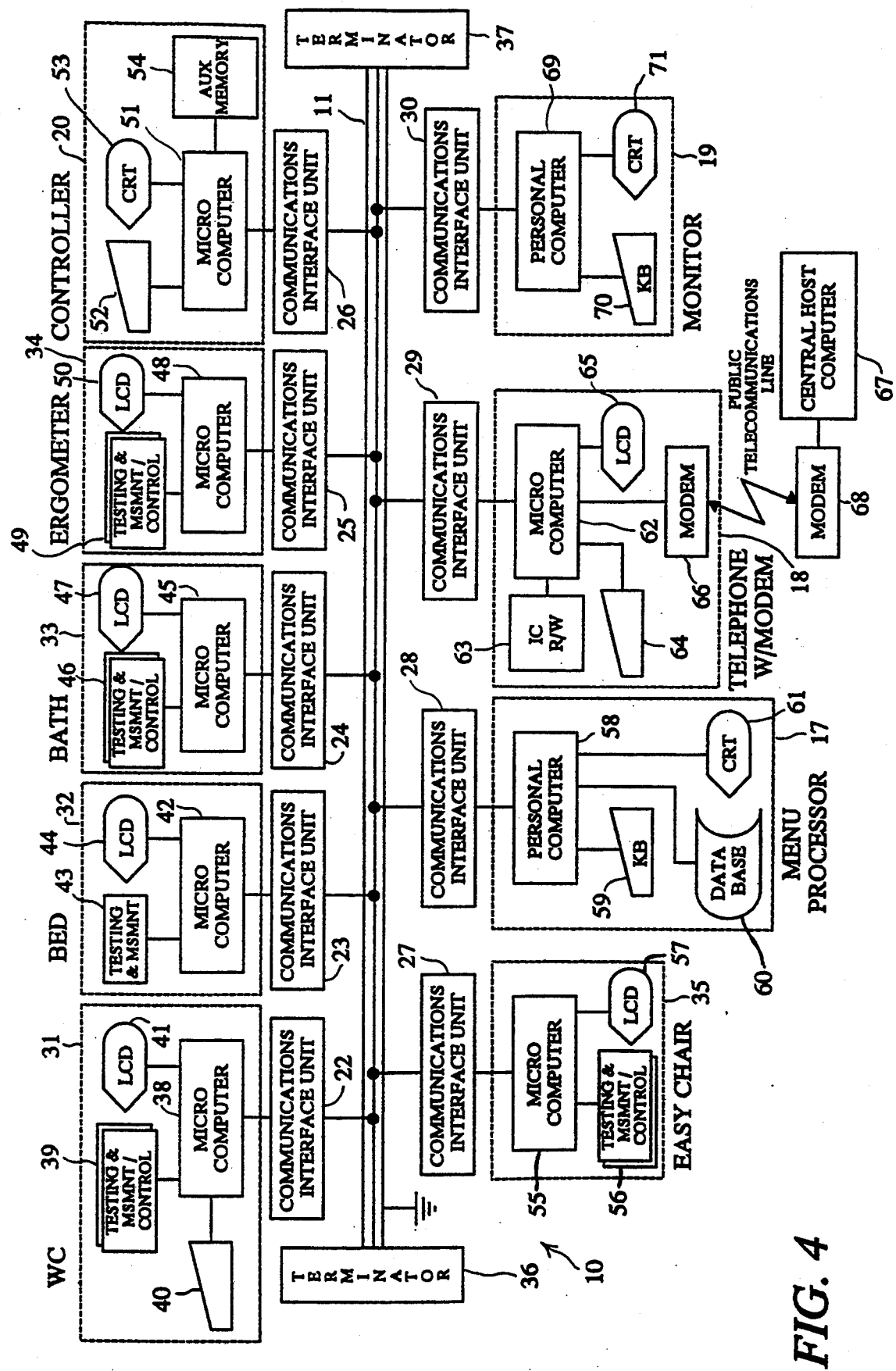
FIG. 4 is a block diagram of the health care and monitoring system of the centralized network configuration shown in FIG. 1.

Referring to FIG. 4 wherein the block diagram of the networked health care system 10 is shown, various testing and measuring devices and/or control devices associated with respective household appliances 12–19 are arranged to communicate via the coaxial cable 11 with the controller 20 to transmit and receive the vital information. More specifically, the coaxial cable 11 is connected via communications interface units 22–30 and the conventional T-connectors (not shown) with a measuring and control system 31 associated with the water closet system 12, a testing and measuring system 32 associated with the bed 13, a measuring and control system 33 associated with the bathing facility 14, a measuring and control system 34 associated with the ergometer 15, the controller 20, a measuring and control system 35 associated with the easy chair 16, the menu processor 17, the telephone 18 with MODEM, and the monitor 19, respectively. A pair of terminators 36 and 37 are disposed at the ends of the coaxial cable 11 as well known in the art. Although in the illustrated embodiment the network is arranged in the "bus" topography, a network configuration of the "star" or "ring" type may be used as will be apparent for those skilled in the art.

The measuring and control system 31 of the toilet facility 12 comprises a microcomputer 38 which is operatively connected to a series of measuring and control devices 39 for performing urinalysis, electrocardiography, sphygmomanometry including pulse rate measurement, body fat percentage measurement and body weight measurement, respectively, as well as to an input device 40 and a liquid crystal display device (LCD) 41. The measuring system 32 of the bed 13 includes a microcomputer 42, a measuring instrument 43 for detecting the body temperature and an LCD 44. The measuring and control system 33 of the bath system 14 comprises a microcomputer 45 which is connected to a series of measuring and control devices 46 and an LCD 47. The measuring and control system 34 for the ergometer 15 comprises a microcomputer 48 which is connected to a series of measuring and control devices 49 for performing sphygmomanometry and pulse rate measurement, body weight measurement and load control, respectively, as well as to an LCD 50. The controller 20 is comprised of a microcomputer 51, a keyboard 52, a cathode ray tube (CRT) 53 and an auxiliary memory device 54 such as hard-disc drive. The measuring and control system 35 of the easy chair 16 comprises a microcomputer 55 which is connected to a series of measuring and control devices 56 for performing electrocardiography, sphygmomanometry and body weight measurement, respectively, and to an LCD 57. The menu processor 17 consists of a general purpose personal computer 58 connected to a keyboard 59, a data base 60 stored in a hard-disc drive, and a CRT 61. The telephone 18 is provided with a microcomputer 62, an IC card read and write device 63, an input device 64, an LCD 65 and a MODEM 66 which communicates via public telecommunications lines with a MODEM 68 of a host computer 67 installed in hospital, medical clinic, centralized health monitoring institution, or life-care Center. The video monitor 19 may include a general purpose personal computer 69, a keyboard 70 and a CRT 71.

Figure 5:
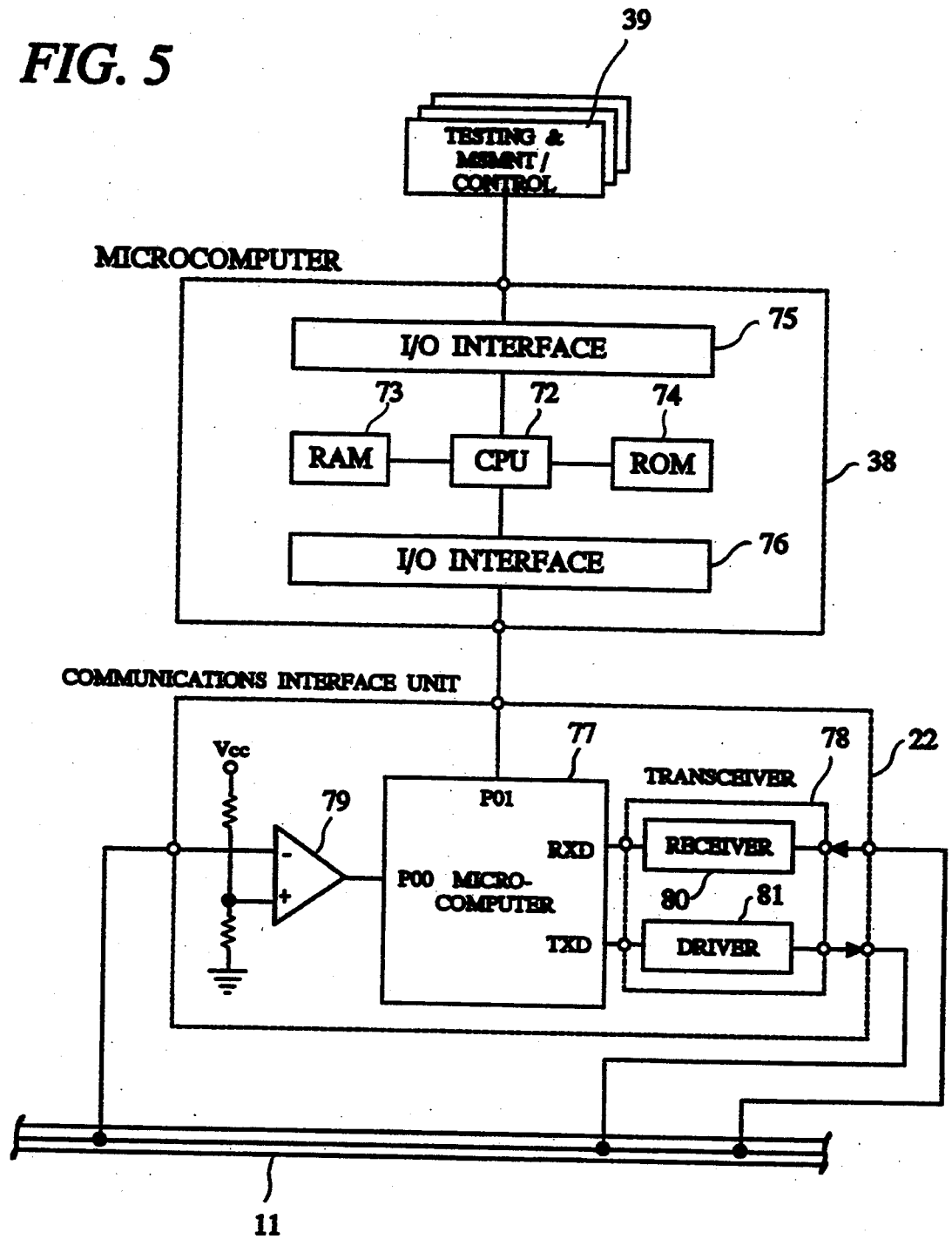
FIG. 5 is a block diagram showing examples of a microcomputer and a communications interface unit associated with a water closet system of the health care and monitoring system of the centralized network configuration according to the invention, it being understood that microcomputers and interface units associated with the controller and the other household appliances except for menu processor and video monitor may have similar arrangement.

As shown in FIG. 5, the microcomputer 38 associated with the water closet system 12 includes a central processing unit (CPU) 72, a random access memory (RAM) 73, a read-only memory (ROM) 74 for storing program and other data, and input and output interfaces 75 and 76. A suitable example of the microcomputer 38 is the single-chip 8-bit microcomputer M37450 marketed by Mitsubishi Electric Corporation, Tokyo, Japan. Other microcomputers 42, 45, 48, 51, 55 and 62 may similarly consist of the M37450 mentioned.

As described later in a greater detail, the vital information measuring and monitoring devices associated with several of the household appliances of the networked system 10 are adapted to respond to the use by the individual of a particular household appliance (1) to passively and automatically detect at least one physical characteristic of the individual, as shown in column V of the table of FIG. 3, thereby to derive physical data required for the recognition of the particular individual, (2) to passively and automatically detect at least one physiological characteristic of the individual, as shown in column 3 of the table of FIG. 3, thereby to derive the vital data representing the health condition of that individual, and (3) to cause these data to be transmitted to the coaxial cable 11. In response to such transmission of data, the controller 20 recognizes the particular individual based on the individuals recognition data and stores in its memory 54 the vital information in connection with that particular individual.

For example, when the toilet system 12 is used for urination, the measurement and control system 31 thereof passively detects the body weight of the user and transmits signals representing the detected weight value through the communications interface unit 22 onto the coaxial cable 11. The signals transmitted on the cable 11 are received by the controller 20 via the communications interface unit 26. Upon receipt of the signals representing the weight of the user from the measuring and control system 31 of the toilet system 12, the controller 20 looks into the memory 54 wherein the weight values may preliminarily be stored for all the members of the family by inputting from the keyboard 52. The controller 20 then compares the retrieved data with the weight value transmitted from the measuring and control system 31 of the toilet system 12 so as to recognize and identify the particular user and thereafter transmits back to the measuring and control system 31 of the toilet system 12 signals representing the identification number (ID) of the particular user. As urination is detected thereafter, urinalysis is automatically performed and the resulting urinalysis data is transmitted to the controller 20 for storage in the memory 54. When urination is conducted with the user seated on the toilet stool, measurement and recording of the electrocardiogram as well as measurement of the body fat content are further carried out automatically as described later and the resulting data are transferred to the controller 20 and stored in the memory 54 in connection with the particular individual.

As the bed 13 is used, the testing and measuring system 32 associated therewith passively detects the stature and the body temperature of the user and transmits the obtained data via the interface unit 23 onto the cable 11. With the stature values for all the family members being preliminarily stored in the memory 54, the controller 20 similarly recognizes and identifies the particular user according to the transmitted stature data and causes the body temperature data to be stored in the memory 54 in connection with the particular user.

Similarly, when the bath system 14 is used, the measurement and control system 33 thereof passively detects the displacement or volume of the user as well as the R—R interval of electrocardiogram described later and sends the resulting data via the interface unit 24 to the data communication medium 11. As the data relative to the displacement may similarly be stored in the memory 54 for all the members of the family, the controller 20 recognizes and identifies in a similar manner the particular user based on the displacement data transmitted and operates to store in the memory 54 the obtained data on the R—R interval of electrocardiogram in conjunction with the particular individual.

With regard to the easy chair 16, the parameter used for the recognition and identification of the individuals is the body weight. The measurement and control system 35 of the easy chair 16 responds to the use thereof and passively detects and monitors the weight and the electrocardiogram of the user to cause the resulting data to be transmitted through the interface unit 27 to the coaxial cable 11.

Further, the vital information measuring and monitoring devices associated with a certain household appliances of the networked system 10 are designed to commence acquisition of the vital information only after positive intervention by the user but are also adapted to passively acquire the physical data required for the recognition and identification of the individuals. In the water closet system 12, the ergometer 15 and the easy chair 16, for example, the artery blood pressure and pulse rate can be monitored only when the user has positively worn a measuring finger cuff on his or her finger, the detected data being transferred to the controller 20 along with the individual recognition parameter.

Furthermore, as described later in more detail, the control devices associated with a certain household appliances of the system 10 are adapted to control or operate those household appliances by acquiring from the controller 20 the vital information concerning the particular user of the appliances. For example, the menu processor 17 advises menu for a particular individual by receiving from the controller 20 the data of urinalysis, the data on the amount of exercise derived by the ergometer 15, the data on the body fat percentage, and the body weight data, concerning that particular individual. The vital information to be transmitted from the controller 20 for these purposes are listed in column VI of the table shown in FIG. 3.

To perform transmission and reception of the foregoing data, the communications interface units 22–30, which is also known as communications control units, are designed to carry out data communications between the coaxial cable 11 and the corresponding microcomputers 38, 42, 45, 48, 51, 55 and 62 as well as the corresponding personal computers 58 and 69, in accordance with a predetermined program and communications protocol, the program being described later in a greater detail with reference mainly to FIGS. 6-8. As the communications interface units 22–30 may all be identical in the hardware and software architecture, only the interface unit 22 will be described. As shown in FIG. 5, the interface unit 22 includes a microcomputer 77, a transceiver 78 and a comparator 79. Similar to the microcomputer 38 of the measurement and control system, the microcomputer 77 of the interface unit may comprise the single-chip 8-bit microcomputer M37450 mentioned hereinbefore. The M37450 microcomputer is provided with the universal asynchronous receiver transmitter (UART) according to the interface standard RS-232C developed by the Electronic Industries Association (EAI) and is suitable to perform data communications with the coaxial cable 11 in an asynchronous manner. To avoid collision that would otherwise occur when two or more of the interface units 22–30 simultaneously transmit signals to the cable 11, the interface unit 22 is designed to transmit data only when the cable 11 is not busy. To this end, the line potential of the coaxial cable 11 is applied to the minus input terminal of the comparator 79, to the plus input terminal of which is applied a reference voltage, the output of the comparator 79 being applied to the P$\emptyset\emptyset$ terminal of the M37450 microcomputer 77. As described later with reference to FIG. 6, the interface unit 22 is programmed such that data transmission toward the cable 11 is permitted only when the cable is not busy. Connected respectively to the input and output terminals RXD and TXD of the M37450 are a receiver 80 and a driver 81 of the transceiver 78. The receiver 80 serves to shift the voltage level of ±13 V of signals on the cable 11 to 0–5 V so that signals applied to the RXD terminal can be processed by the M37450, while the driver 81 serves to level-shift the 0–5 V output from the TXD terminal of the M37450 to ±13 V signals for transmission onto the coaxial cable 11. Preferred examples of the receiver 80 and the driver 81 are the Line Receiver HD75189 and the Line Driver HD75188, respectively, marketed by Hitachi Ltd., of Tokyo, Japan.

Figure 6:
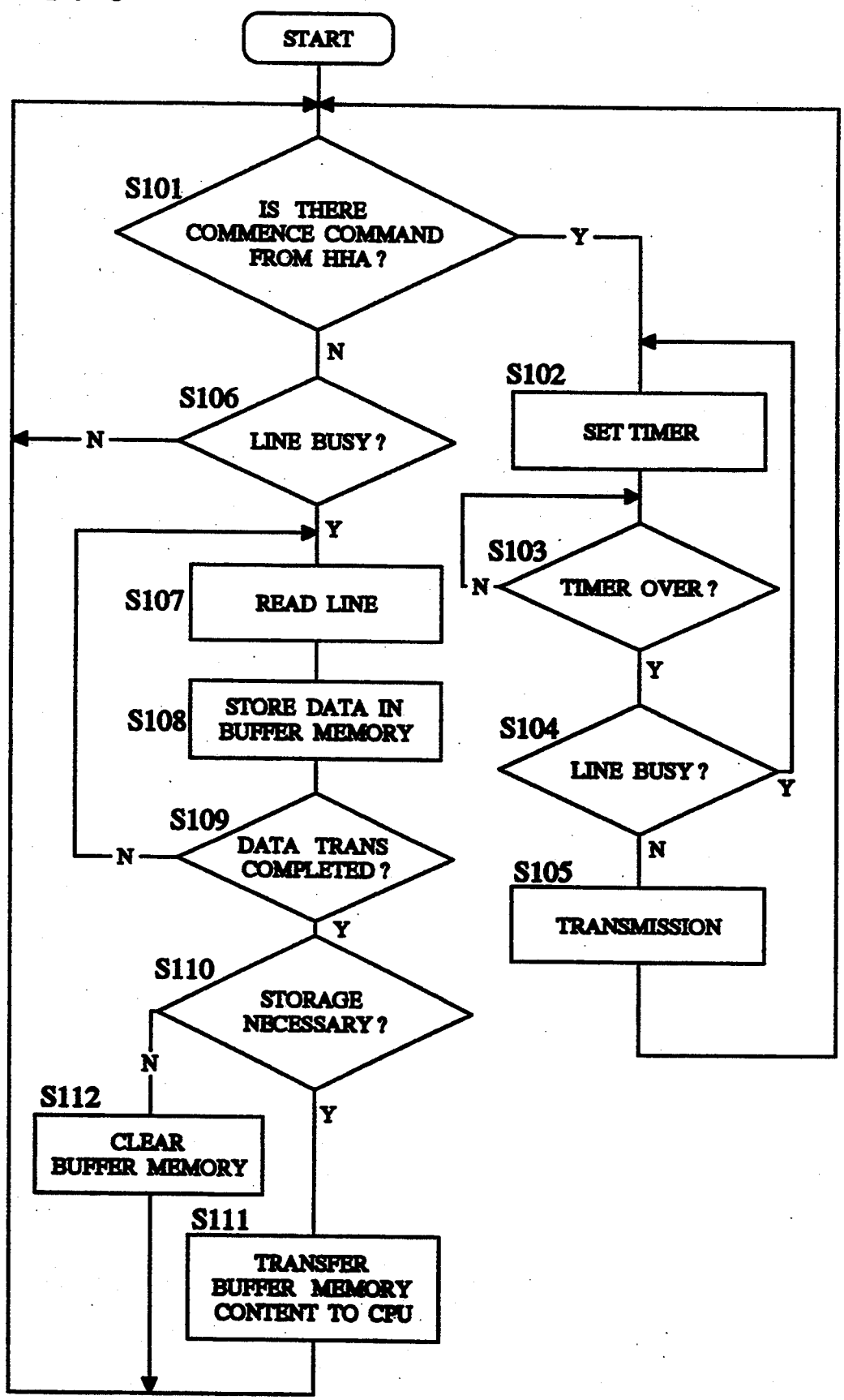
FIG. 6 is a flowchart showing the operation of interface units of the controller and the household appliances.

The communications interface units 22–30 are programmed generally to operate in such a manner as shown in the flowchart of FIG. 6. Referring to FIG. 6, each of the interface units 22–30 periodically checks the output from the corresponding microcomputer associated with the corresponding household appliance (HHA) to see if a command requiring commencement of transmission (transmission commence command) is issued from the corresponding microcomputer (Step S101). In this regard, as described later with reference to FIGS. 21, 26 and 33, a transmission commence command will be issued, for example, from the microcomputer 38, 42, 45, 48 or 55 associated with those household appliances having the vital information measuring and monitoring function to the corresponding interface unit when the individuals recognition data such as weight, stature or displacement is derived. Upon detection of the transmission commence command from the microcomputer 38, 42, 45, 48 or 55, the corresponding interface unit sets a timer for a predetermined time period (S102) and, as the time has elapsed (S103), checks at point S104 the output from the comparator (e.g., the comparator 79 of FIG. 5) to see if the coaxial cable 11 is busy. If the line is busy, then the timer is set again at S102. The purpose of decision S104 is to avoid collision of signals that would otherwise occur when a plurality of interface units commence transmission of signals simultaneously. The set period of timer may vary from interface unit to interface unit so that different interface units are discriminated in the order of priority. In that case, those interface units having shorter timer set period will make decision S104 more frequently than those having longer timer period so that the chance of commencing transmission will be given to the former units as soon as the line becomes free. When the line becomes free, the interface unit received the transmission commence command transmits data via its driver (e.g., the driver 81 of FIG. 5) to the coaxial cable 11 (S105). The foregoing transmission routine S101–S105 is carried out by the interface unit 22, 23, 24, 25 or 27 corresponding to the microcomputer 38, 42, 45, 48 or 55 when, for example, the individuals recognition data is detected.

As all the interface units 22–30 have their receiver (e.g., the receiver 80 of FIG. 5) connected to the coaxial cable 11, the signals sent at S101–S105 to the cable 11 from any one of the interface unit will be received by all the other interface units including the interface unit 26 for the controller 20. In addition, the interface unit that has just completed transmission S105 will be in a ready condition upon completion. All the interface units periodically check the transmission commence command (S101) and, in the absence of such command, check the line to see if it is busy (S106). As the line becomes busy due to data transmission from any one interface unit, each of the other interface units reads the signals on the line (S107) to store the transmitted data in its buffer memory (S108). Upon completion of data transmission (S109), each interface unit determines if it is necessary to store the received data in the memory of corresponding microcomputer or personal computer (S110). If unnecessary, the buffer memory is cleared (S112) and, if necessary, the data is transferred to the corresponding micro- or personal computer (S111) for storage in its memory (e.g., the RAM 73 of FIG. 5).

The controller 20 is programmed to operate as shown in the flowchart of FIG. 7, in order to provide the centralized storage and control of the vital information detected by respective testing and measuring devices associated with the household appliances as well as to furnish the testing and measuring instruments and the control devices of the household appliances with any vital information required for their operation. Referring to FIG. 7, the controller 20 first determines at point S121 whether the data stored in the memory 54 is to be sent to the coaxial cable 11. Decision S121 is intended to determine if any of the household appliances in the network requests the controller 20 to send data thereto and may be made based on a request-to-send indicator flag carried in the signal frame transmitted from the interface units 22–25 and 27–30 onto the cable 11. An exemplary serial data transmission format of such signal frame is illustrated in FIG. 8. As shown therein, the frame is headed by a 1-bit indictor flag, with a flag "1" meaning, for example, that there is a request to send from any of the household appliances and with a flag "∅" representing that there is no such request. If by checking the request-to-send indicator flag it is determined that data transmission is requested, the controller 20 then identifies at S122 the particular household appliance requesting transmission in accordance with an appliances identification number contained in the signal frame shown in FIG. 8 and recognizes at S123 the particular individual. If the signal frame sent from the interface unit of the appliance only contains the individuals recognition parameter (e.g., weight, stature or displacement) but not the individuals identification number (ID), this individual recognition is done by retrieving from the memory 54 of the controller 20 the individuals recognition data of all the members of the family and by comparing it with the value of the individuals recognition parameter sent from the particular appliance. If otherwise the signal frame sent from the interface unit contains the individuals identification number (ID), individuals recognition at S123 is done based on the ID number. Then at S124 the controller 20 looks into a table including the listings shown in column VI of FIG. 3 to see which kinds of data must be transferred to that particular appliance and sends at S125 the required data onto the coaxial cable 11. The format of the signal frame transmitted from the controller 20 may be similar to that shown in FIG. 8, with the exception that the request-to-send indicator flag is made "∅". If in the decision at S121 there is no request-to-send from any appliances, the controller 20 at S126 simply stores in the hard-disc memory 54 thereof the data conveyed from the appliances onto the cable 11.

Referring to FIGS. 9–22, the water closet system 12 will be described in more detail. As described before, the toilet system 12 incorporates vital data monitoring functions of urinalysis, electrocardiography, sphygmomanometry including pulse rate measurement, body fat content measurement and body weight detection.

Figure 9:
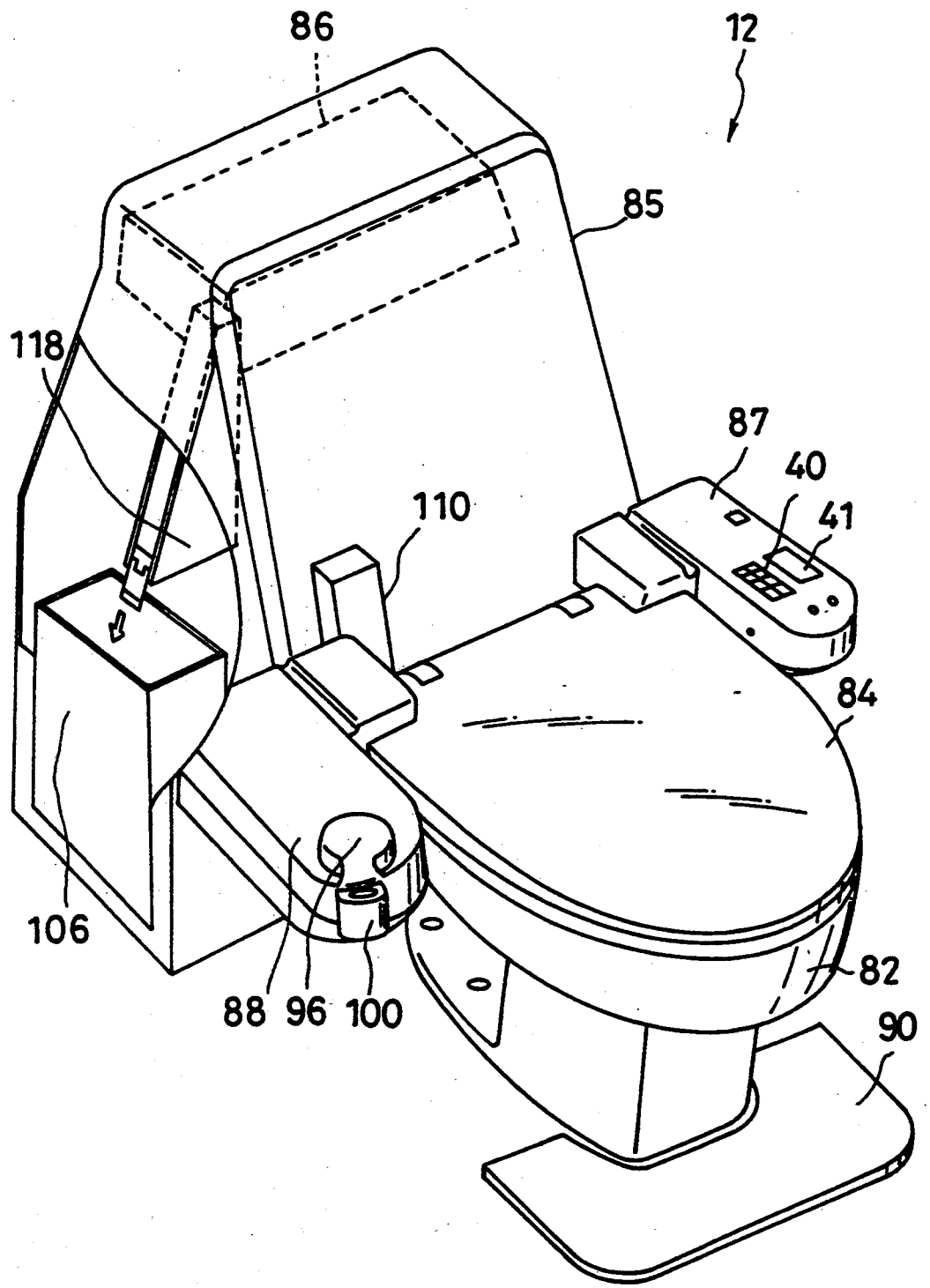
FIG. 9 is a perspective view, partly cut out, of a multiple-function water closet system incorporated in the health care and monitoring system of the invention.
Figure 10:
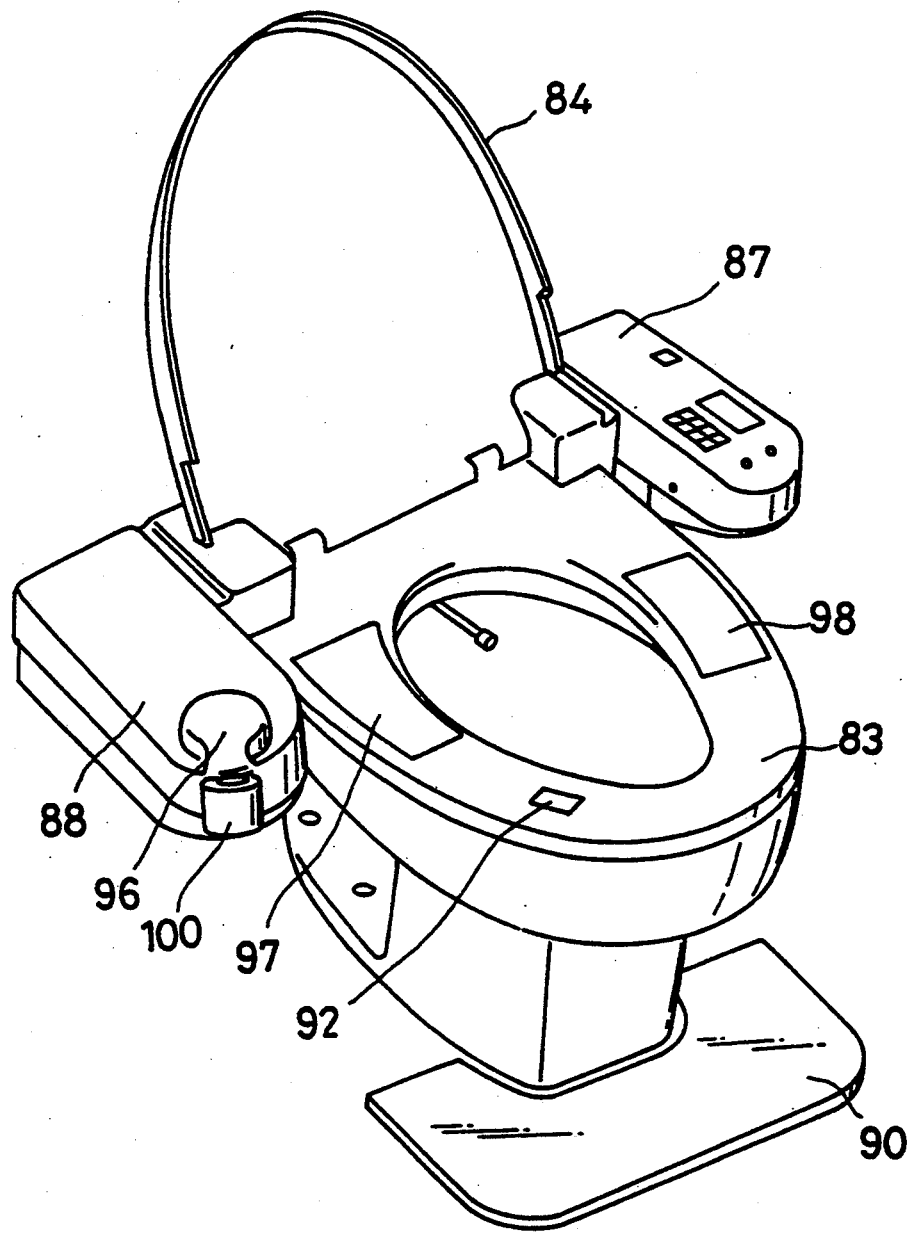
FIGS. 10 and 11 illustrate in part the water closet system shown in FIG. 9, with a cover lid and a toilet seat swung upwardly, respectively, to show the underlying arrangement.
Figure 11:
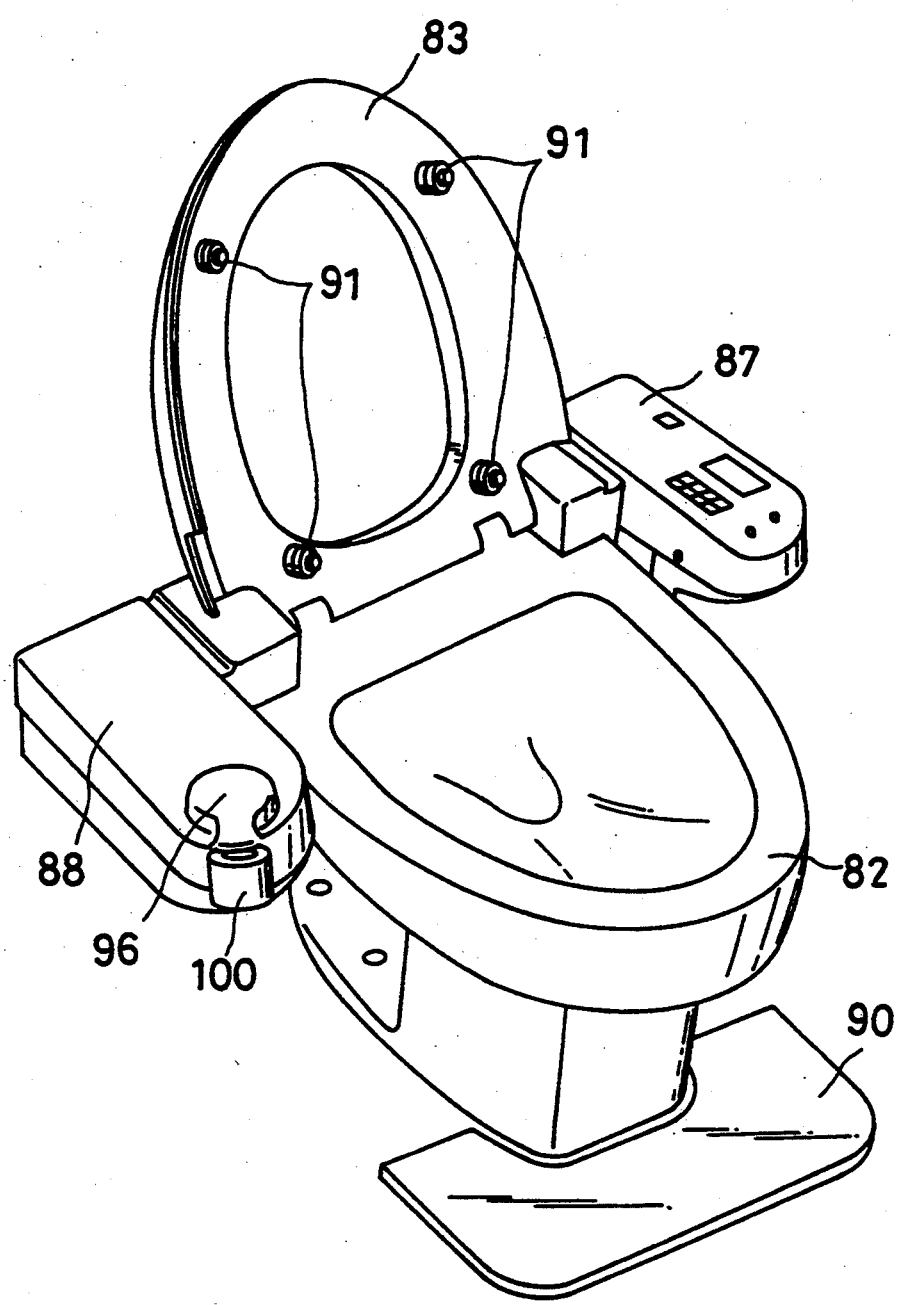
Figure 19:
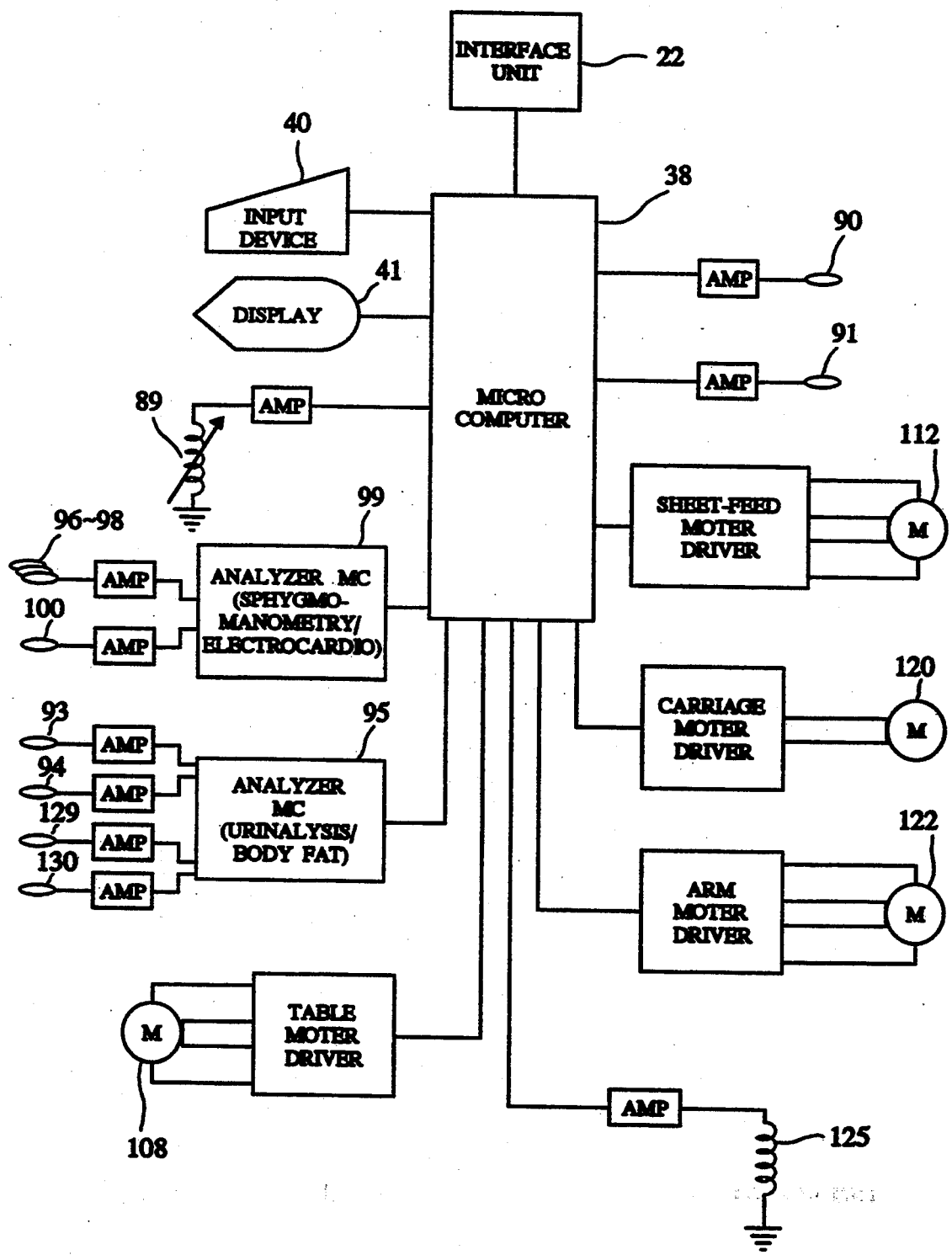
FIG. 19 is a block diagram of various testing and measuring devices and control devices associated with the water closet system shown in FIG. 9.

As shown in FIGS. 9–11, the toilet system 12 includes a toilet stool 82, a swingable seat 83, a lid 84, and a rear housing 85 wherein a conventional cistern 86 is disposed. The toilet system 12 is further provided with a pair of control boxes 87 and 88 serving also as the left-hand armrest and a right-hand armrest, respectively. The left-hand control box 87 is provided at its upper surface with the input device 40 and the LCD 41 of the measuring and control system 31 and houses therein a control device and a warm water storage reservoir (not shown) of a built-in bidet system which is knownas "Washlet TM". The right-hand control box 88 stores therein the microcomputer 38 and a sonic sensor 89, shown only in FIG. 19, which serves to detect urination. The sonic sensor 89 may comprise a conventional electromagnetic pickup and the output thereof is forwarded to an A/D converter circuit of the microcomputer 38 as shown in FIG. 19.

A first weight detector 90 is arranged in front of the toilet stool 82 to passively detect the body weight of the user. As the user accesses the toilet system for urination in a standing posture, the entire weight thereof is detected by the first detector 90. Further, as shown in FIG. 11, the toilet seat 83 is provided with four pressure sensors 91 adapted to cooperate with the toilet stool 82 to form the second weight detector. When the user is seated on the toilet seat 83, a substantial part of the body weight will be detected by the second detector 91, while the first detector 90 will function to detect the remaining part. The output from these detectors 90 and 91 are forwarded to the A/D circuit of the microcomputer 38 for calculation of the body weight. It will be understood that, whenever the water closet system 12 is used, detection of body weight is performed passively and automatically, without requiring positive instructions from the user.

As illustrated in FIG. 10, the toilet seat 83 is provided with a built-in sensor section 92 Of the non-destructive body fat testing and measuring instrument. This instrument is designed to operate on the principle described in U.S. Pat. No. 4,633,087 granted to Rosenthal et al. and the sensor section 92 thereof comprises a near infrared radiation emitting diode (IRED) 93 and a photosensor 94 schematically shown in FIG. 19. As shown in FIG. 19, the output of the photosensor 94 is applied to an analyzer microcomputer 95. The measurement of body fat content is also performed passively and automatically, as the user is seated on the toilet seat with his or her femoral region exposed to the sensor section 92. The IRED 93 emits near infrared radiation toward the exposed femoral region of the user, the intensity of reflected light being detected by the photosensor 94 for deriving the body fat percentage.

The toilet system 12 is also provided with functions of electrocardiography, sphygmomanometry and pulse rate measurement. The electrocardiograph is designed to detect and record electrocardiogram according to the second lead method wherein the potential difference between the right arm and the lower limbs is detected. To this end, the right-hand armrest 88 is provided with a first electrode 96 as shown in FIG. 10 to enable the user seated on the toilet seat to bring his or her right arm in contact with the electrode 96. The toilet seat 83 is provided with second and third electrodes 97 and 98 in such a manner that the right and left femoral regions are brought in contact with the electrodes 97 and 98 as the user is seated on the toilet seat. The outputs of these electrodes 96–98 are fed to an analyzer microcomputer 99 as shown in FIG. 19. It will be noted that, although the second and third electrodes 97 and 98 are brought into contact with the right and left lower limbs as a corollary of the user being seated on the toilet seat, it is nevertheless necessary for the user to intentionally position the right arm on the right-hand armrest 88 in contact with the first electrode 96 in order to have electrocardiogram recorded, so that some positive action by the user is required for the purposes of electrocardiography. Measurement of artery blood pressure and pulse rate is performed by a conventional digital sphygmomanometer operating on the principle of plethysmography. A measuring finger cuff 100 of the digital sphygmomanometer is disposed on the upper forward part of the right-hand armrest 88 and a control and drive of the sphygmomanometer is housed within the armrest 88 serving as a control box. As is well known, sphygmomanometry and pulse rate measurement is effected while the user inserts the right index finger into the finger cuff 100. Digital sphygmomanometers are available from various sources and, for the purposes of the present invention, the digital sphygmomanometer HEM801 marketed by Omron Corp., of Kyoto, Japan, may be suitably used. As shown in FIG. 19, output of the finger cuff sensor 100 is forwarded to the analyzer microcomputer 99. It will be noted that for sphygmomanometry and pulse rate measurement the user must insert his finger into the measuring cuff 100. Accordingly, positive intervention by the user is also required.

Figure 12:
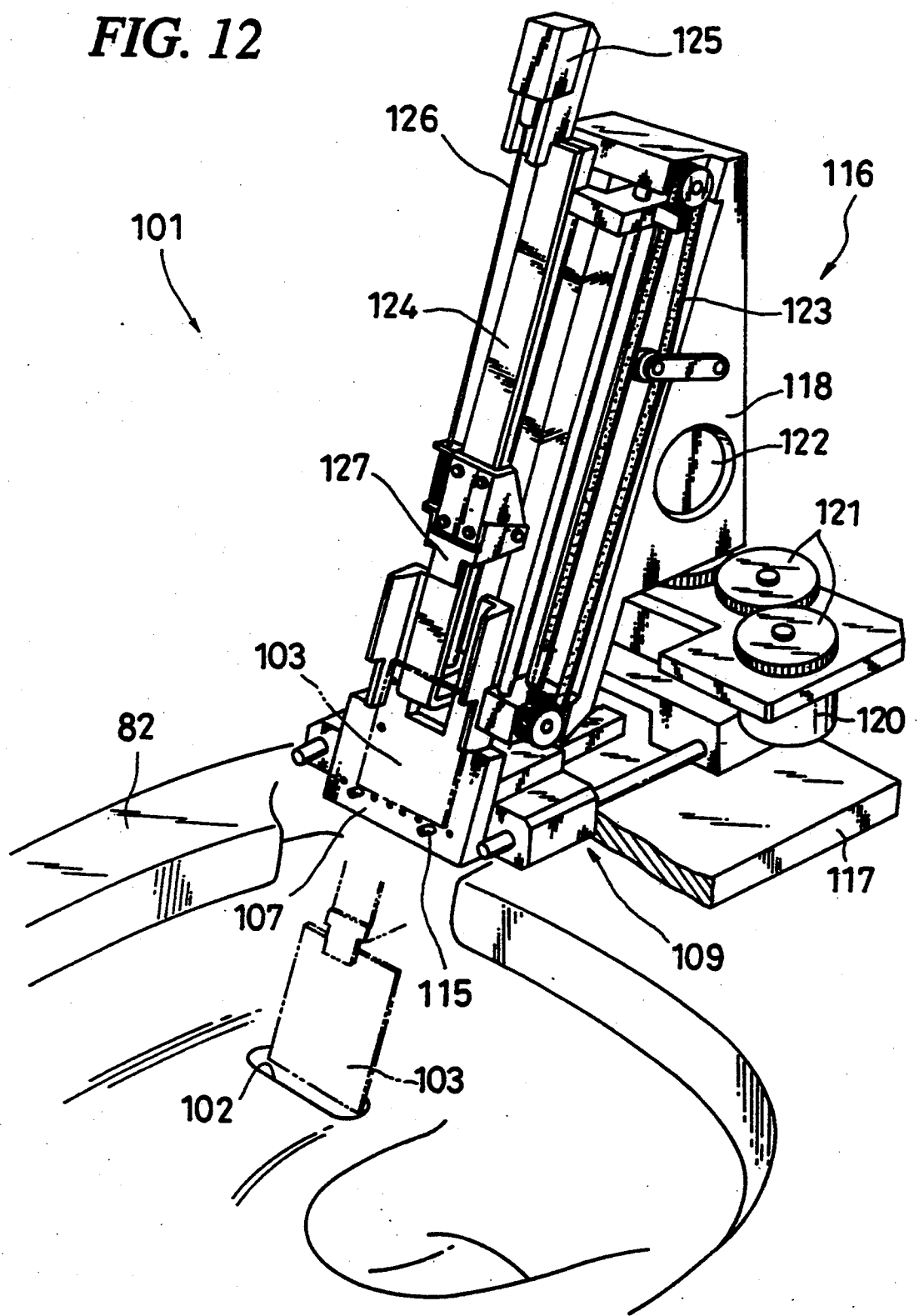
FIG. 12 is a perspective view showing a urinalysis apparatus provided in the water closet system of FIG. 9.

The toilet system 12 is further provided with an automated assay apparatus for sampling and analyzing urine. The urinalysis apparatus is similar in principle to the urine sampling and assay apparatus described in the copending patent application Ser. No. 07/748,211 filed Aug. 22, 1991, now U.S. Pat. No. 5,184,359 and assigned to the assignee of the present invention, the disclosure of which is incorporated by reference herein. To briefly describe below with reference to FIGS. 9–19, the urinalysis apparatus 101 is arranged within the rear housing 85 of the toilet system 12. As best shown in FIG. 12, the toilet bowl 82 is formed with a small urine sampling cavity 102 which is adapted to sample a small quantity of urine as the user urinates. A conventional assay and testing sheet 103 as shown in FIG. 15 may be used for urinalysis. As shown, each testing sheet 103 may include a substrate of plastics on which are affixed a plurality of coloring patches 104 impregnated with different reagents capable of exhibiting coloring reaction with biological substances contained in urine to indicate the heath condition of the individual. The reagents may be selected such that glucose, albumin, urobilinogen and occult blood, for example, are quantitatively determined.

Generally, the urinalysis apparatus 101 is designed and programmed such that, upon sensing urination by the user based on the sound detected by the sonic sensor 89, the assay sheet 103 is automatically contacted with urine in the sampling cavity 102 to allow reagents impregnated in the patches to react with urine and is then transferred to an analyzer head 105 (FIGS. 14 and 16–18) of the apparatus to determine the degree of coloring reaction for quantitative urinalysis. The testing sheet after analysis is automatically discarded into a trash 106 as shown in FIGS. 9 and 13.

More specifically, as best shown in FIG. 12, the urinalysis apparatus 101 includes an inclined movable table 107 for positioning the testing sheet 103. The table 107 is adapted for translational movement by a pinon-and-rack slider mechanism 109 driven by an electric motor 108 between a measuring position shownby the ghost line in FIG. 14 and a reference position indicated by the solid line and a stand-by position shownby the chain line. Each testing sheet 103 is supplied to the table 107 by an automatic sheet feeder 110 arranged at the rear housing 85 (FIG. 9) and having a casing 111 wherein a stack of testing sheets 103 are stored as shown in FIG. 14. Testing sheets 103 in the stack are fed one by one along a sheet transfer path 114 onto the table 107 in response to rotation of a pickup roller 113 driven by a stepping motor 112. The table 107 is provided at the lower end thereof with a pair of positioning pins 115 to ensure that the testing sheet 103 dispensed from the feeder 110 is located in position on the table as shown in FIG. 12.

Figure 13:
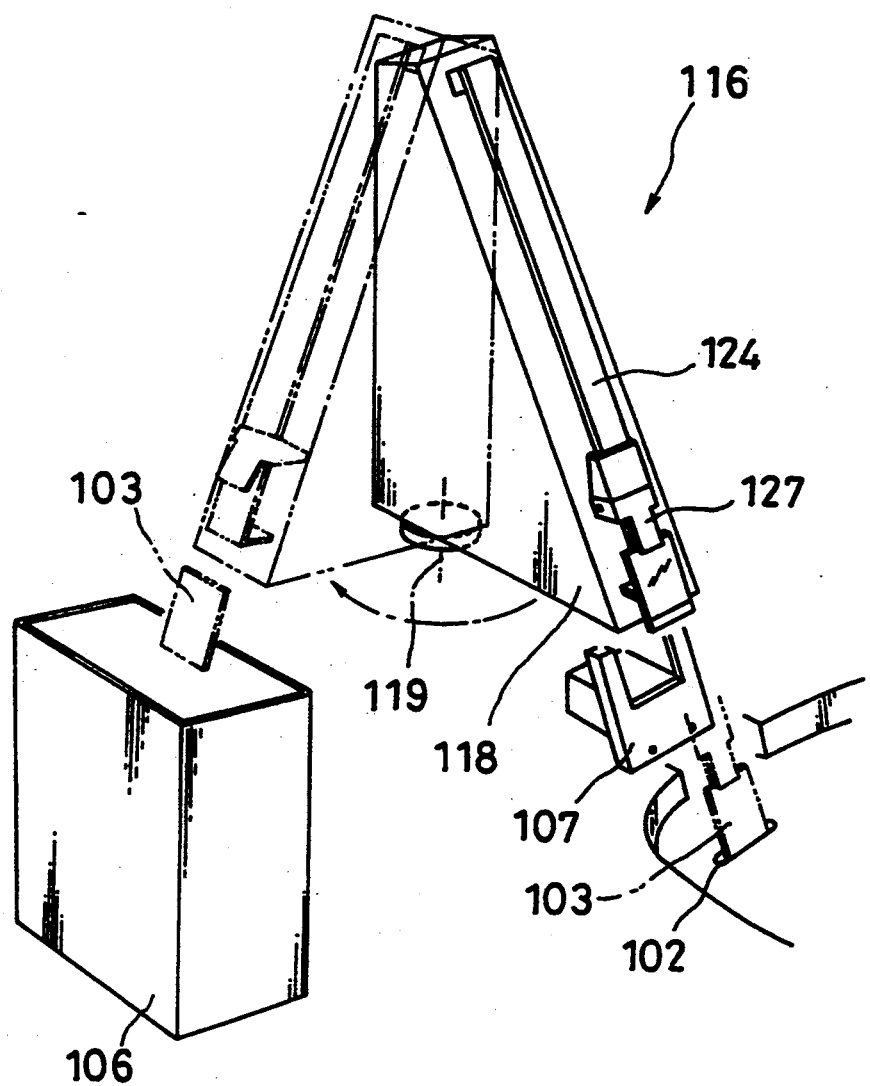
FIG. 13 is a schematic perspective view showing the operation of the urinalysis apparatus shown in FIG. 12.
Figure 14:
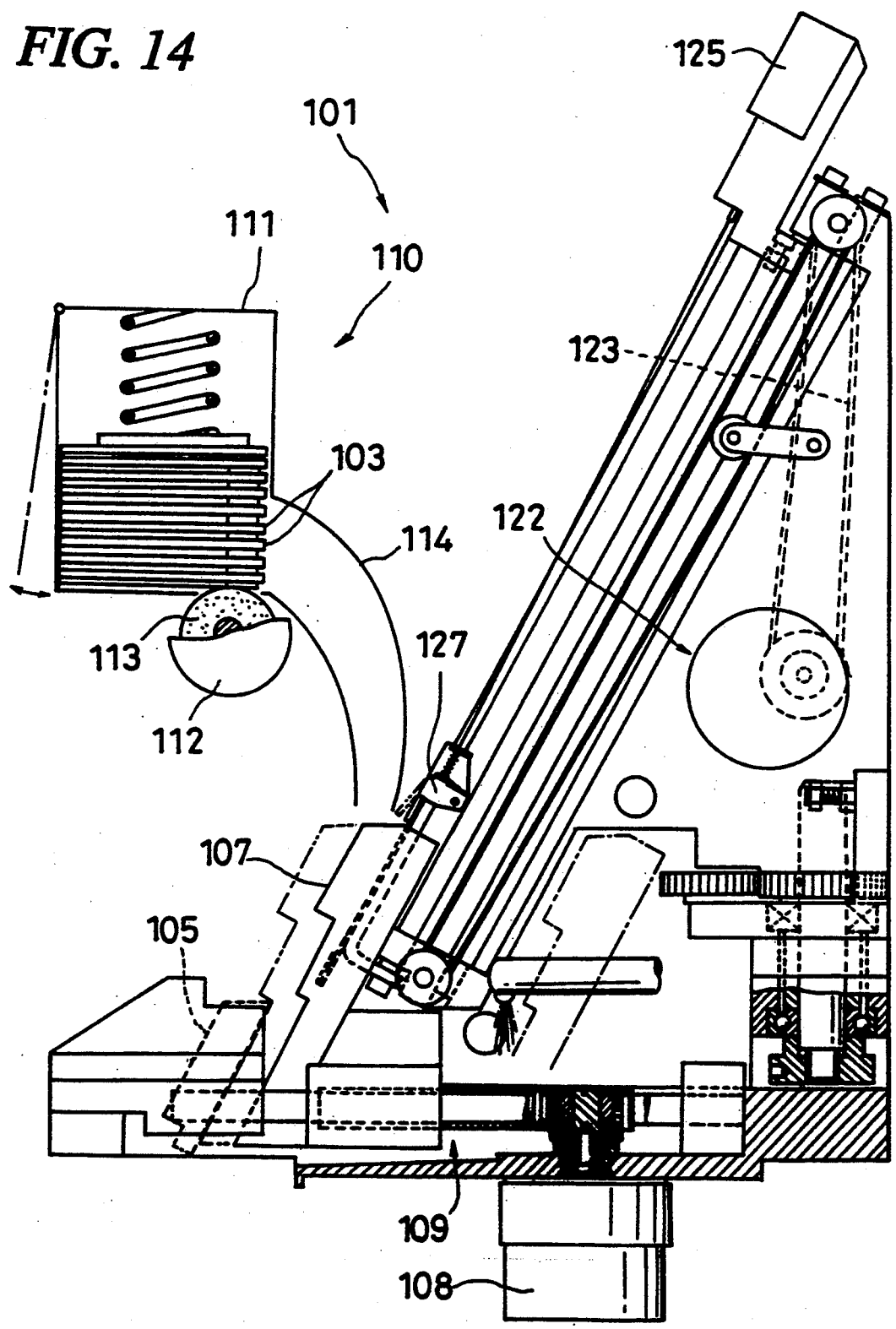
FIG. 14 is a side elevation of the urinalysis apparatus shown in FIG. 12.
Figure 15:
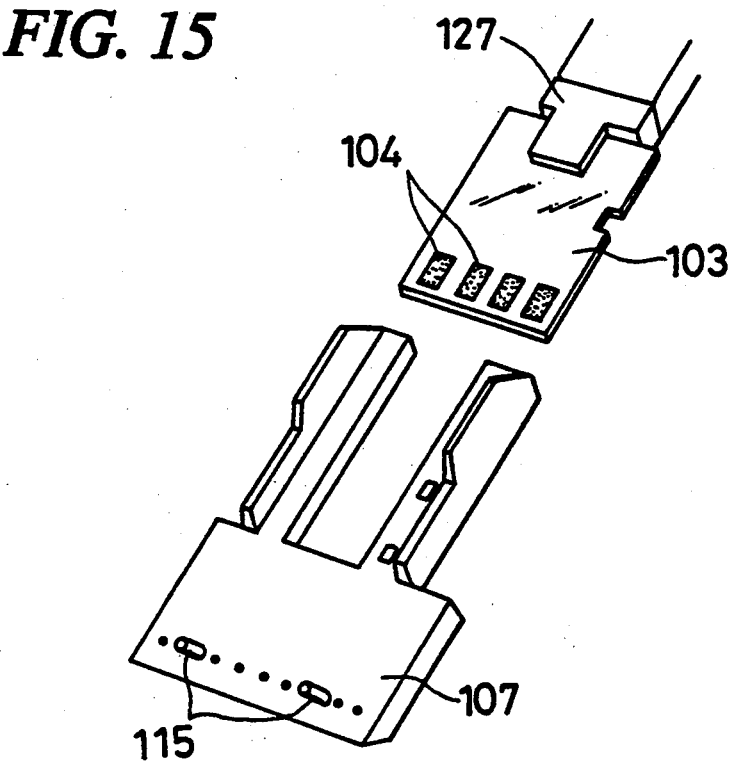
FIG. 15 is a perspective view illustrating a testing sheet of urinalysis being positioned on a movable table of the urinalysis apparatus of FIG. 12.

As shown in FIGS. 12–14, handling of testing sheets 103 is carried out by a sheet transfer mechanism 116 which includes a base 117 fixed on the toilet stool 82 and to which a swingable carriage 118 is mounted for swinging movement about a vertical axis 119. As will be readily understood from FIGS. 12 and 13, the carriage is adapted to be swung for about 90° about the vertical axis 119 by a gear train 121 driven by a motor 120. The carriage 118 is provided with a slidable arm 124 raised and lowered by a belt-and-pulley arrangement 123 driven by a motor 122, the arm 124 having a testing sheet clamping mechanism 127 operated by a solenoid 125 through a wire 126.

Figure 16:
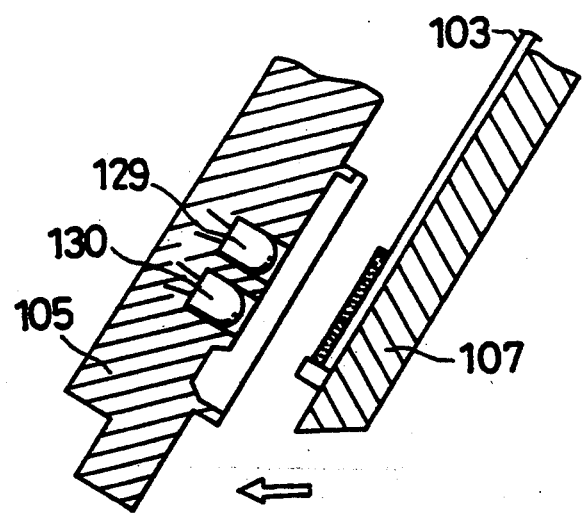
FIGS. 16 and 17 are cross-sectional views showing part of the urinalysis apparatus of FIG. 12 and showing, respectively, the movable table as moved away from and in contact with an analyzer head.
Figure 17:
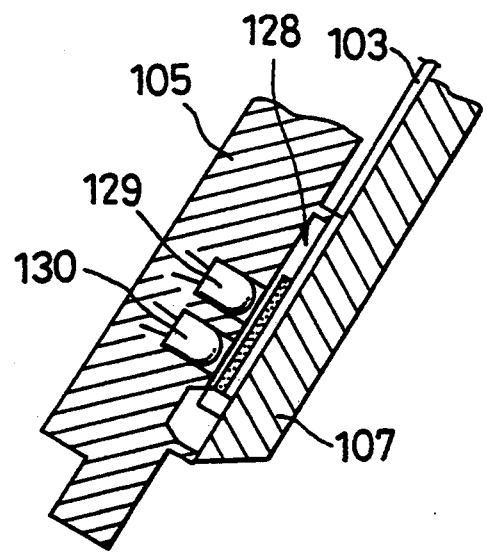
Figure 18:
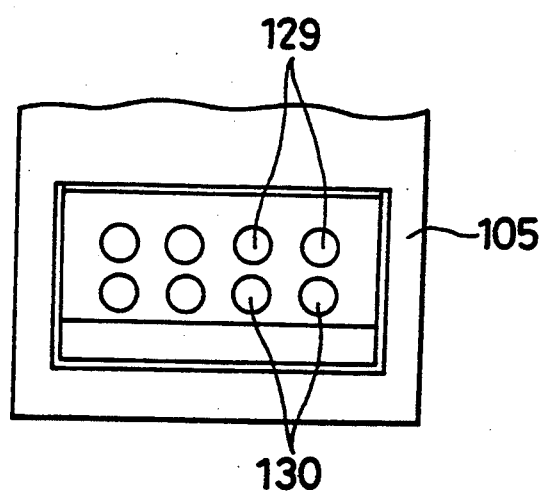
FIG. 18 is a rear view of the analyzer head shown in FIGS. 16 and 17.

As a testing sheet 103 dispensed by the sheet feeder 110 is placed in position on the table 107, the sheet clamp 127 clamps the sheet 103 and the table 107 is moved backward to allow the arm 124 to be lowered to dip the testing sheet into the urine pool sampled in the sampling cavity 102. The arm 124 is then raised and the table 107 is moved forward. Thereafter the clamp 127 is released to allow the testing sheet to be positioned again on the table 107. Then the table 107 is moved further forwardly as shown in FIG. 16 until the table is in contact with the analyzer head 105 thereby to form a dark room or camera 128 as shown in FIG. 17 wherein urinalysis is conducted by irradiating light from a series of light emitting diodes (LED) 129 in the analyzer head 105 to respective reagent patches 104 and by sensing the amount of reflected light by photosensors 130 to determine the intensity of coloring reaction of reagents. The output of the photosensors 130 is fed to the analyzer microcomputer 95 for urinalysis.

Figure 20:
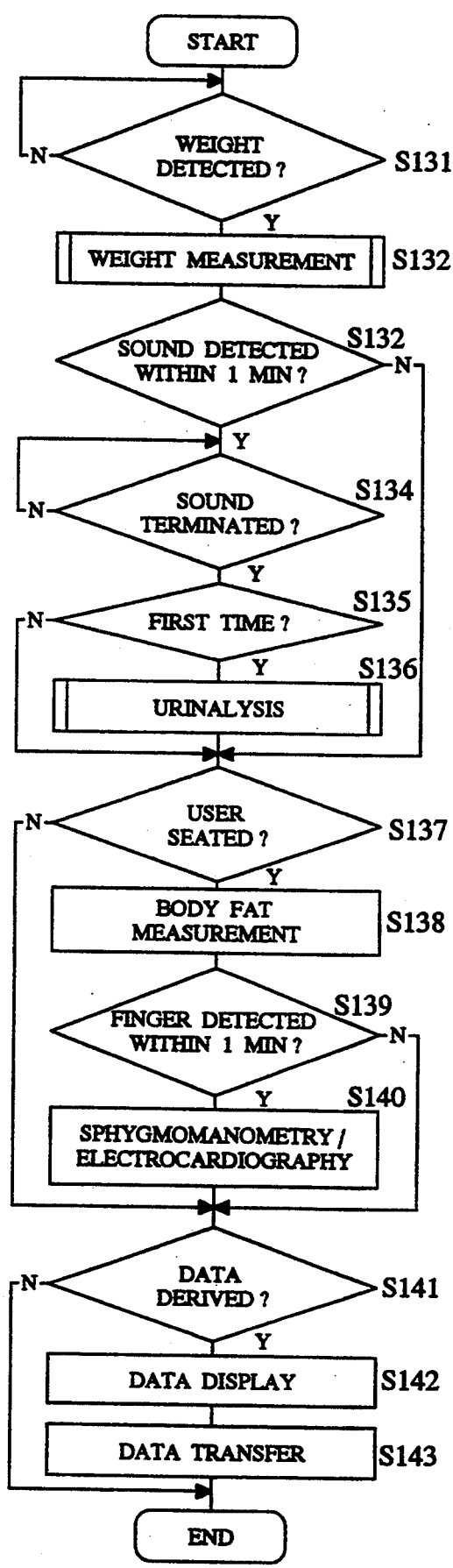
FIGS. 20–22 are flowcharts showing the operation of the water closet system shown in FIG. 9 as well as the operation of the devices associated therewith.
Figure 21:
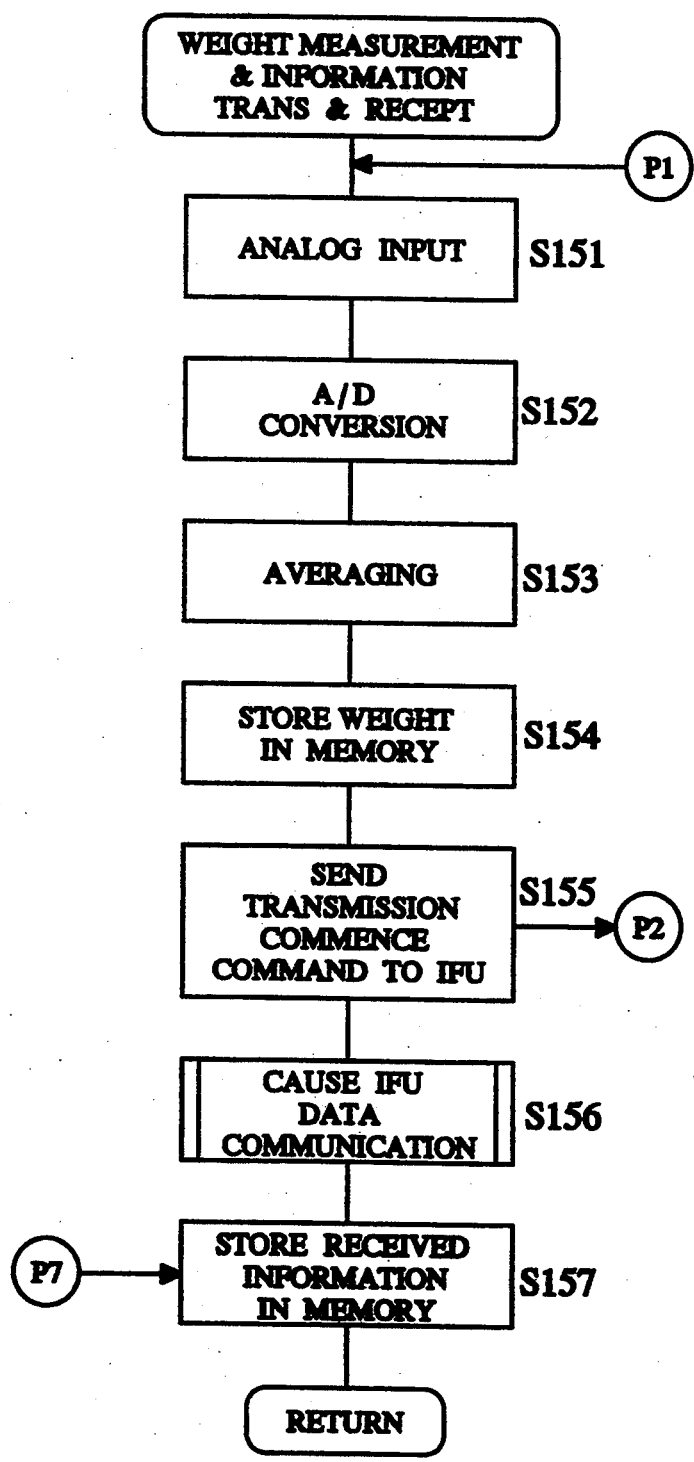
Figure 22:
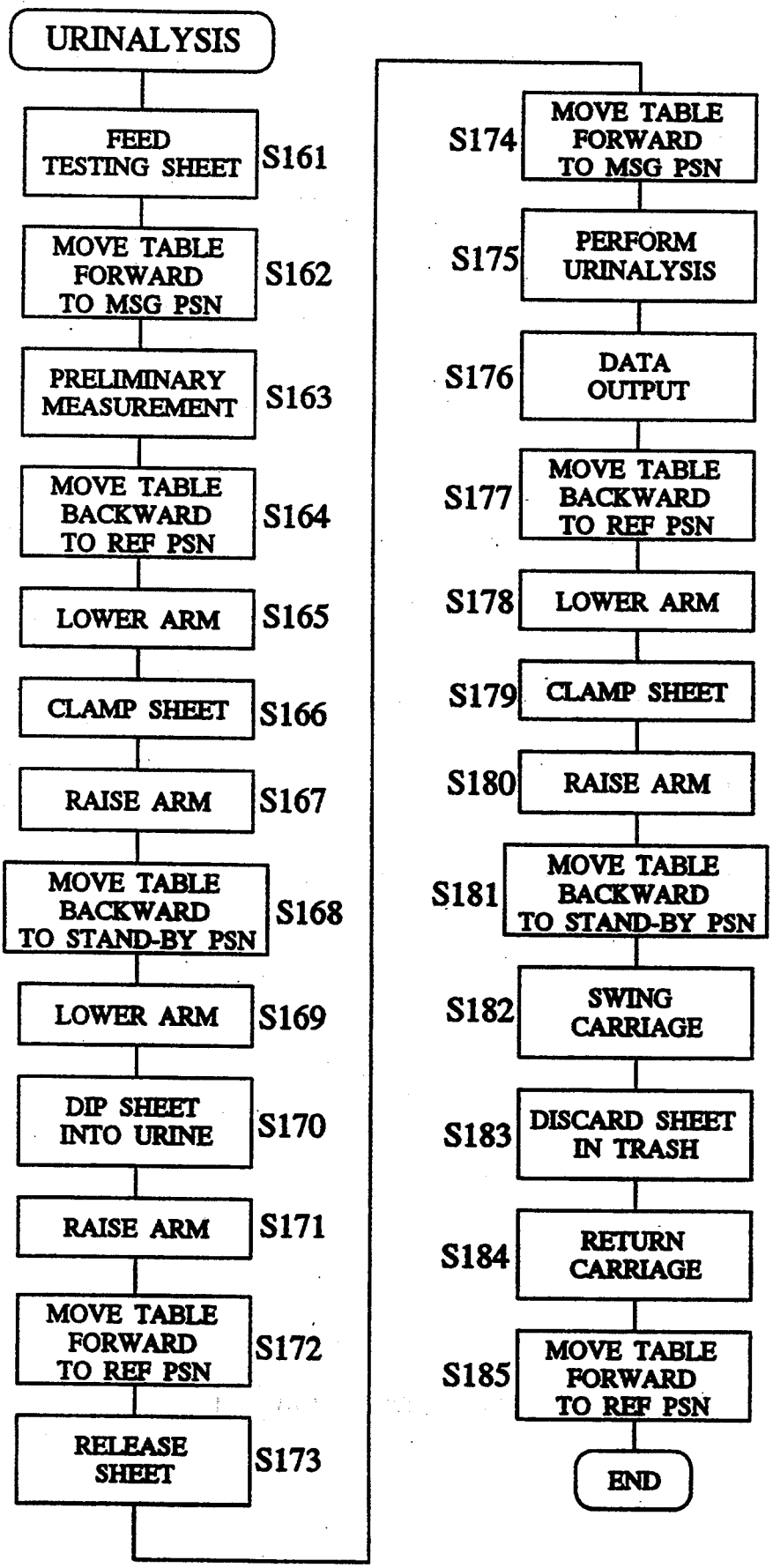

Referring next to the flowcharts of FIGS. 20–22 showing the operation of the microcomputer 38 of the toilet system 12, description will be made as to how the vital information is acquired by the testing and measuring devices associated with the toilet system 12 and how the resulting data is transmitted.

Referring to the flowchart of FIG. 20, as the weight of the user is sensed at S131 according to the signals from the first weight detector 90 and/or the second sensors 91 in response to the use of the water closet 12, the microcomputer 38 performs at S132 measurement of body weight and transmission and reception of information.

This step S132 of weight measurement and information transmission and reception is shown in more detail in FIG. 21 as a subroutine. As shown therein, the microcomputer 38 inputs analog signals from the detector 90 and/or sensors 91 (S151), converts the analog signals to digital signals (S152) and derives an average value (S153), whereupon the value is stored once in the memory 73 (S154). Then the microcomputer 38 sends a transmission commence command to the interface unit 22 (S155) to cause it to perform data communication (S156).

Data communication at S156 is a series of communications carried out between the interface unit (IFU) 22 of the microcomputer 38 and the interface unit (IFU) 26 of the controller 20 via the coaxial cable 11 and is performed in the following manner. Thus, as described before with reference to FIG. 6, upon receipt of the transmission commence command from the microcomputer 38, the IFU 22 sends at S101–105 to the cable 11 the weight value in the memory 73, headed by a request-to-send command, the appliances ID number and the kind of data (weight, in this case) as shown in the serial data transmission format of FIG. 8. The individuals ID number need not necessarily be included in the signal frame transmitted at this time.

Responsive to transmission from the IFU 22, the IFU 26 of the controller 20 performs data reception routine (S106–111 of FIG. 6), causing the received data to be stored in the RAM of the controller 20. The controller 20 then determines and recognizes the particular appliance and the particular individual (S122–123) and looks up the table of FIG. 3 (S124) to see which data must be sent to the toilet system 12, as described before with reference to the flowchart of FIG. 7. As the data which the controller 20 must furnish the toilet system 12 are those concerning the stature and sexuality of the individual as shown in column VI of FIG. 3, the controller 20 sends these required data to the coaxial cable 11, along with the appliances ID number and individuals ID number (S125). For this purpose, the IFU 26 of the controller 20 carries out the data transmission routine S101–105 shown in the flowchart of FIG. 6.

During transmission from the IFU 26 of the controller 20, the IFU 22 of the microcomputer 38 performs the data reception routine S106–111 of FIG. 6, causing the information received from the controller 20 (i.e., individuals ID number, the stature and sexuality of the individual) to be stored in the RAM of the microcomputer 38 (S157).

Referring again to the flowchart of FIG. 20, after acquiring the necessary information from the controller 20 in the foregoing manner, the microcomputer 38 of the toilet system 12 determines at S133 if the sonic sensor 89 has sensed a sound of urination within one minute from body weight detection. If the sound has been detected, the microcomputer 38 awaits until the sound is discontinued (S134) and then determines if the sound has been sensed for the first time (S135). This is to discriminate the sound of urination from any other sound that might be caused by flushing water. If the sound has been detected for the first time, the microcomputer 38 judges occurrence of urination and performs urinalysis at S136. If, otherwise, sound has not been detected within one minute from weight sensing, it is determined that the toilet system 12 is operated for purposes other than urination and urinalysis will not be conducted.

To describe the detail of urinalysis (S136) with reference to the flowchart of FIG. 22, as termination of urination is detected at S135 of FIG. 20, the microcomputer 38 signals the stepping motor 112 of the testing sheet feeder to rotate for a predetermined angle to cause a testing sheet 103 to be delivered onto the table 107 (S161). Then the table motor 108 is driven at S162 to move the table 107 forward until it reaches the measuring position shown by the ghost line in FIG. 14, whereupon preliminary measurement is effected at S163 to detect the initial color of reagents of the testing sheet prior to coloring reaction. The obtained data is stored in the memory of the analyzer computer 95 for use in subsequent urinalysis. Then, at S164 the table 107 is moved back to the reference position shown by the solid line in FIG. 14 and, after driving the arm motor 122 to lower the arm 124 at S165, the solenoid 125 is energized at S166 to clamp the testing sheet by the clamp 127. Then at S167 the arm 124 is raised and at S168 the table 107 is moved further backward to the stand-by position shown by the chain line in FIG. 14, whereupon the arm 124 is lowered (S169) to dip the testing sheet 103 into urine in the sampling cavity 102 (S170) formed on the toilet bowl. Thereafter, the arm is raised (S171) and the table moved forward to the reference position (S172). Upon releasing the clamp 127 at S173, the testing sheet will be placed in position on the table 107. The table is again moved forward to the measuring position wherein it is brought in contact with the analyzer head 105 (S174). After a lapse of predetermined time required for allowing the reagents to undergo proper degree of coloring reaction, urinalysis is conducted at S175 by detecting the change in color of reagents by the LED'es 129 and sensors 130. After causing the analyzer computer 95 to output the resultant data (S176), the table is moved backward (S177)

and the arm is then lowered (S178) to permit the clamp to hold the testing sheet (S179). The arm is then raised (S180) and the table moved back to the stand-by position (S181). Then at S182 the carriage motor 120 is driven to swing the carriage 118 to the position shown in FIG. 9, after which the clamp 127 is released to allow the testing sheet after urinalysis to be discarded in the trash 106 (S183). Finally, the carriage is returned to its initial position (S184) and the table 107 is moved forward to the reference position (S185), so as to be ready for subsequent urinalysis.

Referring again to FIG. 20, after the urinalysis routine (S136) is completed in the foregoing manner, a decision is made at S137 based on the signals from the pressure sensors 91 to see if the user is seated on the toilet seat. If seated, the sensor section 92 is operated to perform a non-destructive measurement of the body fat and the analyzer computer 95 is operated to derive the body fat content (S138). Preferably, computation of the body fat percentage is carried out by taking into account the stature and sexuality data acquired from the controller 20 and by following the estimation formula described in the article "Estimation of Body Fat by Near Infrared Spectroscopic Techniques" Sawai et al, Science of Physical Strength, vol 39, No. 3, June 1990, 155–163.

Upon completion of the body fat measurement (S138), a determination is made at S139 to check if the user has engaged the finger into the measuring finger cuff 100 of the digital sphygmomanometer within one minute from detection of seating. If the finger is detected, measurement of the artery blood pressure and pulse rate is performed (S140). Since during sphygmomanometry the right arm of the individual is positively kept in contact with the first electrode 96 on the armrest 88, electrocardiogram may also be detected according to the second lead method based on the output from the first electrode 96 in conjunction with the outputs from the second and third electrodes 97 and 98.

Thereafter, a decision is made at S141 to see if any vital 35 data has been derived as a result of the foregoing weight measurement, urinalysis, body fat measurement, sphygmomanometry including pulse rate measurement, and/or electrocardiography. If it has, the data is displayed at S142 on the LCD 41 and the microcomputer 38 causes at S143 the IFU 22 to transmit the data to the cable 11. The IFU 26 of the controller 20 receives the data from the microcomputer 38 and stores it in the memory 54.

In this manner, the vital data on body weight, urinal constituents and body fat percentage of the individual is passively monitored and obtained in response to the use of the toilet system 12 and is automatically stored in the memory of the controller 20. If the user is seated with his or her finger positively inserted into the measuring finger cuff 100, the vital data on artery blood pressure, pulse rate and electrocardiogram will additionally be acquired and stored in the memory.

Figure 23:
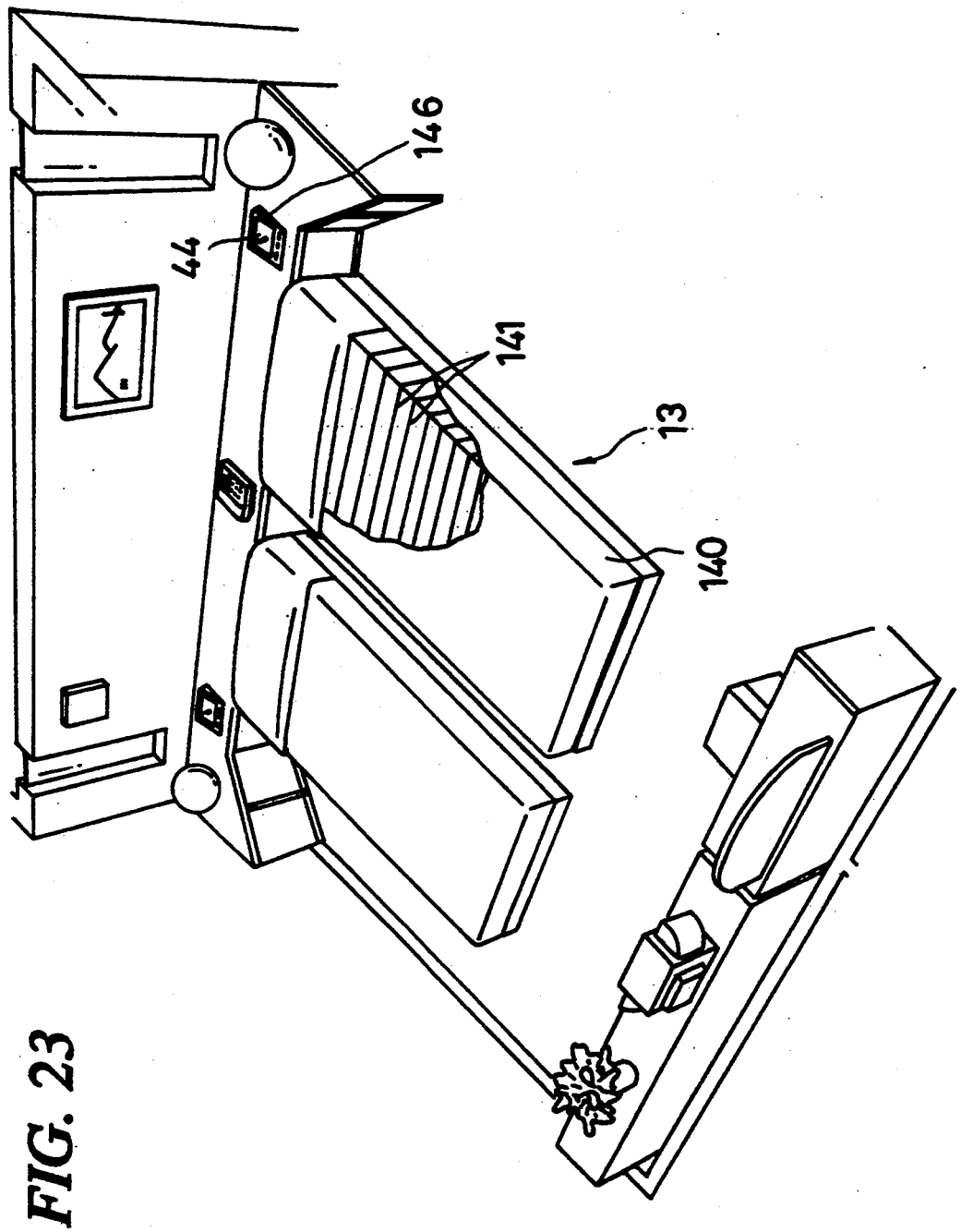
FIG. 23 is a perspective view, partly cut out, of a bed system incorporated in the health care and monitoring system of the invention.
Figure 24:
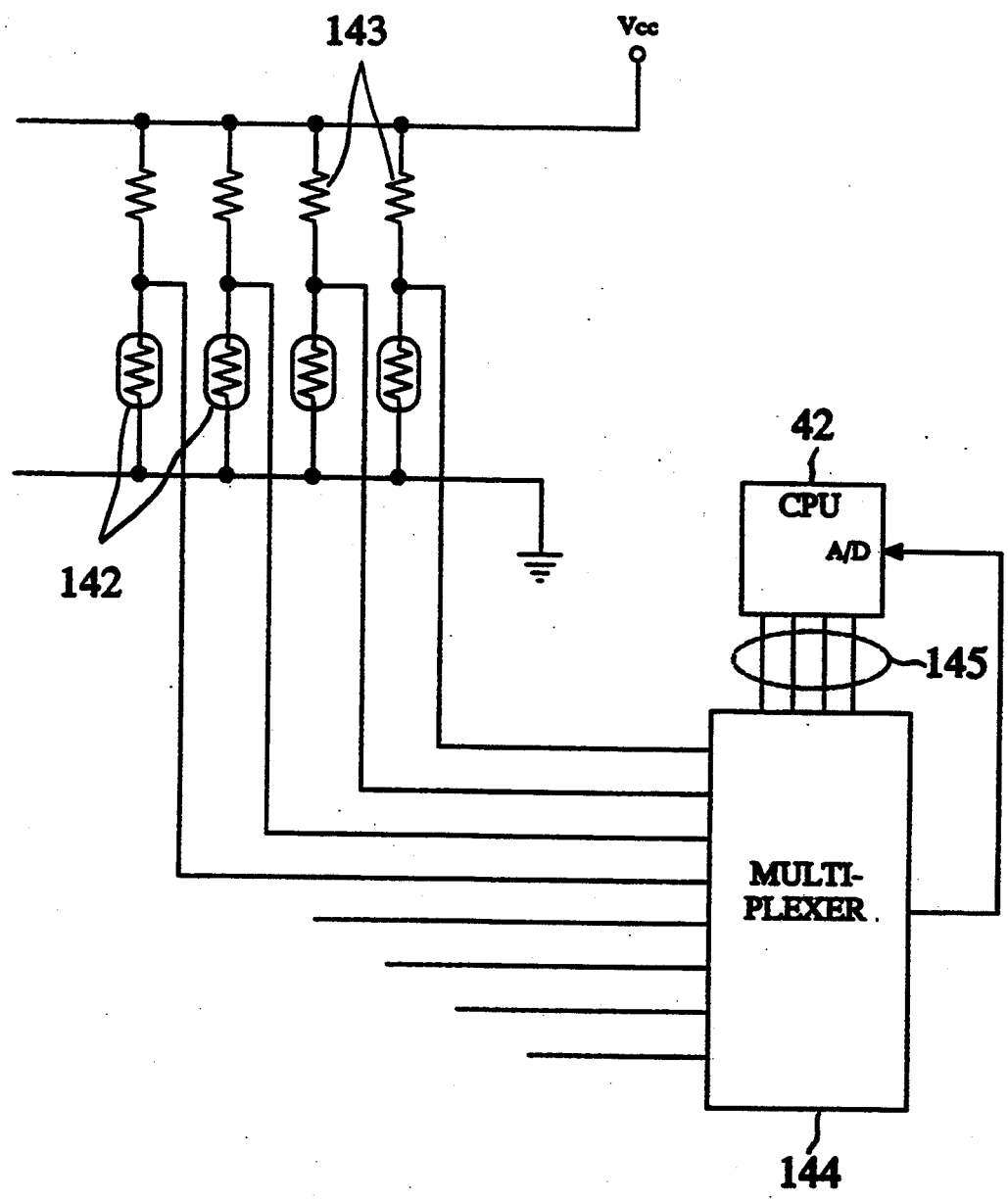
FIG. 24 is a wiring diagram showing an example of a thermistor matrix arranged in the bed shown in FIG. 23.

Referring next to FIGS. 23–27, the bed 13 of the network system will be described. In the embodiment shown, the bed 13 is adapted to measure the stature of the user, as the individuals recognition parameter, by detecting the temperature distribution on the bed as well as to measure the basal body temperature as the vital information. As shown in FIG. 23, the bed 13 incorporates a matrix of thermistors arranged within a mattress 140 and including, for example, twenty arrays 141 of thermistors. To ensure accurate measurement of the stature with fewer number of thermistor arrays, it is preferable to arrange the thermistor matrix such that the arrays 141 are sparse in the central part of the bed 13 and are dense in the peripheral part thereof. As the arrays 141 in the matrix may be identical with each other in arrangement, only one of them will be described with reference to FIG. 24. As shown therein, each thermistor array 141 comprises a plurality of thermistors 142 numbering, for example, eight in total. Each thermistor 142 has an end connected to a resistor 143 to which a reference voltage is applied and the other end grounded. The voltage level at the junction between the thermistor 142 and the resistor 143 is input via a multiplexer 144 into the microcomputer 42. To this end, the microcomputer 42 addresses the multiplexer 144 through a 4-bit address bus 145 to read the junction voltage in sequence. As the resistance of the thermistor 142 and, hence, the voltage at the junction vary in accordance with the temperature, it is possible to detect the temperature at a point in the matrix at which each thermistor is placed. Preferably, the arrays 141 of the thermistors 142 and associated lead lines only are arranged within the mattress 140, with the resistors 143, multiplexer 144, microcomputer 42 and IFU 23 being arranged in a control box 146 disposed aside of the bed 13.

Figure 25:
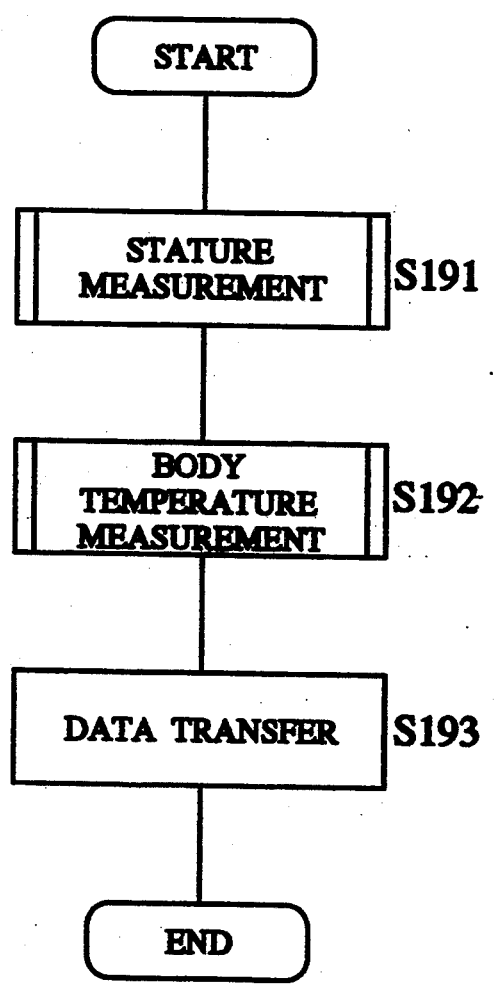
FIGS. 25–27 are flowcharts showing the operation of the bed system shown in FIG. 23 and of associated devices.
Figure 26:
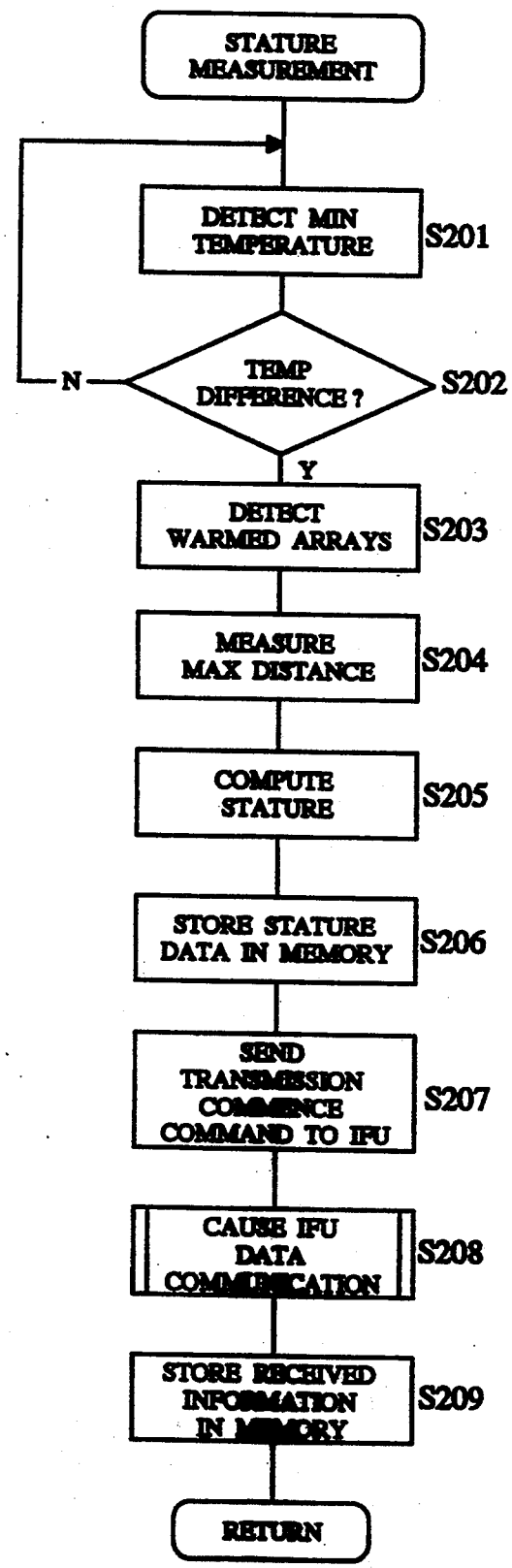
Figure 27:
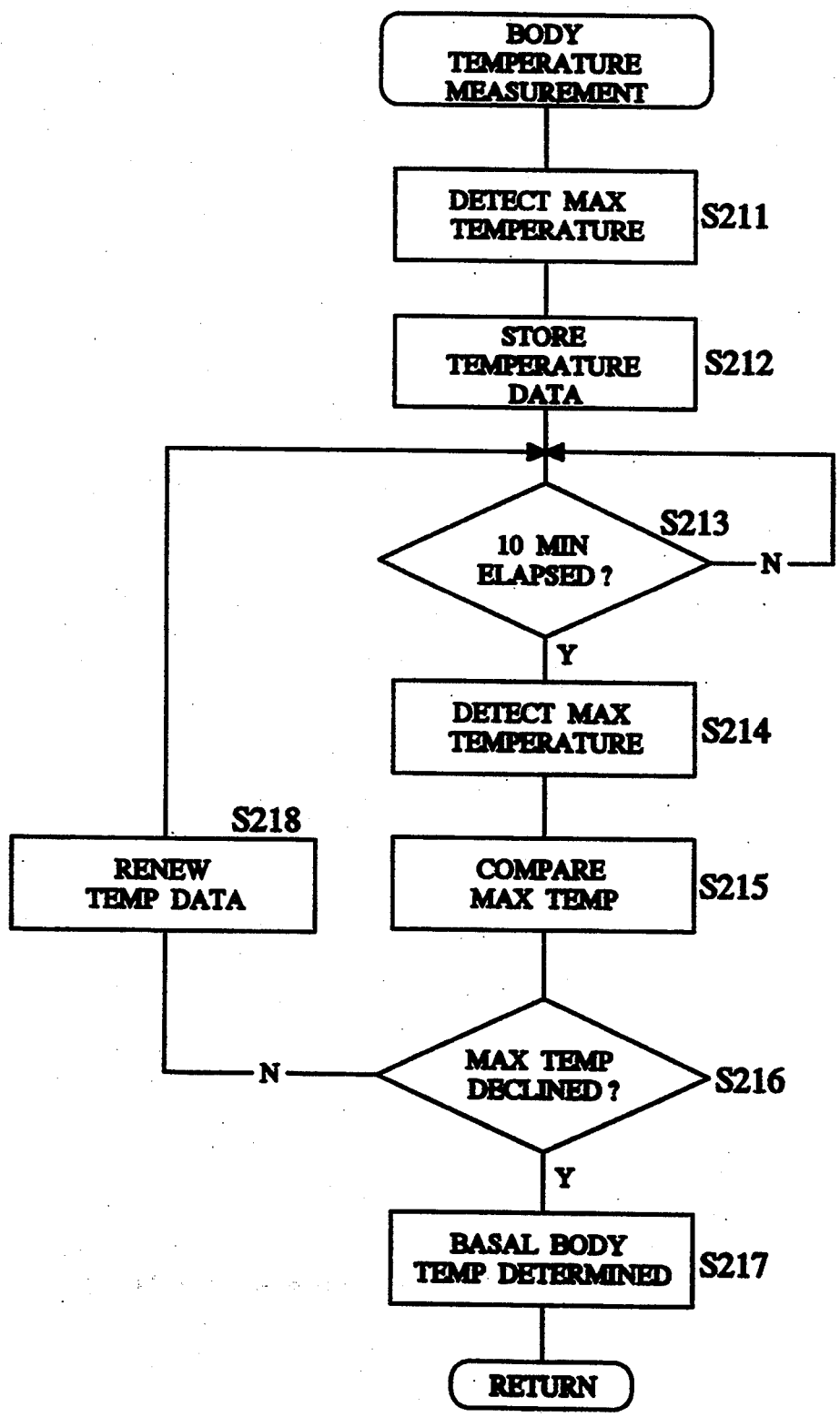

Measurement of the stature and body temperature according to the bed 13 as well as transmission of derived vital data will be described with reference to the flowcharts of FIGS. 25–27 showing the operation of the microcomputer 42. As shown in FIG. 25, the microcomputer 42 measures the stature of the user to cause the data to be transferred to the controller 20 (S191) and then detects the body temperature (S192) for transmission to the controller 20 (S193). The subroutines of stature and temperature measurements are shown, respectively, in FIGS. 26 and 27.

Referring to FIG. 26, the microcomputer 42 periodically checks at S201 all the thermistors 142 sequentially to detect the minimum temperature in the thermistor matrix and determines at S202 if any point in the matrix is subjected to a temperature higher than the minimum temperature. If the temperature of any point is raised, it is judged that the bed 13 is now in use and the microcomputer 42 then detects the arrays which are warmed (S203). Then the maximum longitudinal distance between the warmed arrays is measured (S204) to derive the stature of the user (S205). Because any points in the thermistor matrix in thermal contact with the user are warmed by the heat of the user lying on the bed and since the maximum distance between the warmed arrays is proportional to the stature of the individual, it is possible to estimate the stature by detecting the maximum 35 distance. By arranging the arrays 141 densely in the peripheral part of the bed as described hereinbefore, the stature may be detected for each increment of 2 cm. The microcomputer 42 temporally stores the acquired stature data in the memory (S206) and sends a transmission commence command to the IFU 23 (S207) to cause the IFU 23 to perform the data transmission routine S101–105 shown in the flowchart of FIG. 6 to transmit the stature data onto the coaxial cable 11 (S208). Since the bed 13 does not require transfer of data from the controller 20 as will be understood from column VI of the table of FIG. 3, the controller 20 transmits only the appliances ID number and the individual's ID number to the cable 11. The microcomputer 42 then stores in the memory thereof the information received via the IFU 23 of the bed (S209).

Referring to FIG. 27, in the body temperature measuring routine, the microcomputer 42 detects the maximum temperature in the thermistor matrix (S211), temporally stores the resulting data in the RAM (S212) and awaits for 10 minutes (S213). After a lapse of 10 minutes, the maximum temperature is again measured (S214) and is compared with the maximum temperature of previous measurement (S215) to determine if the maximum temperature has been lowered during the past 10 minutes (S216). In the absence of temperature lowering, the temperature data is renewed at S218. If a temperature decline has occurred within 10 minutes, it is judged that the user now awoke has left the bed 13 and the temperature detected 10 minutes before is determined as being the basal body temperature (S217). The vital data thus obtained is transferred to the controller 20 (see S193 of FIG. 25) for storage in the memory thereof. In this manner, the basal body temperature of the bed user is passively measured in response to the use and the derived temperature data is automatically stored in the controller 20.

Referring next to FIGS. 28-36, the bath system 14 and the associated equipments will be described. Generally, the bath system 14 is adapted to passively detect, as the useful vital information, the R—R interval of electrocardiogram that is believed to represent the degree of mental stress of human and is further designed to provide the bather with massage as well as to control the bath temperature for the purposes of health care.

Figure 28:
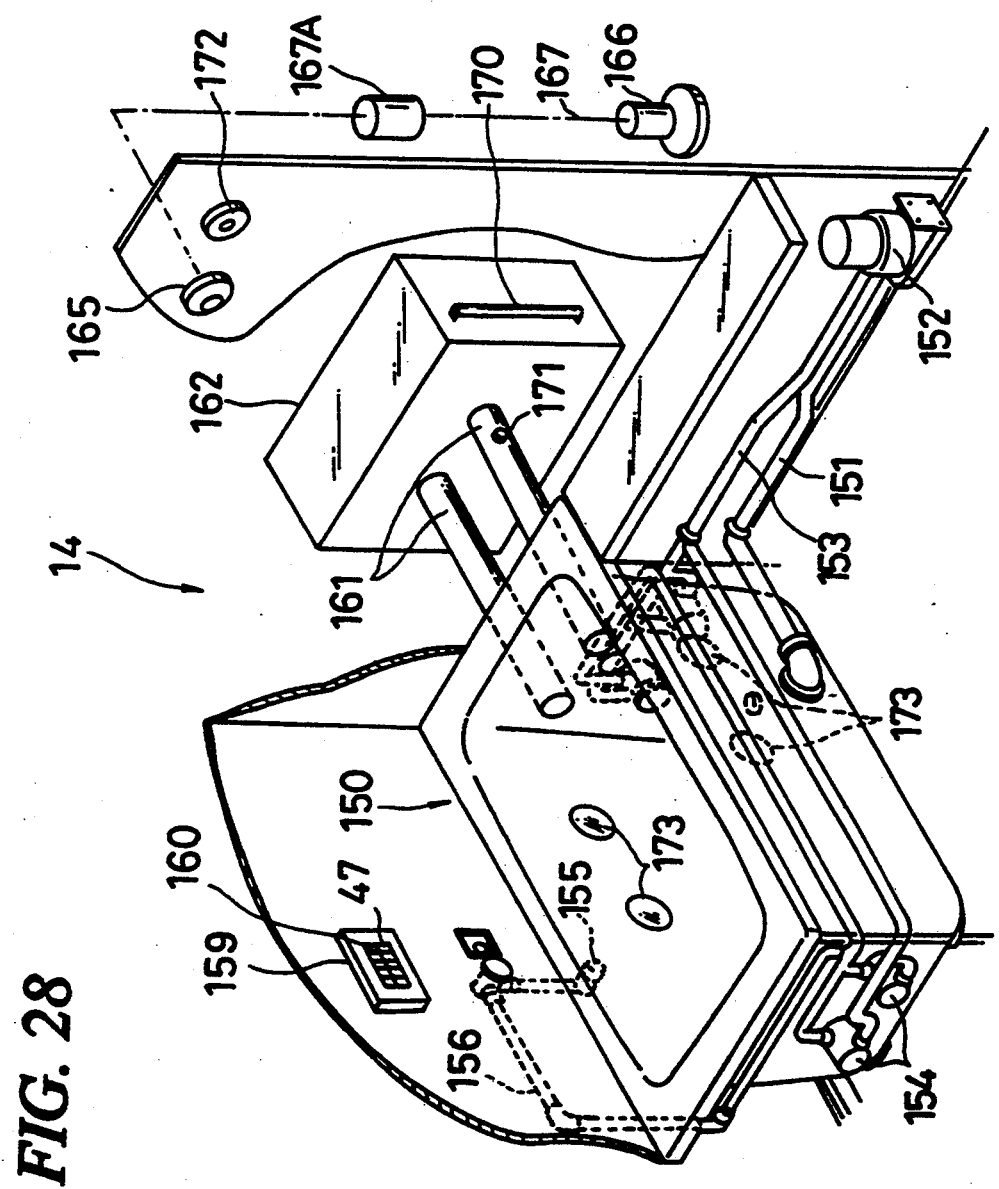
FIG. 28 is a perspective view showing a multiple-function bath system used in the the health care and monitoring system of the invention.
Figure 29:
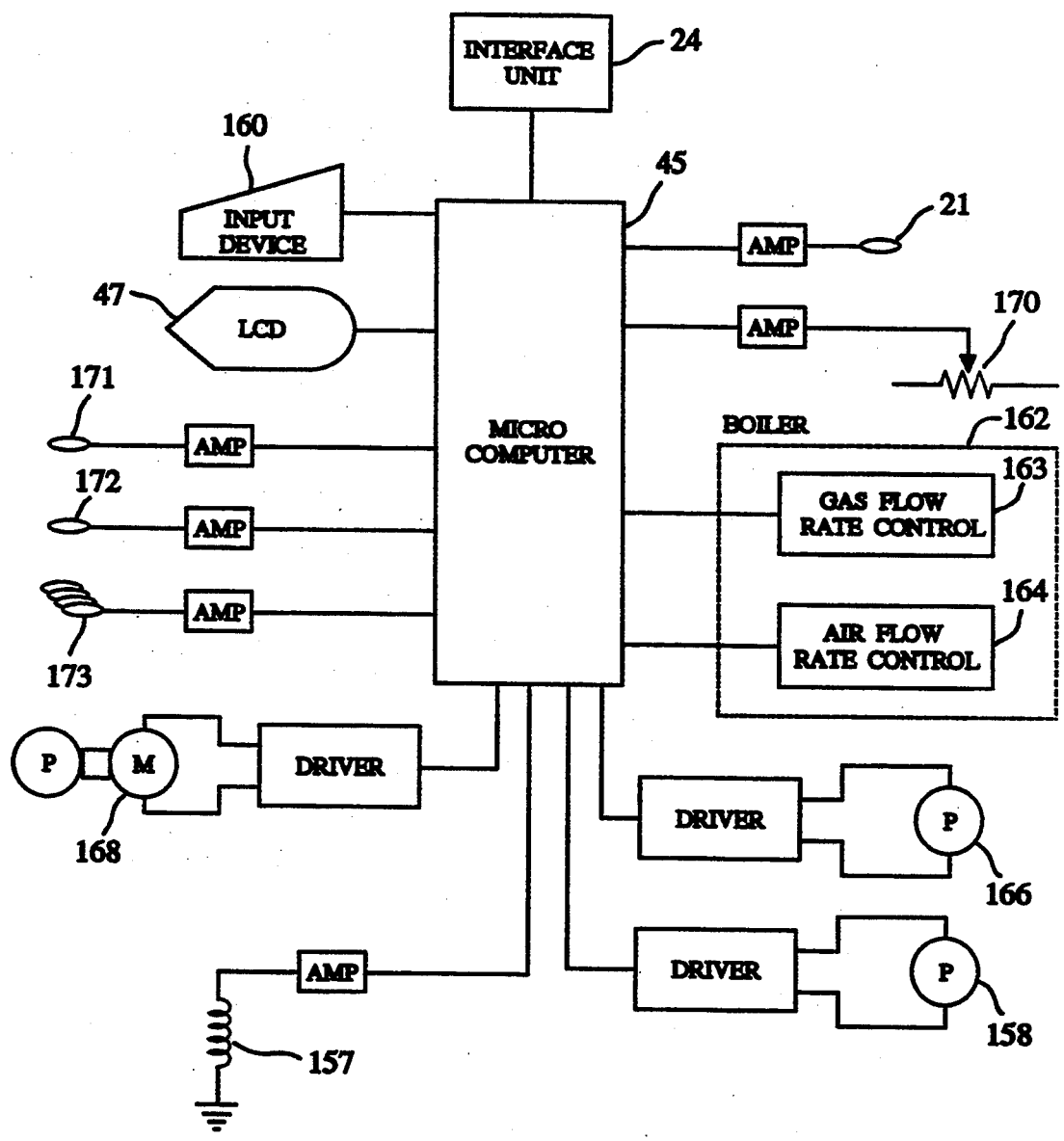
FIG. 29 is a block diagram of various testing and measuring devices and control devices associated with the bath system shown in FIG. 28.
Figure 30:
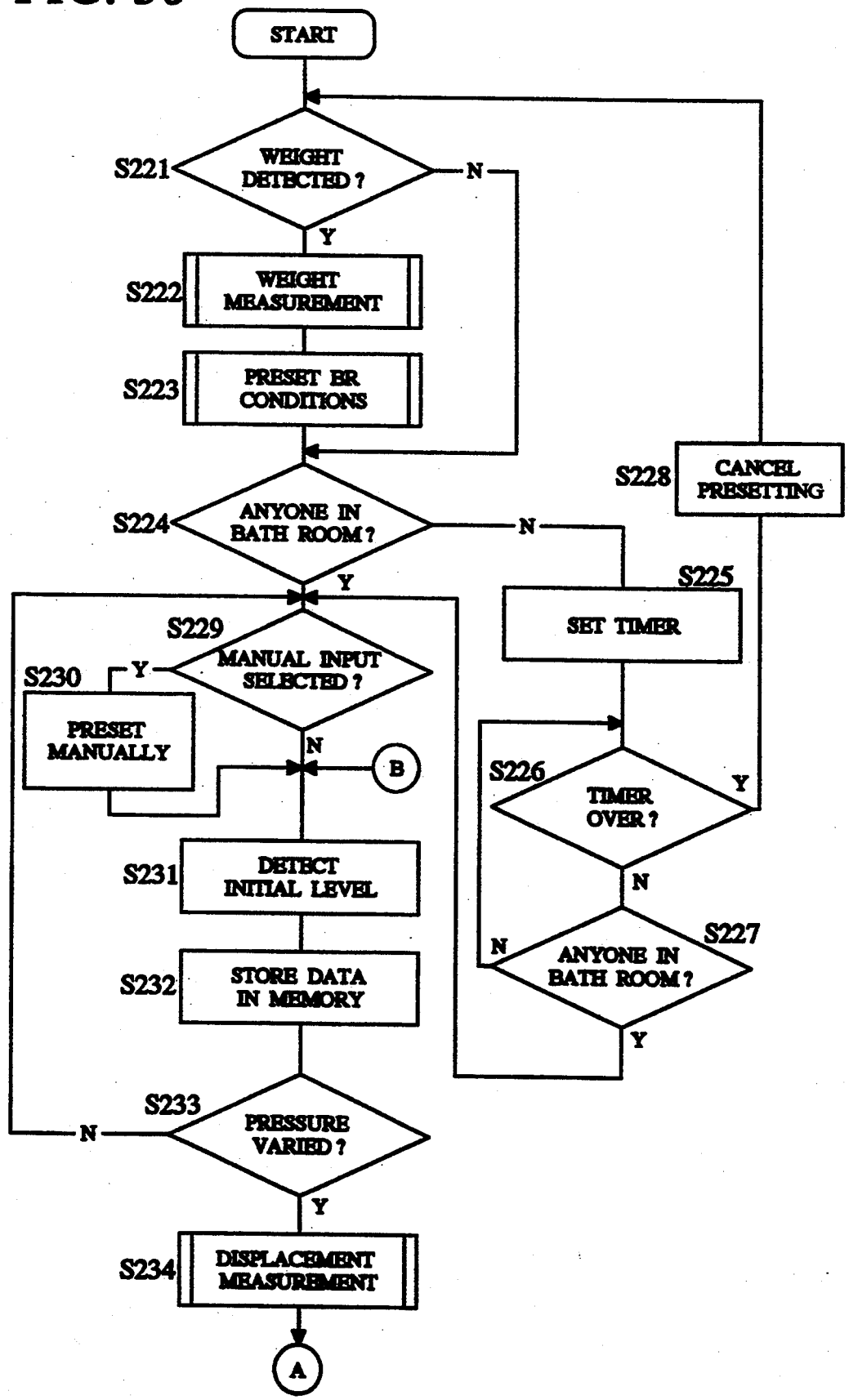
FIGS. 30–34 are flowcharts showing the operation of the bath system shown in FIG. 28 as well as the operation of the devices associated therewith.
Figure 31:
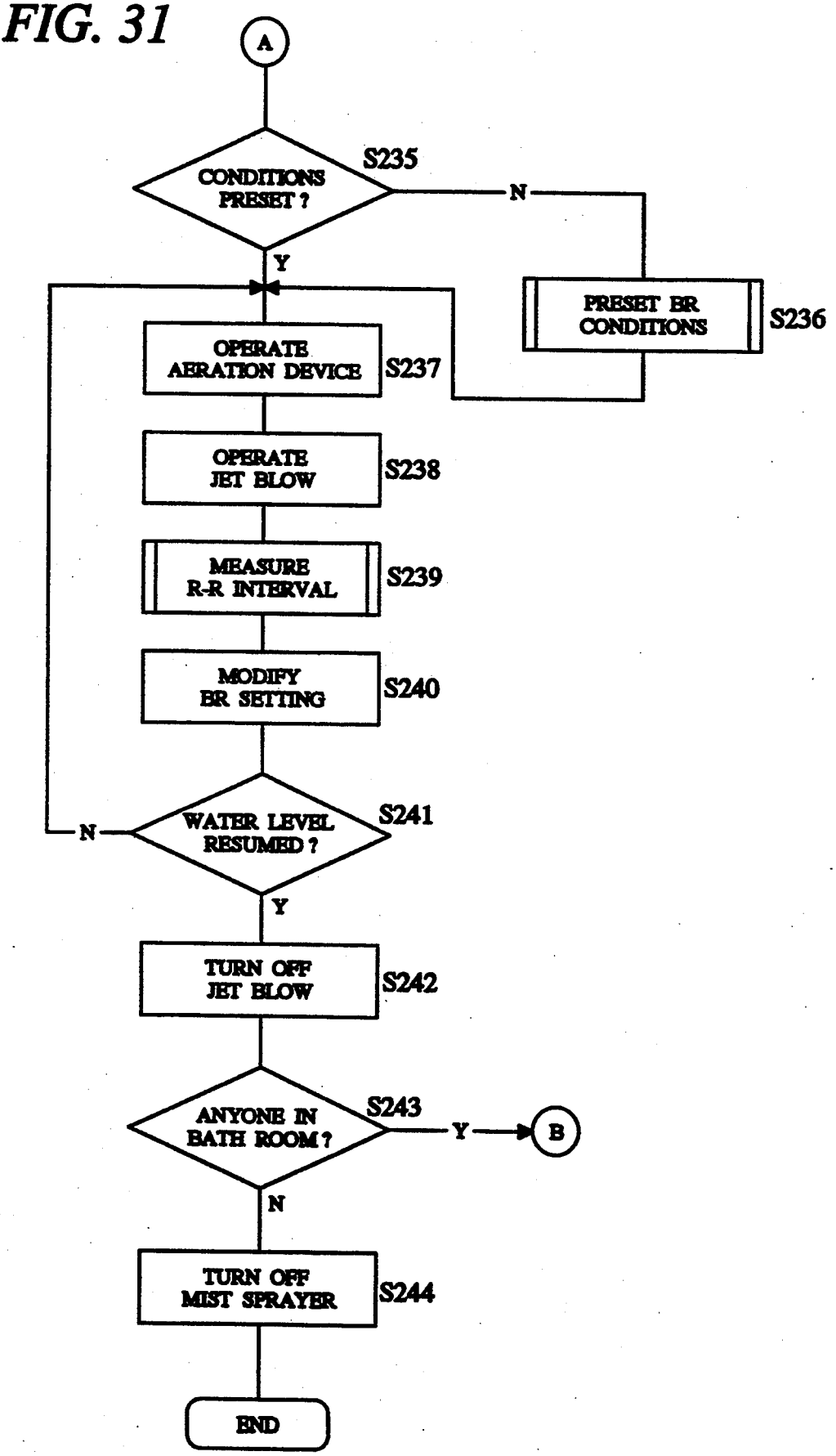

As shown in FIG. 28, the bath system 14 includes a bath tub 150 equipped with a jet blow system capable of generating jet streams of water in the tub. The jet blow system is conventional and is intended to give massaging effect to the bather. An example of the jet blow system is "Blow Bath TM" marketed by the assignee of the present invention. The jet blow system is adapted to circulate hot water in the tub through a pipe 151 to a pump unit 152 which pressurizes water to flow through a pipe 153 to a plurality, say four, of ejector nozzle units 154 wherein air bubbles are admixed to water flow to form jets of frothed water which are then injected into the tub. Each nozzle unit 154 comprises a solenoid valve which is designed to control the flow rate of air drawn from an air inlet 155 through an air pipe 156 for the purpose of aeration. As shown in FIG. 29, solenoids 157 of the solenoid valves of the nozzle units 154 and a motor 158 of the pump unit 152 are controlled by the microcomputer 45 which is arranged within a control box 159 fixed on the bath room wall. The control box 159 is provided with a manual input device 160 for use in manually setting the bathing conditions. Hot water in the tub is also circulated via a pair of circulating pipes 161 through a conventional gasburning boiler 162. As shown in FIG. 29, the boiler 162 is provided with gas control unit 163 for controlling the flow rate of gas supplied to the burner and with an air control unit 164 for controlling the flow rate of combustion air so that the temperature of hot water circulated through the bath tub is regulated by the microcomputer 45. The moisture content of the bath room is controlled by a conventional mist spray system. To this end, a mist spray nozzle 165 is mounted on the bath room wall as shown in FIG. 28 and is adapted to spray hot water pumped by a pump 166 through a supply pipe 167 having a heater 167A. The pump 166 has a motor 168 which is also controlled by the microcomputer 45 as shown in FIG. 29.

The boiler 162 is provided with a water level sensor 170 so as to detect the displacement of the body of the bather. Further, the circulation pipe 161 is provided with a pressure sensor 171 for sensing the presence or absence of the bather in the bath tub based on the pressure variation. Additionally, a photoelectric sensor 172 is provided on the bath room wall to detect the user in the bath room. The signals from these sensors 170-172 are forwarded to the microcomputer 45. Further, the bath tub 150 is provided at the lateral walls thereof with four electrodes 173 of electrocardiograph, the output of which is applied to the microcomputer 45.

Figure 32:
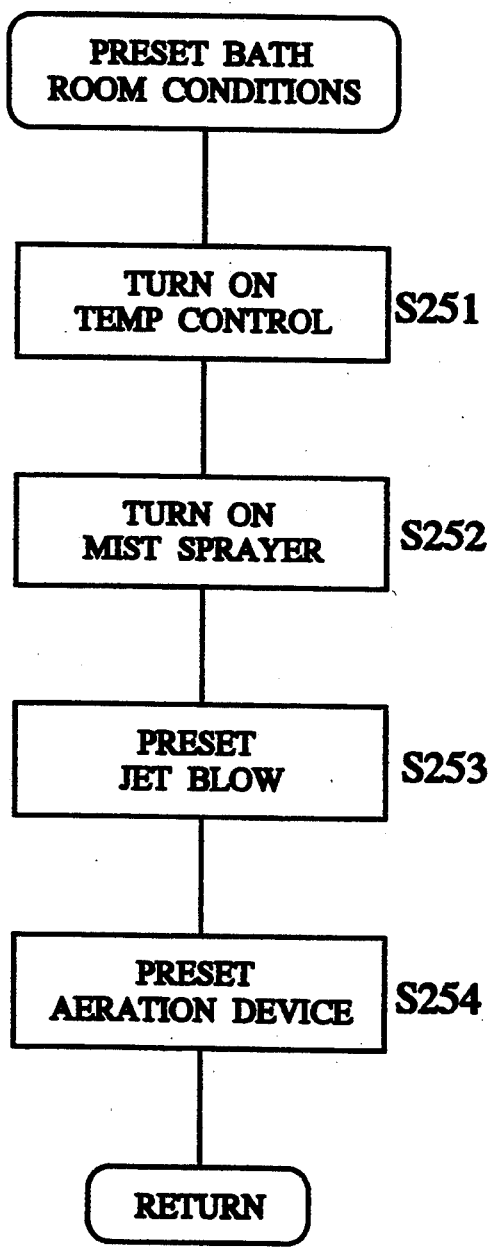

Operation of the bath system 14 and the related measuring and control devices having the health care functions will be described with reference to FIGS. 30-36. Referring first to the flowchart of FIGS. 30 and 31, the microcomputer 45 periodically checks at S221 the signals from the bath room scale 21 (FIG. 2) to see if a bather is detected at the entrance to the bath room. Even though the weight is not detected at the entrance, the photoelectric sensor 172 is cyclically checked at S224 to detect the bather who bypassed the scale 21 to enter the bath room. If the scale 21 has detected the weight of the bather, the microcomputer 45 then performs at S222 the weight measurement and information communication routine similar to steps S151-157 described before with reference to the flowchart of FIG. 21, thereby to receive from the controller 20 the data as shown in column VI of the table of FIG. 3, and thereafter presets the bath room conditions at S223. Presetting of the bath room conditions may be carried out, for example, as shown in the flowchart of FIG. 32. Thus, consistently with the data received from the controller 20 and including the body fat content of the bather and the amount of exercise representing the amount of perspiration during exercise with the ergometer 15, the control units 163 and 164 of the boiler is operated so as to establish a proper bath temperature (S251), the mist spray system 165/166 is turned on (S252), the intensity of jet blow by the pump unit 152 is determined (S253), and the degree of aeration at the nozzle units 154 is set (S254). The intensity of jet blow may be determined in accordance with the R—R interval of electrocardiogram detected in the previous measurement and the amount of exercise in such a manner that the massaging effect is increased in proportion to the degree of mental and physical exhaustion.

After preset of the bath room conditions, the photoelectric sensor 172 is checked to see if the bather has entered the bath room (S224). If nobody is detected, a timer is set (S225) to await for a predetermined time (S-226-227). In the absence of detection of the bather after a lapse of predetermined time from weight detection by the scale 21, it is determined that use of the bath room is not intended so that the bath room condition preset is cancelled (S228). If the bather in the bath room is detected, then at S229 it is determined if condition preset by the manual input device 160 is selected. If it is, the bath room conditions according to manual input is preset in preference (S230). Then the signals from the water level sensor 170 is checked to detect the initial level of hot water in the tub (S231) and the result is stored in the memory (S232). The signals from the pressure sensor 171 is then monitored to see if a change in the water pressure has occurred (S233). If pressure variation is detected, it is judged that the bather has now entered the bath tub and the measurement of displacement is performed (S234).

Figure 33:
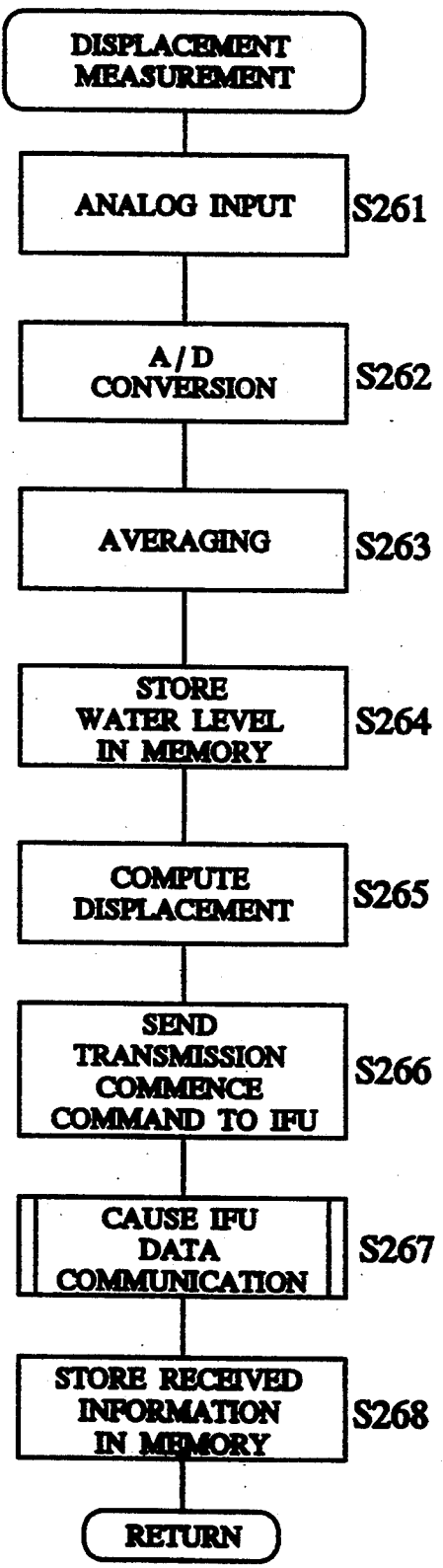

The displacement measurement routine S234 is carried out as shown in more detail in the flowchart of FIG. 33. Similar to the body weight measurement routine described before with reference to FIG. 21, the measurement routine S234 is intended to detect, as the individuals recognition parameter, the volumetric displacement of the body of the bather for transmission to the controller 20 and to receive therefrom necessary data required for the measuring and control devices associated with the bath system 14. Referring to FIG. 33, the microcomputer 45 inputs analog signals from the level sensor 170 (S261), converts the analog signals to digital signals (S262), calculates the average level (S263) and temporally stores the resulting data in the memory (S264). Then the displacement, which is the volume of water displaced by the bather entered into the tub, is derived at S265 by comparing the initial level detected at S231 with the average level calculated at S263. Similar to the weight measurement routine described with reference to FIG. 21, the microcomputer 45 sends a transmission commence command to the IFU 24 (S266) to cause it to perform data communication (S267) and stores the data received from the controller 20 in its memory (S268). As will be apparent from column VI of the table of FIG. 3, the controller 20 supplies information concerning the body fat percentage, artery blood pressure and pulse rate, amount of exercise and R—R interval of cardiogram detected during previous measurement.

Figure 34:
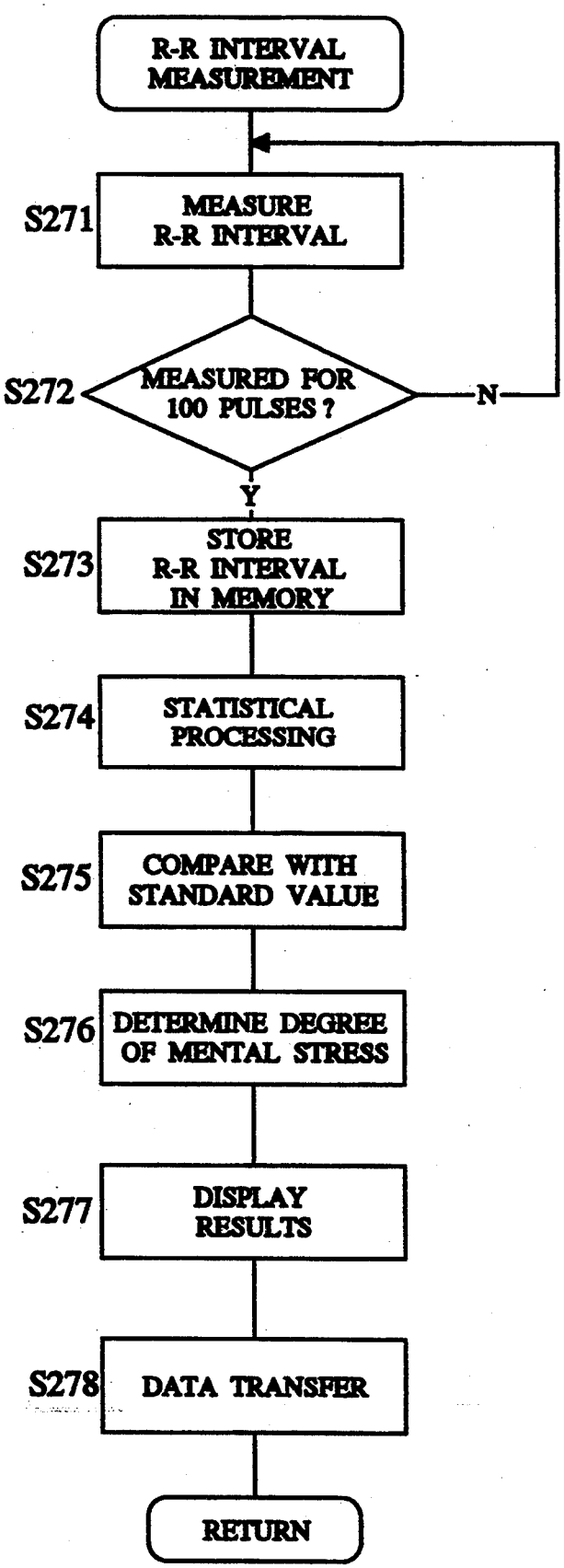
Figure 35:
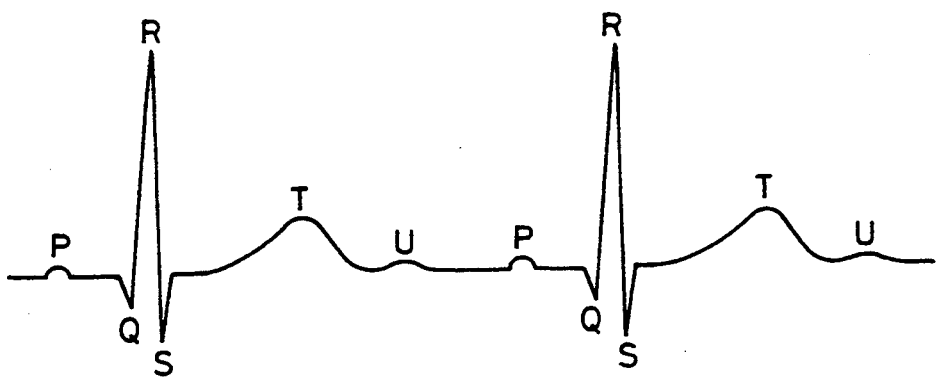
FIG. 35 is a graph schematically showing part of electrocardiogram.
Figure 36:
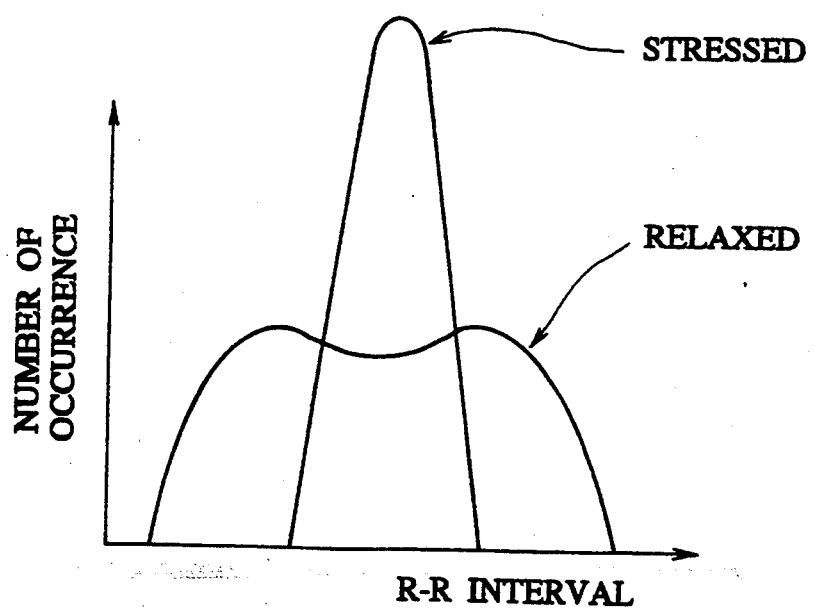
FIG. 36 is a histogram wherein data of R—R interval of electrocardiogram is schematically plotted to show the degree of mental stress.

As the displacement measuring routine (S234) is completed, a determination is made as to whether the bath room conditions has already been preset (S235). Since the bath room conditions presetting at S223 would not have been effected when the bather entered the bath room by striding over the scale 21 situated at the entrance, presetting is done at S236. Then the aeration nozzle units 154 and the pump of the jet blow system are operated (S237–238) and the R—R interval of electrocardiogram is measured Measurement of the R—R interval of electrocardiogram (S239) is effected as shown in the flowchart of FIG. 34. First, the microcomputer 45 monitors the output from the electrodes 173 of electrocardiograph to detect the R—R interval of electrocardiogram (S271). As shown schematically in FIG. 35, the R-pulse of electrocardiogram exhibits a salient peak and, for this reason, can be adequately detected by the electrodes 173 affixed to the bath tub 150. It is known that the interval between adjacent R-pulses is related to the mental stress of a human. It is believed that, in the histogram as shown in the graph of FIG. 36, the degree of mental stress is high when the width of deviation value is narrow, while a person is relaxed when the width is wide. The measurement of the R—R interval is carried out for 100 pulses (S272) and the resulting data is stored in the memory (S273). Then the data is statistically processed to derive the histogram shown in FIG. 36 (S274) and, by comparing with a standard pattern (S275), the degree of mental stress is determined (S276). The results are displayed on the LCD 47 (S277) and are transmitted to the controller 20 (S278).

After the R—R interval of electrocardiogram is measured in the this manner, the bath room conditions are modified at S240 in accordance with the newly acquired data to alter the intensity of jet blow and other conditions such that the degree of massaging effect is commensurate with the degree of fatigue of the bather. In this manner, a high degree of health care is performed thereby providing an accelerated recovery from exhaustion. The microcomputer 45 periodically checks the signals from the level sensor 170 to see if the water level resumes the initial value (S241) and repeats measurement of R—R interval and resetting of the bath room conditions unless initial level is sensed. As the level returns to the initial level, it is judged that the bather has left the bath tub, so that the jet blow system is turned off (S242). When the photoelectric sensor 172 no longer senses the presence of bather in the bath room (S243), the microcomputer 45 turns off the mist sprayer (S244).

Figure 37:
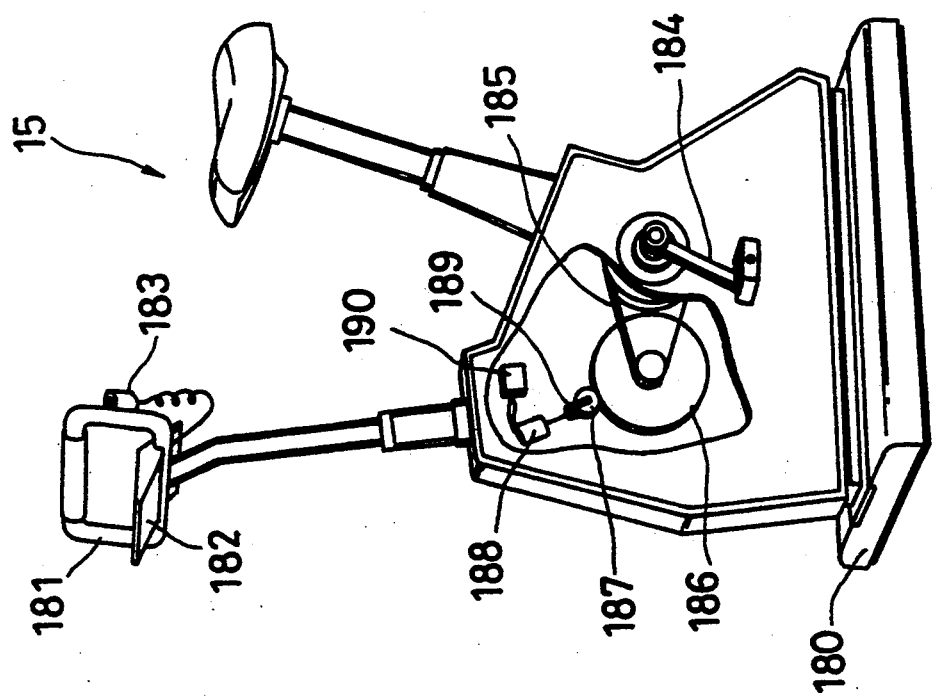
FIG. 37 is a perspective view, partly cut out, of an ergometer incorporated in the health care and monitoring system of the invention.

Referring to FIG. 37, the ergometer 15 is generally used in conjunction with indoor exercise for the maintenance of health and for the measurement of the physical strength of individuals. In the illustrated embodiment, however, the ergometer is further adapted to measure the artery blood pressure, pulse rate and the body weight for use as the vital information and to detect the body weight for use as the individuals recognition parameter. Detection of weight is carried out passively. The ergometer 15 is further designed such that the load of exercise is controlled in accordance with the vital information received from the controller 20 as well as the information acquired by itself. In the embodiment shown, the ergometer 15 is adapted to vary the load of exercise based on the body fat content detected by the toilet system 12 and transmitted from the controller 20.

To this end, the ergometer 15 has at its base a built-in weight detector 180 for detecting the user's weight as the individuals recognition parameter as well as the vital information. The microcomputer 48 and a control unit of a digital sphygmomanometer are arranged in a control box 182 mounted to a handle 181. A measuring finger cuff 183 of the sphygmomanometer is detachably affixed to the handle 181 to permit the user to wear it for monitoring of the artery blood pressure and pulse rate during exercise. Preferably, the digital sphygmomanometer HEM801 described before may also be used in the ergometer 15. The control box 182 is provided with the LCD 50 adapted to display the blood pressure and pulse rate during exercise. The control box 182 is also provided with a conventional manual input switches, not shown, in order to permit the user to select a predetermined simplified exercise program at its option.

Figure 38:
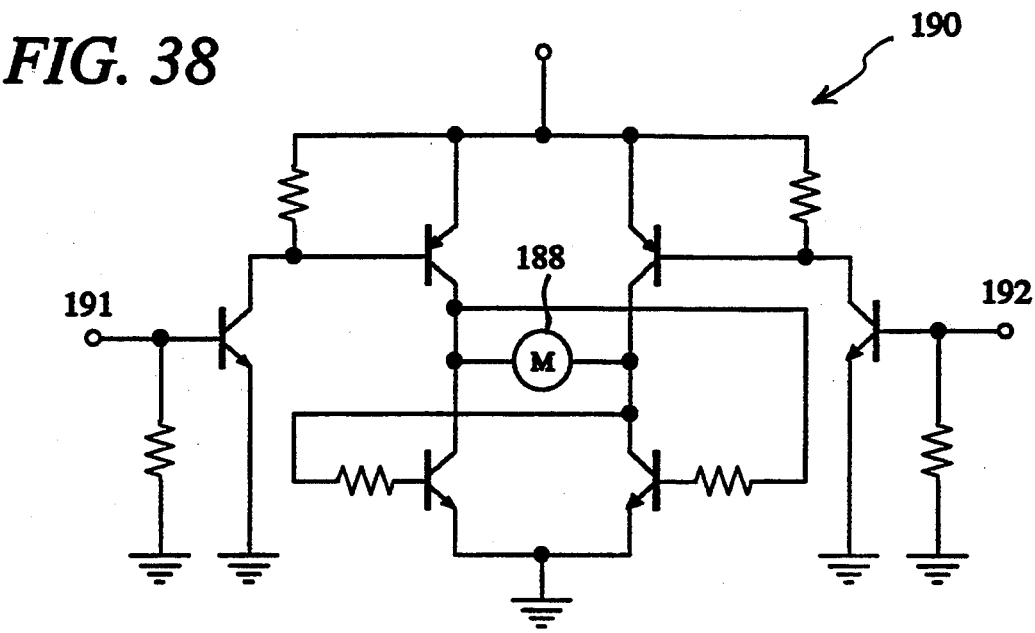
FIG. 38 is a wiring diagram of a driver circuit of a linear motor used for controlling the load of exercise of the ergometer shown in FIG. 37.
Figure 39:
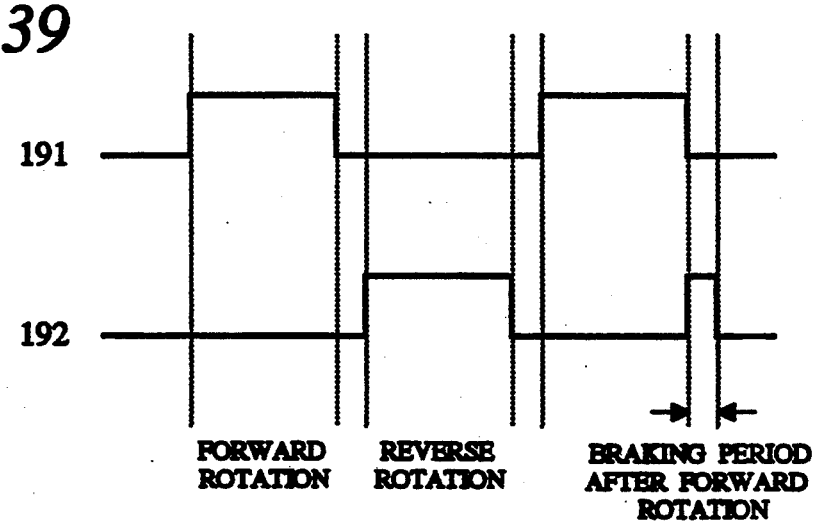
FIG. 39 is a timing chart showing the operation of the driver circuit shown in FIG. 38.
Figure 40:
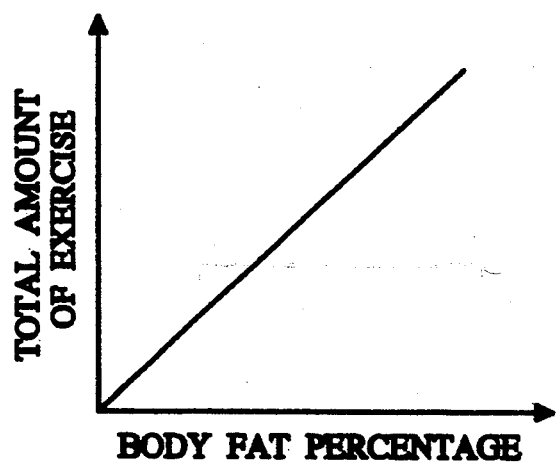
FIG. 40 is a graph showing an example of exercise load control.

The ergometer 15 is designed to simulate a bicycle and has a pedalled crank 184 to rotate a wheel 186 through a belt drive 185. The wheel 186 is in contact with a rotatable friction roller 187, the contact pressure of which is controlled by a linear DC motor 188 to vary the rotational frictional resistance against the wheel 186 thereby to control the load of exercise. To this end, a forked support 189 rotatably supporting the friction roller 187 is connected to the output shaft of the linear DC motor 188 in such a manner that, by rotating the DC motor 188 in one direction the frictional resistance applied to the rotary wheel 186 is increased, and vise versa. The linear DC motor 188 is powered by a driver circuit 190 which is controlled by the microcomputer 48. An example of the driver circuit 190 is shown in FIG. 38. The driver circuit 190 is of a well known arrangement and is designed such that the motor 188 is rotated in the forward direction by application of a voltage to the first terminal 191 but is rotated in the reverse direction as the voltage is applied to the second terminal 192, as shown in FIG. 39. The DC motor 188 may be controlled, for example, in such a manner that the total amount of exercise which is the product of imposed frictional load multiplied by time is linearly increased in proportion to the body fat percentage of the user as illustrated in FIG. 40.

Figure 41:
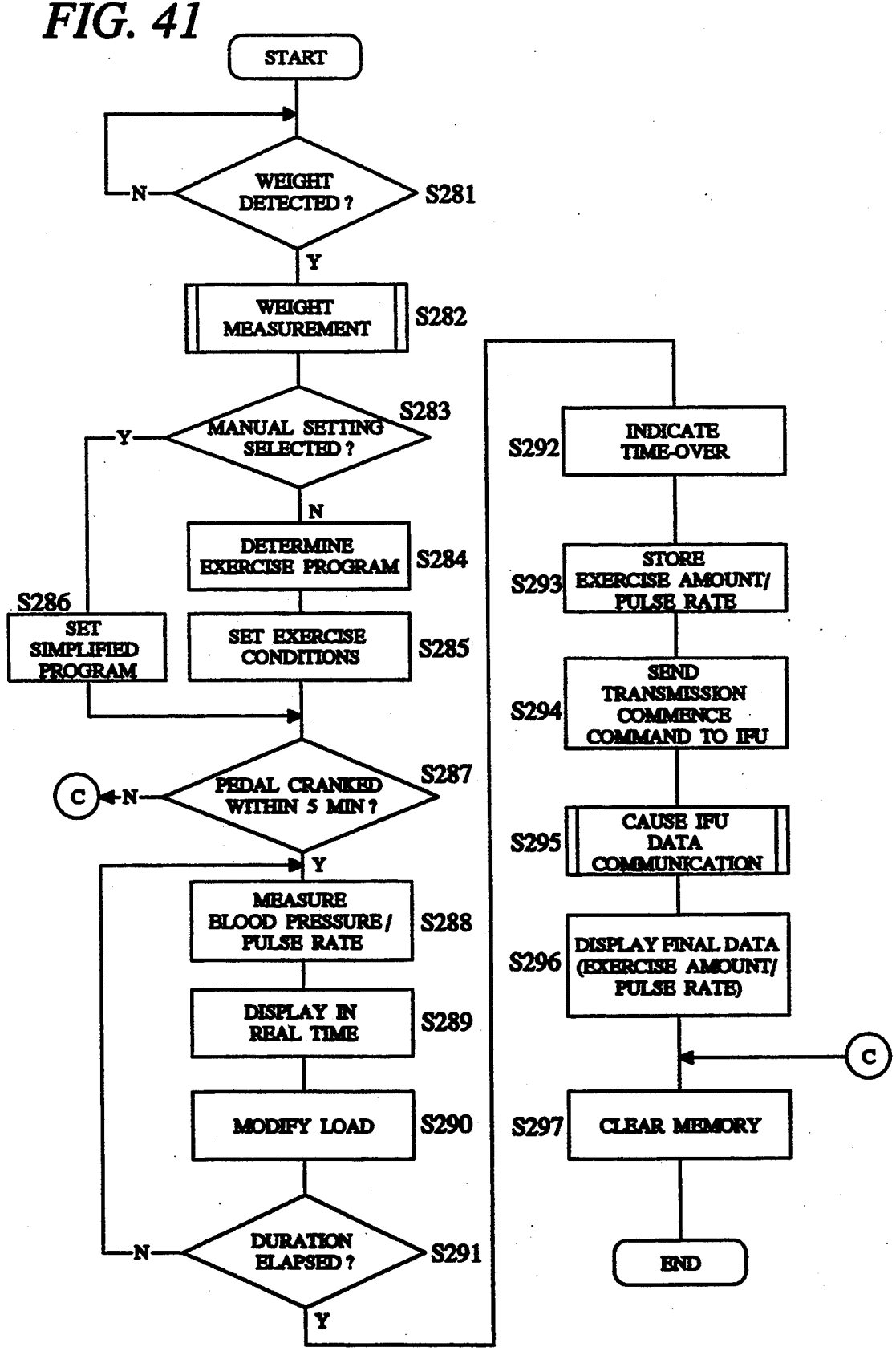
FIG. 41 is a flowchart showing the operation of a microcomputer associated with the ergometer shown in FIG. 37.

Function of the ergometer 15 will be described in conjunction with operation of the microcomputer 48 thereof shown in the flowchart of FIG. 41. As the weight detector 180 senses the user (S281), the weight measurement and information communication routine (S282) is carried out in a manner similar to the body weight measurement routine (S151-157) described before with reference to FIG. 21. Thus, upon receipt of the detected body weight data from the ergometer 15, the controller 20 identifies the appliance and the individual (see S122-123 of FIG. 7) and looks up column VI of the table of FIG. 3 to furnish the ergometer 15 with the vital data concerning the body fat content, artery blood pressure and pulse rate, and basal body temperature of the particular individual. The body fat data transmitted to the ergometer 15 is the one that was passively detected by the toilet system 12 as described before, while the basal body temperature is the one that was also passively measured by the bed system 13. After receiving the data, the microcomputer 48 determines at S283 if the predetermined simplified exercise program according to the manual input switches of the control box 182 is selected and, if so, then sets a load of exercise dictated by the simplified program menu (S286). The simplified program menu may be such that one of three predetermined different levels of frictional load, say, heavy, moderate and light, can be selected at the option of the user to permit the user to exercise against the selected invariable load. If the simplified exercise program is not selected, the microcomputer 48 determines exercise program depending on the nature of the vital information received from the controller 20 (S284) and sets the frictional load and duration of exercise (S285). Determination of the exercise program may be made, for example, such that, in the case of exercise by a hypertensive user, the pulse rate during exercise does not exceed one and a half of normal pulse rate. The load of exercise (S285) may be set according to the body fat percentage as described before with reference to FIG. 40. The microcomputer 48 then determines whether the pedal is cranked within five minutes from weight detection (S287) and, if not cranked, skips to S297 to clear memory and terminate the main routine. If cranking of the pedal is detected, the artery blood pressure and pulse rate are measured based on the signals from the measuring cuff 183 (S288) and the resulting data is displayed for the user on the LCD 50 in a real time fashion (S289). The load of exercise is modified in accordance with the detected artery blood pressure and pulse rate (S290). The microcomputer 48 cyclically monitors the time to see if the preset duration of exercise has elapsed (S291) and repeats the blood pressure and pulse rate measurement (S288) and load modification (S290) until the preset duration elapses. Upon lapse of time, an indication to that extent is displayed on the LCD50 (S292) and the amount of exercise (i.e., load multiplied by duration of exercise) and the pulse rate are temporally stored in the memory (S293). Then a transmission commence command is forwarded to the IFU 25 (S294) to cause it to commence communication with the IFU 26 of the controller 20 (S295). Communication at S295 is performed in a manner similar to that described before in conjunction with the communication routine (S156) of the IFU 22 of the toilet system 12 with reference to FIG. 21. As a result, the body weight, amount of exercise, artery blood pressure and pulse rate measured and detected at the ergometer 15 are stored as the vital information in the memory of the controller 20. The microcomputer 48 thereafter causes the final data (the amount of exercise and the pulse rate) to be displayed on the LCD 50 (S296) and clears its memory (S297).

In this manner, the ergometer 15 is operated to initially select the program of exercise in accordance with the vital information obtained at the other household appliances, such as the body fat content and artery blood pressure measured at the toilet system or the body temperature detected at the bed, and is adapted to control and modify during exercise the initial conditions based on the pulse rate measured in a real time fashion at the ergometer.

Figure 42:
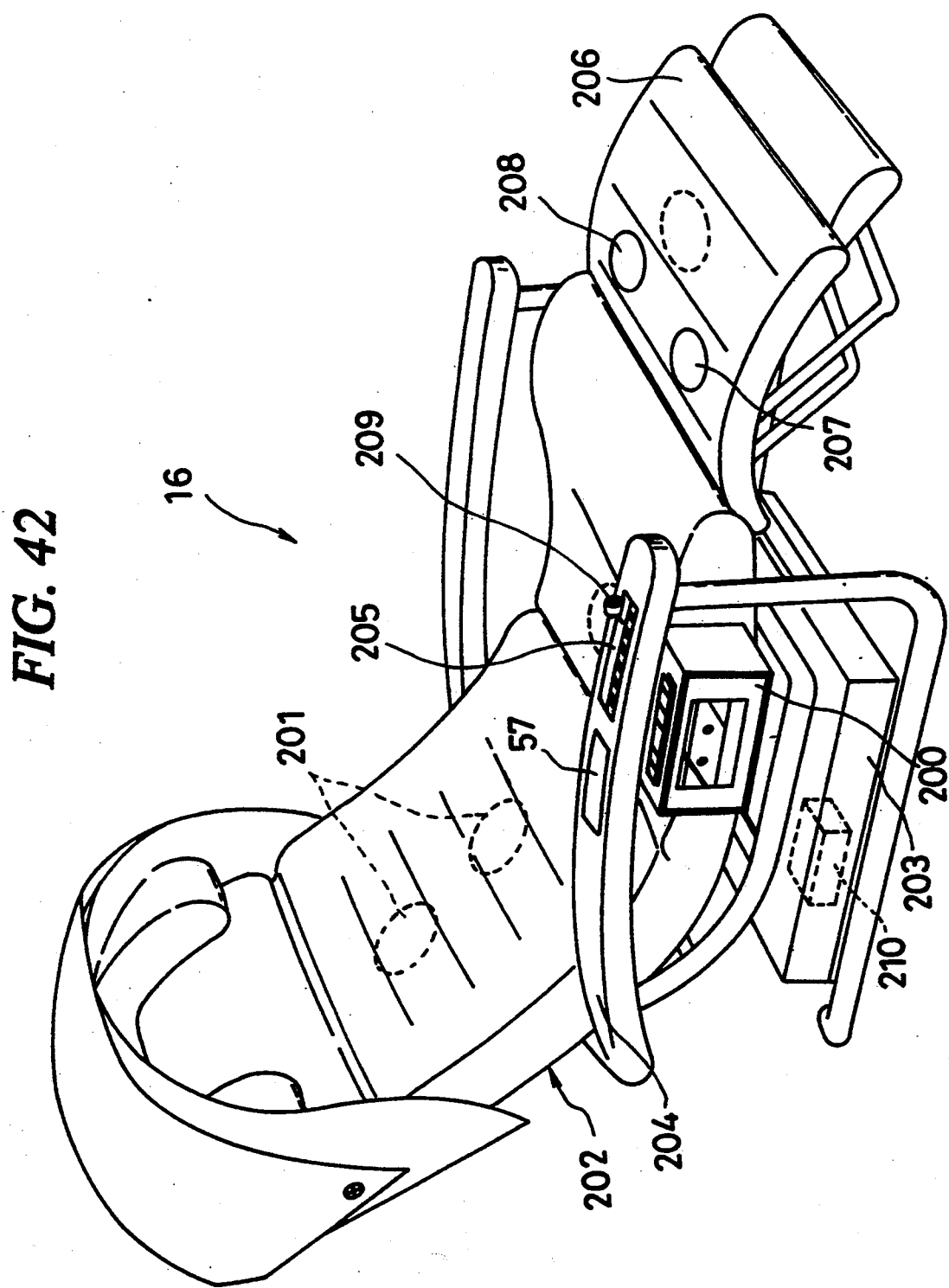
FIG. 42 is a perspective view of an easy chair usable in the health care and monitoring system of the invention.

In FIG. 42, there is shown an easy chair 16 which may be suitably used in the networked health care system of the invention. The easy chair 16 may be made by modifying the chair "Refresh-1" available on the market from Body Sonic Co., Ltd., of Tokyo, Japan, and incorporating a plurality of built-in vibratory transducers 201 driven by an audio system 200 to produce low frequency vibrations for providing massaging effect.

For the purposes of the present invention, the main body 202 of the chair 16 is mounted on a weight detector 203 to measure the body weight of the user passively in response to the user sitting on the chair. The output of the weight detector 203 is sent to the microcomputer 55. One of armrests 204 is provided with a measuring electrode of electrocardiograph so that the right arm of the user is brought in contact therewith. Footrest 206 is provided with a reference electrode 207 and a measuring electrode 208 to ensure that the right and left lower limbs of the user are contacted therewith, respectively. The outputs of these electrodes are forwarded to the microcomputer 55 for electrocardiography according to the second lead method. The armrest 204 is also provided with the LCD 57 and a measuring finger cuff 209 of a conventional digital sphygmomanometer of the class mentioned before. The control unit of the sphygmomanometer, the microcomputer 55 and the IFU 27 are disposed in a control box 210 arranged in the weight detector, with the control unit of the sphygmomanometer being connected to the microcomputer 55. The microcomputer 55, in turn, is operatively connected to the audio system 200 to control the degree of massaging effect provided by the transducers 201.

Figure 43:
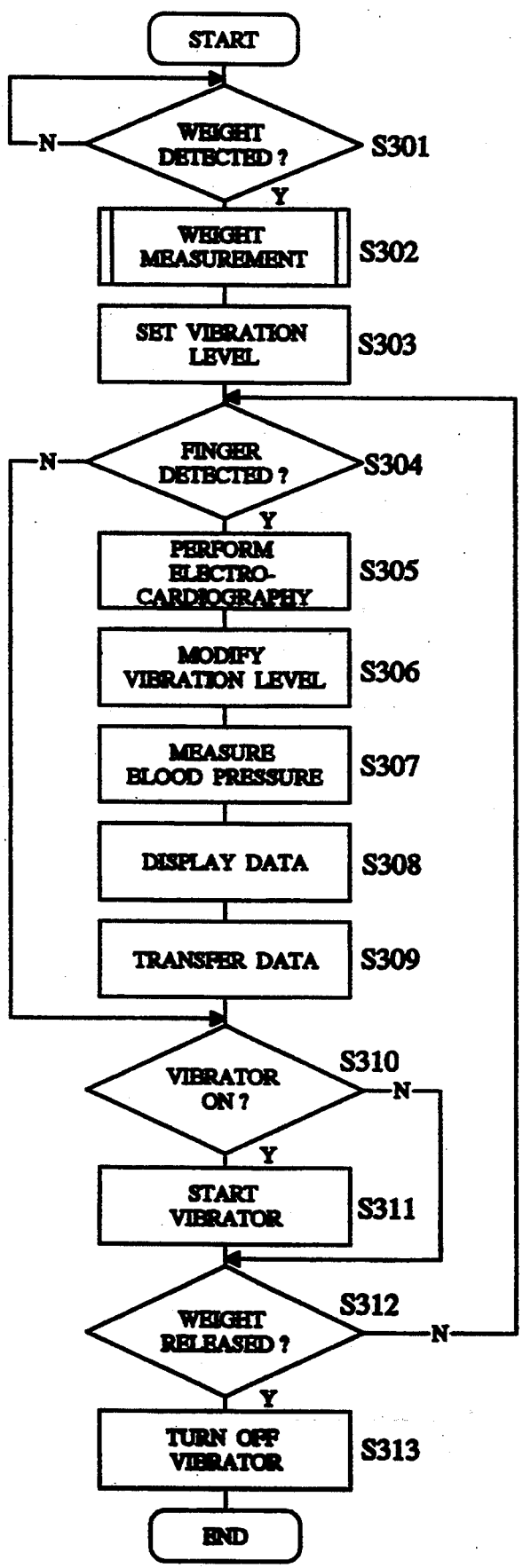
FIG. 43 is a flowchart showing the operation of a microcomputer associated with the easy chair shown in FIG. 42.

Operation of the easy chair 16 will be described with reference to the flowchart of FIG. 43. As the weight detector 203 senses the weight of the user (S301), the weight measurement and information communication routine (S302) is carried out in a manner similar to steps S151-157 described hereinbefore with reference to the flowchart of FIG. 21. Upon receiving the body weight data from the easy chair 16, the controller 20 recognizes the particular appliance and the particular individual (S122-123 of FIG. 7) and looks up column VI of FIG. 3 to furnish the easy chair 16 with the data relating to the R—R interval of electrocardiogram of the particular individual. The R—R interval data transmitted to the easy chair 16 is the one which has been detected by the bath system 14 and stored in the controller 20 as described before. As the R—R interval of electrocardiogram represents the degree of mental stress as referred-to before, the microcomputer 55 sets the level of vibration of vibratory transducers 201 based on the R—R interval data (S303). Then the microcomputer 55 checks the signals from the cuff 209 to see if the user has worn the measuring cuff (S304). In this regard, it will be noted that, in the easy chair 16 also, the user must wear the finger cuff 209 in order to enable measurement of artery blood pressure, whereby a positive intervention is required on the part of the user. Furthermore, even though the arm of the user will necessarily be brought in contact with the measuring electrode 205 as a result of the user engaging the finger thereof into the cuff 209, other electrodes 207 and 208 must intentionally be engaged with the lower limbs. This can be made relatively readily when the user wears a bathrobe. If the user does not engage the cuff 209, the microcomputer 55 skips to S310. If the cuff is engaged, the microcomputer 55 operates the electrocardiograph (S305), adjusts the vibration level of the transducers 201 according to the newly measured R—R interval (S306), permits artery blood pressure measurement (S307), displays the resulting data on the LCD 57, and transfers the data to the controller 20 (S309). Then the microcomputer 55 checks the audio system 200 to determine if the switch thereof is turned on (S310) and, if this is the case, operates the audio system (S311). The microcomputer 55 monitors the output of the weight detector 203 (S312) and repeats the foregoing measurement and control S304–311 as long as the weight is detected. As the weight is no longer sensed, it is judged that the use of the easy chair 16 is terminated so that the audio system 200 is turned off (S313).

Figure 44:
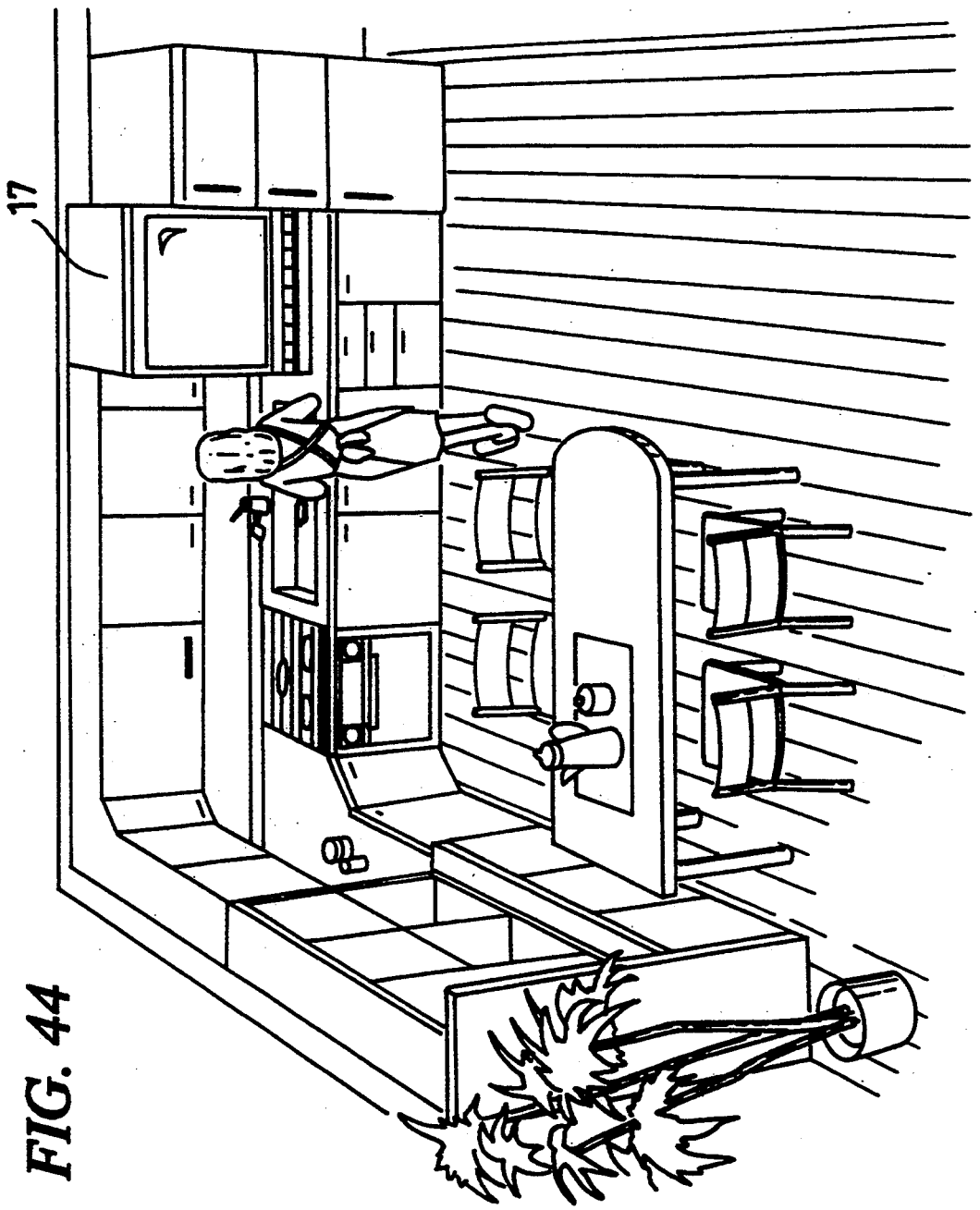
FIG. 44 is a perspective view of a menu processor as arranged in a kitchen for use with the health care and monitoring system of the invention.

FIG. 44 illustrates the menu processor 17 as installed in a kitchen of the residence. As shown in FIG. 4, the menu processor 17 may comprise a general purpose digital personal computer 58 having the keyboard 59 and the CRT 61 and loaded with the conventional menu processing and formulation program available on the market. The data base forming part of the program is stored in the hard-disc drive 60.

Figure 45:
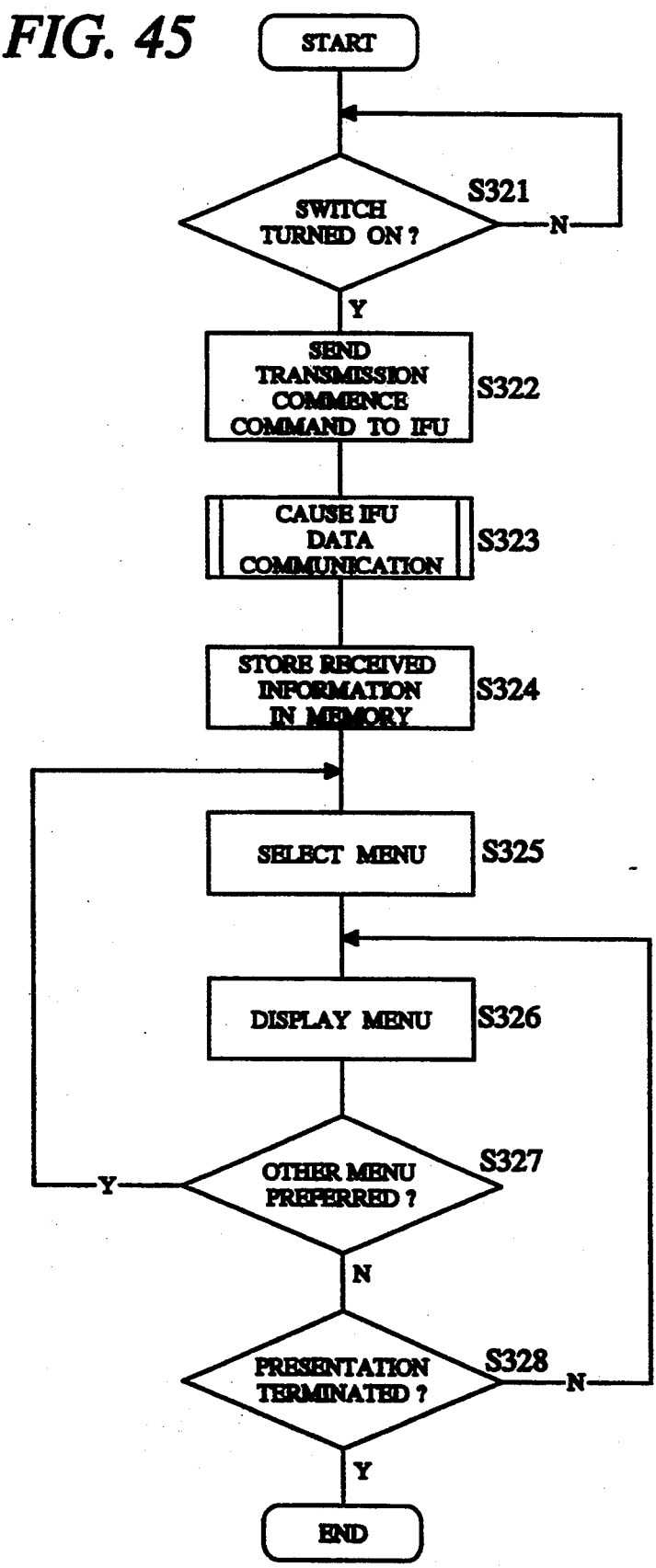
FIG. 45 is a flowchart showing the operation of the menu processor shown in FIG. 44.

Referring to the flowchart of FIG. 45 wherein operation of the computer 58 is shown, function of the menu processor 17 will be described. As a switch for the menu processor 17 is turned on (S321), a transmission commence command is sent to the IFU 28 (S322) to cause it to perform data communication (S323) with the controller 20 via the coaxial cable 11 as described before. Data communication is carried out such that the ID number of the individual for which menu is to be provided is transmitted from the IFU 28 of the menu processor 17 to the controller 20, which sends back to the menu processor 17 the vital information as indicated in column VI of the table of FIG. 3 relative to the subject individual. As described before, the data of urinalysis and body fat content will be the one detected by the toilet system 12, with the amount of exercise being the one derived by the ergometer 15. The computer 58 stores the data received from the controller 20 in the memory thereof (S324), selects a proper menu (S325) and cause the menu displayed on the CRT 61 (S326). If the operator prefers a menu other than the displayed (S327), selection and display are repeated insofar as the operator desires (S328). The menu forming program may be programmed in such a manner that, in the case of a diabetic individual, for example, a series of minus suitable for the alimentary therapy of diabetes are displayed in sequence to permit the operator to determine a desirable one.

Figure 46:
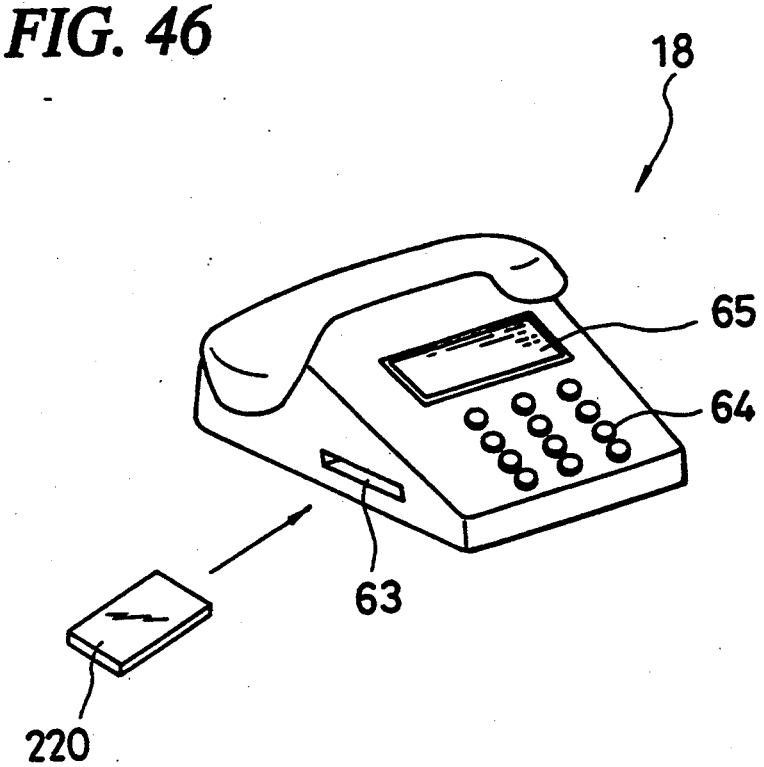
FIG. 46 is a perspective view showing a telephone usable in the health care and monitoring system of the invention.

FIG. 46 illustrates the telephone 18, with MODEM and IC card read and write device, which may be connected to the networked system of the invention. Referring to FIG. 46 in conjunction with FIG. 4, the telephone 18 is provided with the MODEM 66 adapted to transmit the vital information obtained in the network system 10 via public telecommunications lines to the host computer 67 installed in hospital, medical clinic, centralized health monitoring institution, or life-care center. As is well known, the IC card read and write device 63 is adapted to read and write an information into an IC card 220. The IC card 220 maybe used to record the vital information acquired in the network system 10 to bring it to the hospital, and the like. The IC card 220 is also usable to record the information obtained at offices, hospitals and sports institutions and to bring it home for storage in the controller 20 of the network system 10. Further, auto-dialing program may be written in the IC card 220 to facilitate data transmission.

Figure 47:
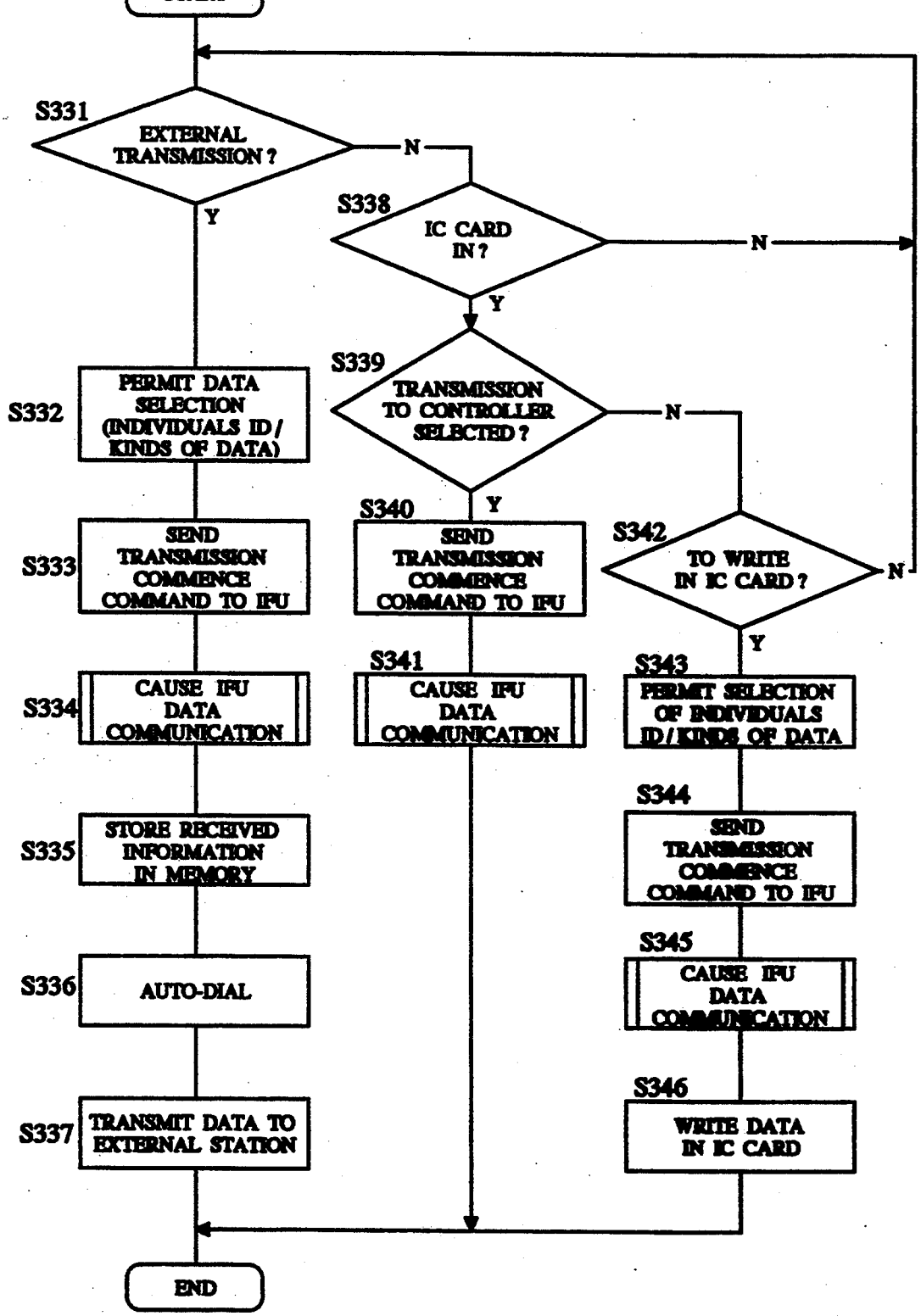
FIG. 47 is a flowchart showing the operation of a microcomputer of the telephone shown in FIG. 46.

For these purposes, the microcomputer 62 of the telephone 18 may be programmed to operate as shown in the flowchart of FIG. 47. Referring thereto, the microcomputer 62 first determines at S331 if the vital data is to be transmitted via the MODEM 66 to an external station. Generally, the microcomputer 62 performs sequences S332–337 if the vital data derived in the network system 10 is to be transmitted to the external station, or sequences S340–341 if the vital data acquired externally to the system 10 and recorded in the IC card 220 is to be transferred to the controller 20 of the system 10, or sequences S343–346 if the information obtained in the system 10 must be written in the IC card 220 for being brought to the hospital and the like.

More specifically, if the vital data is to be transmitted via the MODEM 66 to the external station, the operator is permitted at S332 to select the data to be transmitted by inputting the individuals ID number and the kind of data through the ten keys 64. Then a transmission commence command is sent to the IFU 29 (S333) to cause communication to be performed between the IFU 29 of the telephone 18 and the IFU 26 of the controller 20 (S334). Data communication at S334 is also carried out in a manner similar to the communication routine S156 (FIG. 21) described before in conjunction with the IFU 22 of the toilet system 12. The microcomputer 62 then temporarily stores the data received from the controller 20 in its memory (S335) and performs auto-dialing (S336) to cause the data to be transmitted toward the external station (S337).

If at decision S331 it is determined that data transmission to the external station is not selected, determination is then made at S338 to see if the IC card 220 is inserted into the read and write device 63. If inserted, it is then determined whether data transfer to the controller 20 is selected (S339) and, if so, a transmission commence command is sent to the IFU 29 (S340) to cause data communication between the IFU 29 of the telephone 18 and the IFU 26 of the controller 20 in a manner described before (S341). Accordingly, the data recorded in the IC card 220 will be transferred to the controller 20 for storage in its memory 54.

If at decision S339 it is determined that data transfer to the controller 20 is not selected, it is then determined at S342 whether writing of data into the IC card 220 is instructed. If instructed, the operator is permitted to select the individuals ID number and the kind of data (S343) and a transmission commence command is then sent to the IFU 29 (S344) so that data communication is carried out between the IFU 29 of the telephone 18 and the IFU 26 of the controller 20 (S345). As a result, the microcomputer 62 will acquire the vital information stored in the memory of the controller 20. Finally, the received information is written in the IC card 220 (S346).

The monitor 19 may be comprised of the general purpose digital personal computer 69, the keyboard 70 and the CRT 71 as described before with reference to FIG. 4.

Figure 48:
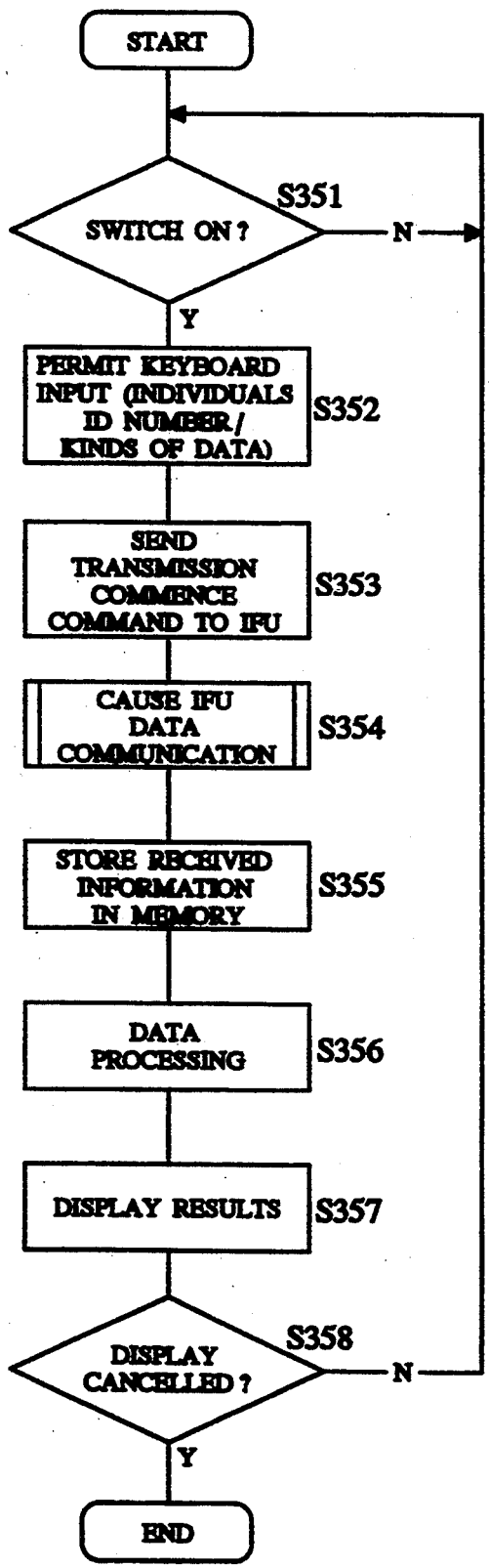
FIG. 48 is a flowchart showing the operation of a video monitor usable in the health care and monitoring system of the invention.

Operation of the computer 69 of the monitor 19 is shown in the flowchart of FIG. 48. As shown, after detecting that a switch for the monitor is turned on (S351), the operator is allowed to select the individuals ID number and the kind of data using the keyboard 70 (S352) and a transmission commence command is sent to the IFU 30 (S353). This will cause data communication (S354) to be performed between the IFU 30 of the monitor 19 and the IFU 26 of the controller 20 in a manner described before, so that the computer 69 receives from the controller 20 the data as indicated in column VI of the table of FIG. 3. The computer 69 then stores the received data in the memory (S355) and processes the data according to the instructions input through the keyboard 70 (S356) for displaying the results on the CRT 71 (S357). Display is continued unless cancelled (S358).

The networked health care system 10 described hereinbefore with reference to FIGS. 1-46 is of the so-called "centralized" communications network configuration in the sense that the vital information obtained by respective testing and measuring devices associated with the household appliances is forwarded to the controller 20 for storage and control thereby and that any household appliances requiring the stored information are adapted to access the controller 20 for retrieval of the vital information therefrom where required.

Referring now to FIGS. 49-59, the health care system of the "distributed" network configuration according to the invention will be described. As compared with the foregoing centralized network system, the primary topographical difference resides in that the data controller 20 is eliminated from the network topography shown in FIG. 4. For this reason, description of the network topography will not be necessary. In the following description, part and members equivalent to those indicated in FIG. 4 will be referred-to by like reference numerals.

Since the distributed network system is not provided with a data controller, the vital information obtained by respective testing and measuring devices associated with the household appliances of the network must be stored as distributed among respective household appliances. Therefore, those testing and measuring devices and control devices which require the vital information stored in the other appliances for the purposes of achieving their own measuring and health care control functions must access through the network the testing and measuring devices associated with the other appliances in order to retrieve and make use of the information necessary for their functions. In contrast to the centralized networked system wherein the controller 20 is adapted to perform the individuals recognition function as well as the table look-up function (S124 of FIG. 7) so that the physical data necessary for individuals recognition as well as the information listed in column VI of the table of FIG. 3 are stored in the memory of the controller 20, the respective computers associated with the household appliances of the distributed network configuration must perform by themselves the individuals recognition function as well as the table look-up function. Accordingly, in the distributed network configuration, each computer must be adapted to store a relatively large amount of data. Therefore, if the aforementioned M37450 single-chip microcomputers were to be used in the distributed topography as the computers of the devices associated with the household appliances, each computer may preferably be provided with an extended memory, except for the general purpose personal computers forming the menu processor and the video monitor. Furthermore, it is preferable to back up the RAM with an auxiliary non-volatile storage medium such as a harddisc drive to ensure that the data remains stored in the event that electric power to the appliances is turned off.

Figure 49:
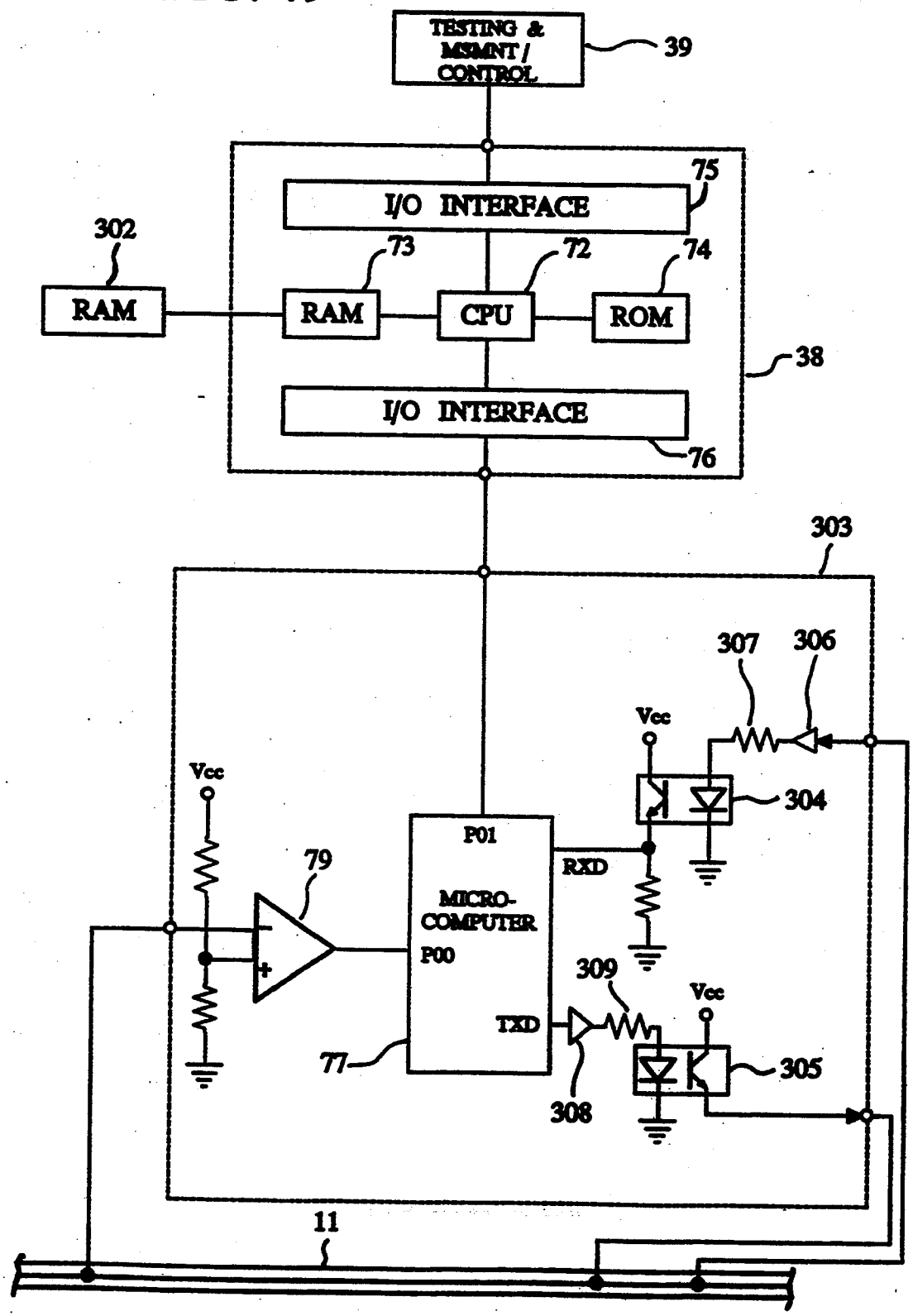
FIG. 49 is a block diagram showing examples of a microcomputer and a communications interface unit which may be suitably used in the health care and monitoring system of the distributed network configuration according to the invention.

In FIG. 49, there is shown an example of hardware structure of the microcomputer 38 for the toilet system 12 and the IFU associated therewith which may be suitably used in the health care and monitoring system according to the distributed network configuration. The microcomputer 38 and the IFU shown in FIG. 49 may be used in place of the microcomputer and the IFU shown in FIG. 5. For this reason, parts and members having functions similar to those of FIG. 5 will be designated in FIG. 49 by like reference numerals and will not be described again. It will also be noted that the hardware structure for the microcomputer and the IFU illustrated in FIG. 49 may be commonly used for the testing and measuring devices and/or the control devices of the other household appliances of the distributed network configuration.

Referring to FIG. 49, each microcomputer, e.g., the microcomputer 38, of the testing and measuring device and/or the control device associated with respective household appliances may similarly comprise the M37450 chip and is provided with a hard-disc drive 302 serving as an auxiliary non-volatile RAM. Each IFU 303 includes the microcomputer 77 which is also implemented by the M37450. To reduce adverse effect due to noises, each IFU 303 includes photocouplers 304 and 305 serving as the receiver and transmitter, respectively. Signals on the coaxial cable 11 are input into the receiver 304 through a buffer 306 and a resistor 307 and is applied to the data receiving terminal RXD of the M37450 microcomputer 77. Signals issued from the data transmission terminal TXD of the M37450 microcomputer 77 are applied through a buffer 308 and a resistor 309 to the driver 305 and are transferred onto the cable 11.

Figure 50:
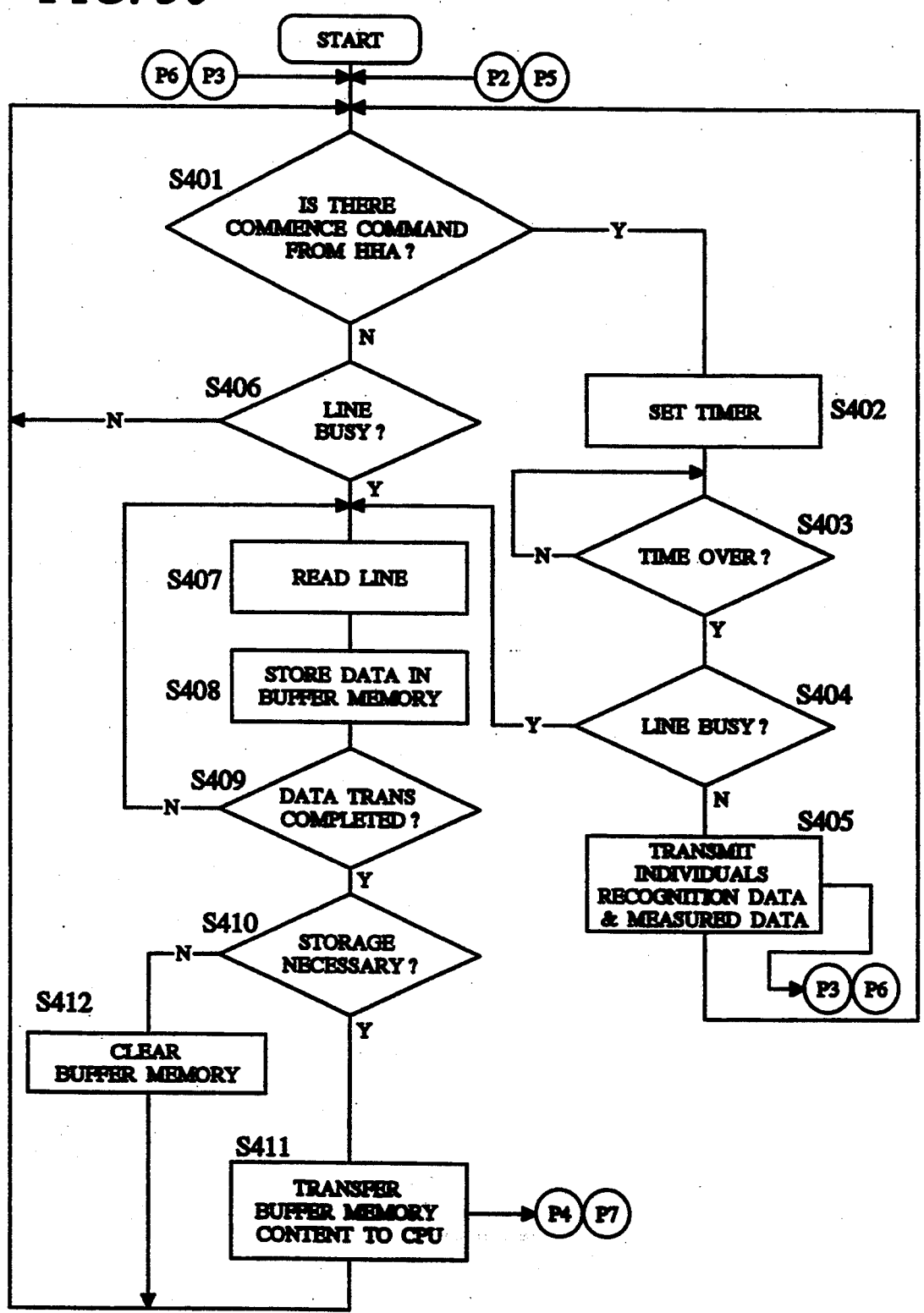
FIG. 50 is a flowchart showing the operation of the interface unit shown in FIG. 49.

Each IFU 303 is generally so programmed as to function as shown in the flowchart of FIG. 50. Thus, each IFU 303 periodically checks the output from the microcomputer 38 associated with the corresponding household appliance to see if a transmission commence command is issued (S401). Upon sensing the transmission commence command from the microcomputer, the IFU 303 sets a timer for a predetermined time period (S402) and, as the time has elapsed (S403), checks whether the coaxial cable 11 is busy (S404). If the line is not busy so that there is no risk of signal collision, transmission of data including the individuals recognition data and the data of measurement is carried out (S405). If the line is busy meaning that the other IFU associated with the other appliances is now involved in data transmission, the IFU 303 goes to read the line (S407). Similar to the centralized network topography described before, the set period of timer may be varied from IFU to IFU so that different IFU's are discriminated in the order of priority of transmission.

If at decision S401 it is determined that a transmission commence command is not issued from the corresponding microcomputer 38, the IFU 303 monitors the line to see if it is busy and stands by for reception of signals transmitted from the other IFU (S406). If the line becomes busy due to transmission from the other IFU, the line is read (S407) and the data is stored in the buffer memory (S408). As data transfer is completed (S409), the IFU 303 causes the corresponding microcomputer 38 to determine if the received data is to be stored in the memory thereof (S410). This determination may be done by causing the microcomputer 38 to look up the information listed in column VI of the table of FIG. 3. To this end, the information contained in column VI of FIG. 3 may preliminarily be stored in the auxiliary RAM 302 of the microcomputer 38 according to the nature of the corresponding appliance. If storage is unnecessary, the buffer memory is cleared (S412). If storage is otherwise necessary, the data is transferred to the corresponding computer for storage in the memory 302 thereof (S411).

Figure 51:
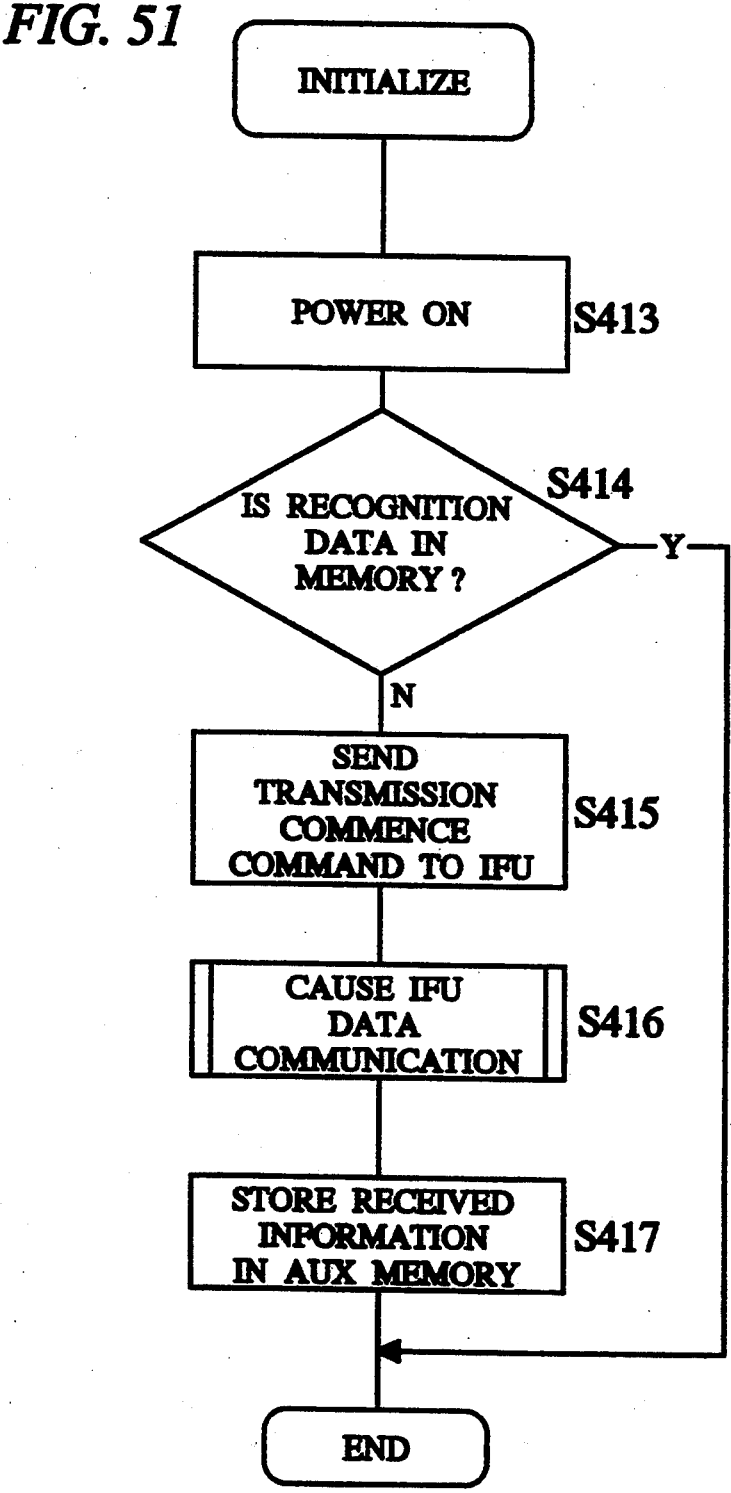
FIG. 51 is a flowchart showing the initialize routine of the microcomputer shown in FIG. 49.

Since the distributed network system is not provided with a data controller for the centralized storage of data as mentioned before, the individuals recognition data, including the body weight, stature and displacement, necessary for the identification of a particular individual must preliminarily be stored for all the prospective members of the family in at least one memory of the computers of the testing and measuring devices and/or control devices associated with the household appliances of the network. Such individuals recognition data may be input prior to use of the system in any one appliance, such as the toilet system 12, by operating the input device therefor. When the other appliance in the network is used for the first time, the computer of the measuring and/or control device of such other appliance must first access through the network the computer already having the individuals recognition data to obtain therefrom the data necessary for individuals identification. To this end, an initializing routine shown in the flowchart of FIG. 51 is performed by each of the computers of the testing and measuring devices and/or control devices of respective household appliances whenever the power is turned on. Referring to FIG. 51, as the power is turned on (S413), each computer checks the corresponding RAM 302 to see if the individuals recognition data is already in memory (S414). If this is the case, the initialize routine is terminated. If the data under question is not stored, a transmission commence command is sent to the corresponding IFU (S415) to cause data communication between that IFU and the IFU's of the other computers of the testing and measuring devices and/or control devices of other household appliances in the network (S416). The individuals recognition data thus acquired from the other computers is stored in the RAM 302 of the corresponding computer (S417).

Referring next to the flowcharts of FIGS. 52-59, the manner of data communication between various devices associated with respective household appliances pertaining to the distributed network system will be described.

Figure 52:
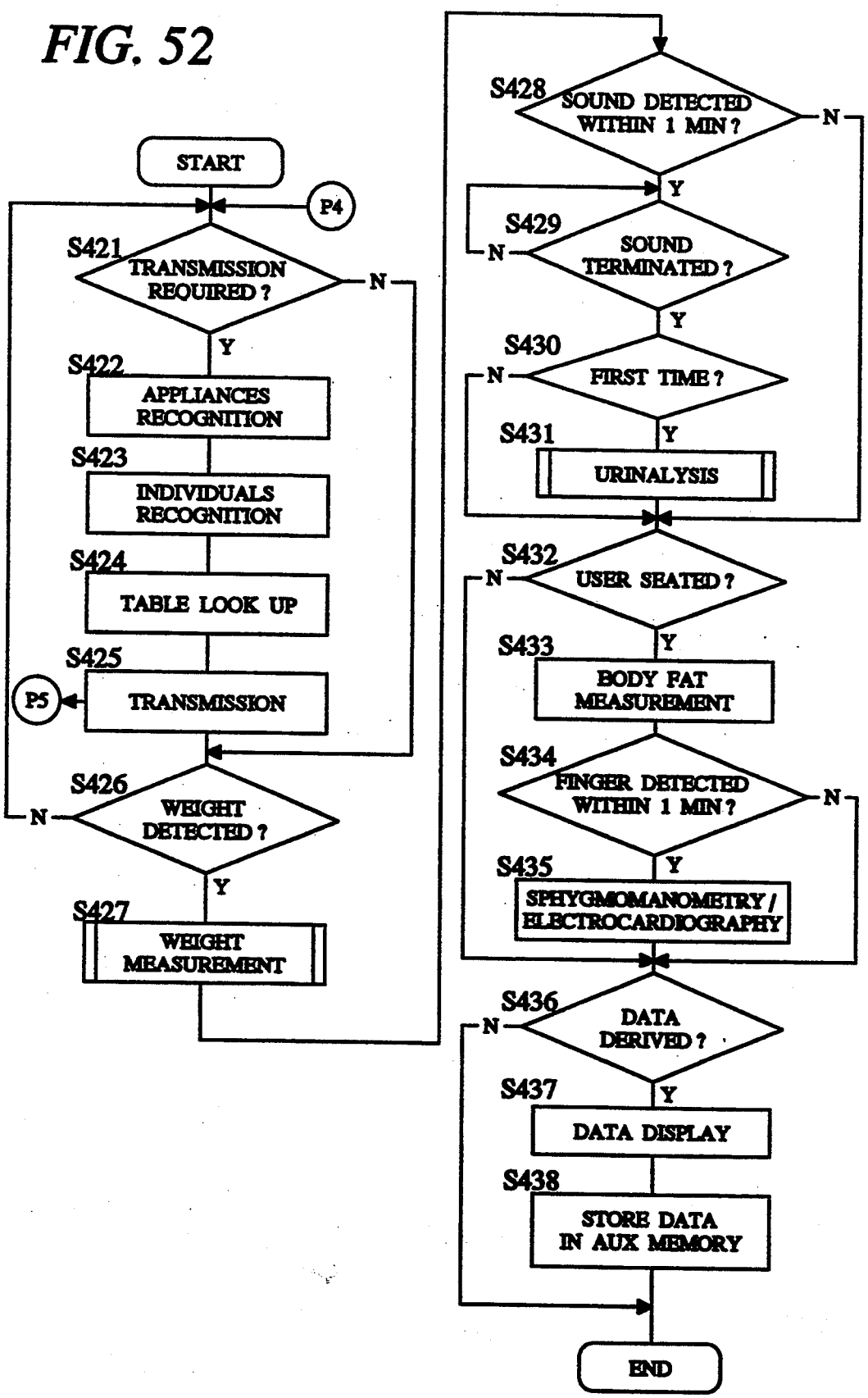
FIGS. 52-59 are flowcharts showing the operation of various household appliances and associated devices incorporated in the health care and monitoring system of the distributed network configuration according to the invention.

The hardware arrangement of the toilet system 12 is similar to that described before with reference to FIGS. 9-19 in connection with the centralized network configuration. The operation of the microcomputer 38 of the toilet system 12 as incorporated in the distributed network topography is shown in FIG. 52. As shown, the microcomputer 38 cyclically monitors if a request-to-send is transmitted from the other appliances (S421). If the request is issued from other appliance, the particular appliance requesting the data transmission is recognized based on the appliances ID number (S422) and the particular individual is identified based on the individuals ID number (S423). In the case that the request-to-send transmitted from the other appliance is not followed by the individuals ID number but only contains the data of the individuals recognition parameter such as the body weight, stature or displacement, the recognition of the individual is performed by comparing the received data with the individuals recognition data of the all the members of the family. Then the table of FIG. 3 is looked up (S424) and the information as listed in column VI of FIG. 3 is transmitted to the other appliance depending on the nature thereof (S425) to permit the other appliance to acquire the data required for its own function. Sequence of events from the detection of bodyweight (S426) to the data display (S437) is similar to the sequence S131-142 described before with reference to FIG. 20 showing the operation in the centralized network system and, therefore, need not be described again. Also, the weight measurement and data communication routine S427 is carried out in a manner similar to that described with reference to FIG. 21 in conjunction with the centralized network configuration. In contrast to the centralized network configuration wherein the acquired data is stored in the controller 20, it will be noted that in the distributed network configuration the data obtained as a result of data communication is stored in the auxiliary memory 302 of the microcomputer 38 of the toilet system 12.

Figure 53:
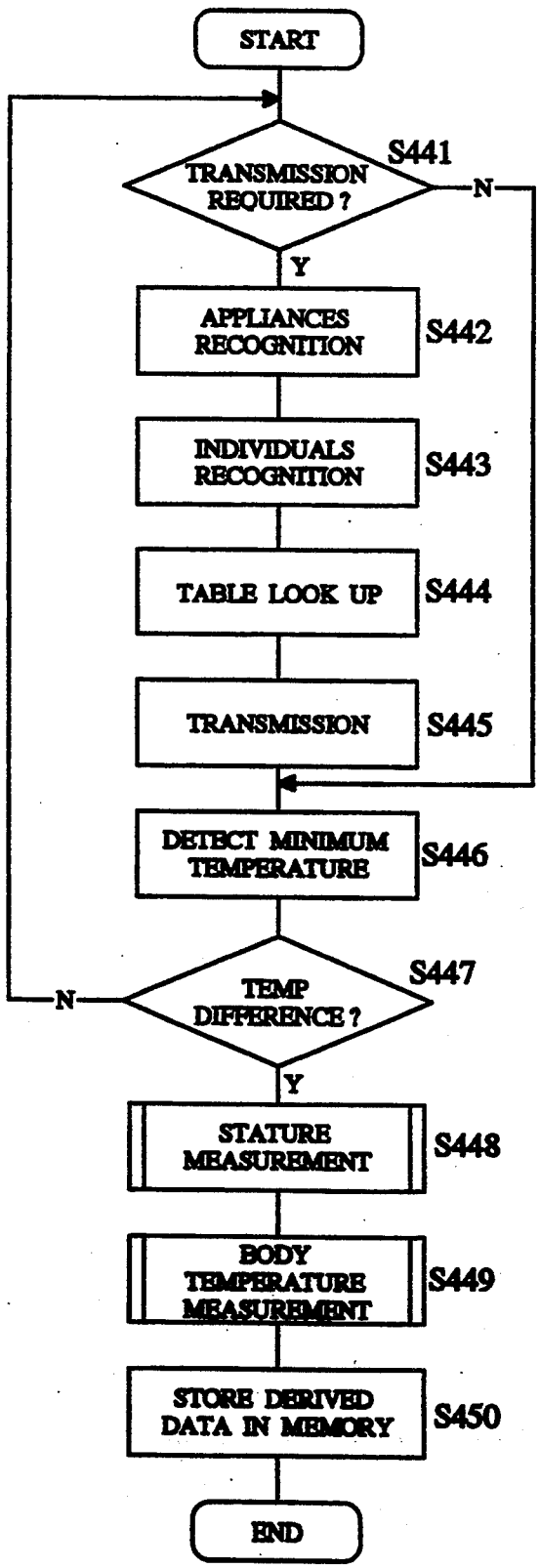
Figure 54:
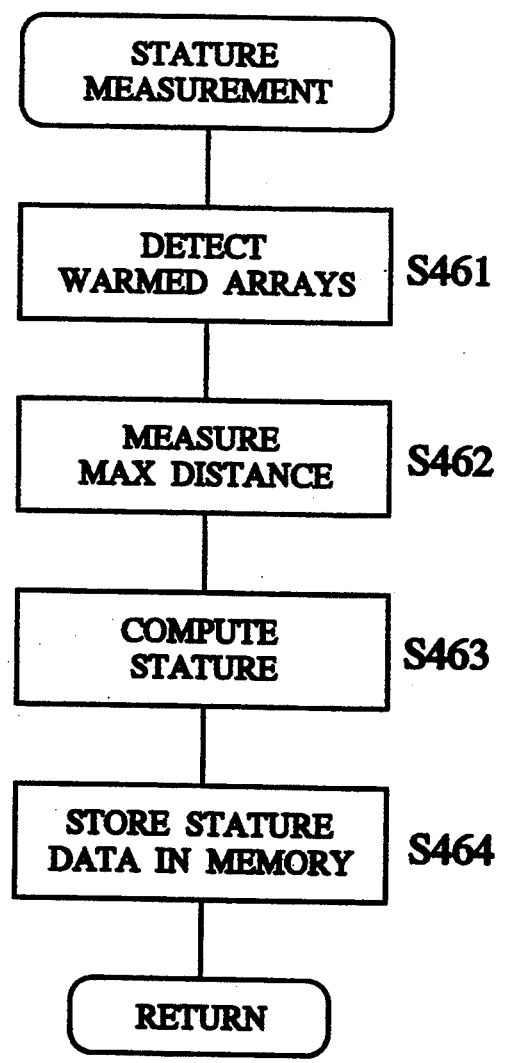

The hardware structure of the bed system 13 is also similar to that described before with reference to FIGS. 23 and 24 in conjunction with the centralized network configuration. In FIG. 53, there is shown the operation of the microcomputer 42 of the bed 13 as arranged in the distributed network topography. Similar to the microcomputer 38 of the toilet system 12, the microcomputer 42 associated with the bed 13 periodically monitors if a request-to-send is transmitted from the other appliances (S441). If the request is made from other appliance, the particular other appliance is recognized based on the appliances ID number (S442) and the particular individual is identified based on the individuals ID number (S443). Then the table of FIG. 3 is looked up (S444) and the information required for the other appliance is transmitted thereto (S445). As a result, the other appliance will receive from the bed 13 the data required for its own function. Thereafter, the minimum temperature in the thermistor matrix is detected (S446) and it is determined if any point in the matrix has a temperature higher than the minimum temperature (S447). If a temperature difference is detected meaning that the bed is now in use, then the stature of the user is measured (S448), the body temperature measured (S449), and the derived data stored in the auxiliary memory (S450). Measurement of the stature S448 is carried out according to the subroutine shown in FIG. 54 such that the thermistor arrays subjected to temperature raise are detected (S461), the maximum longitudinal distance between the warmed arrays measured (S462) to derive the stature of the user (S463), and the resulting stature data stored in the memory (S464).

Measurement of the body temperature S449 is performed as described before with reference to FIG. 27.

Figure 55:
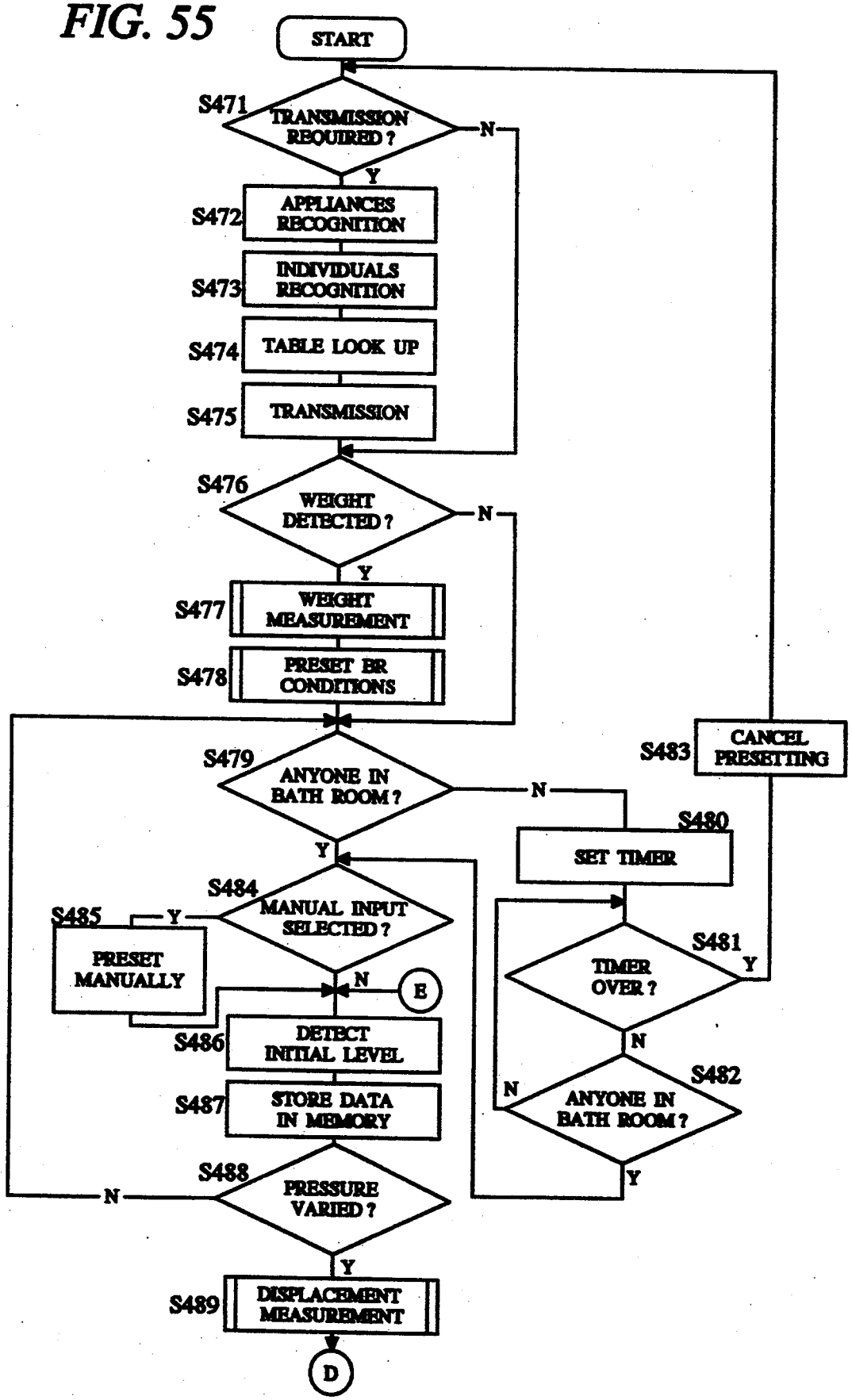
Figure 56:
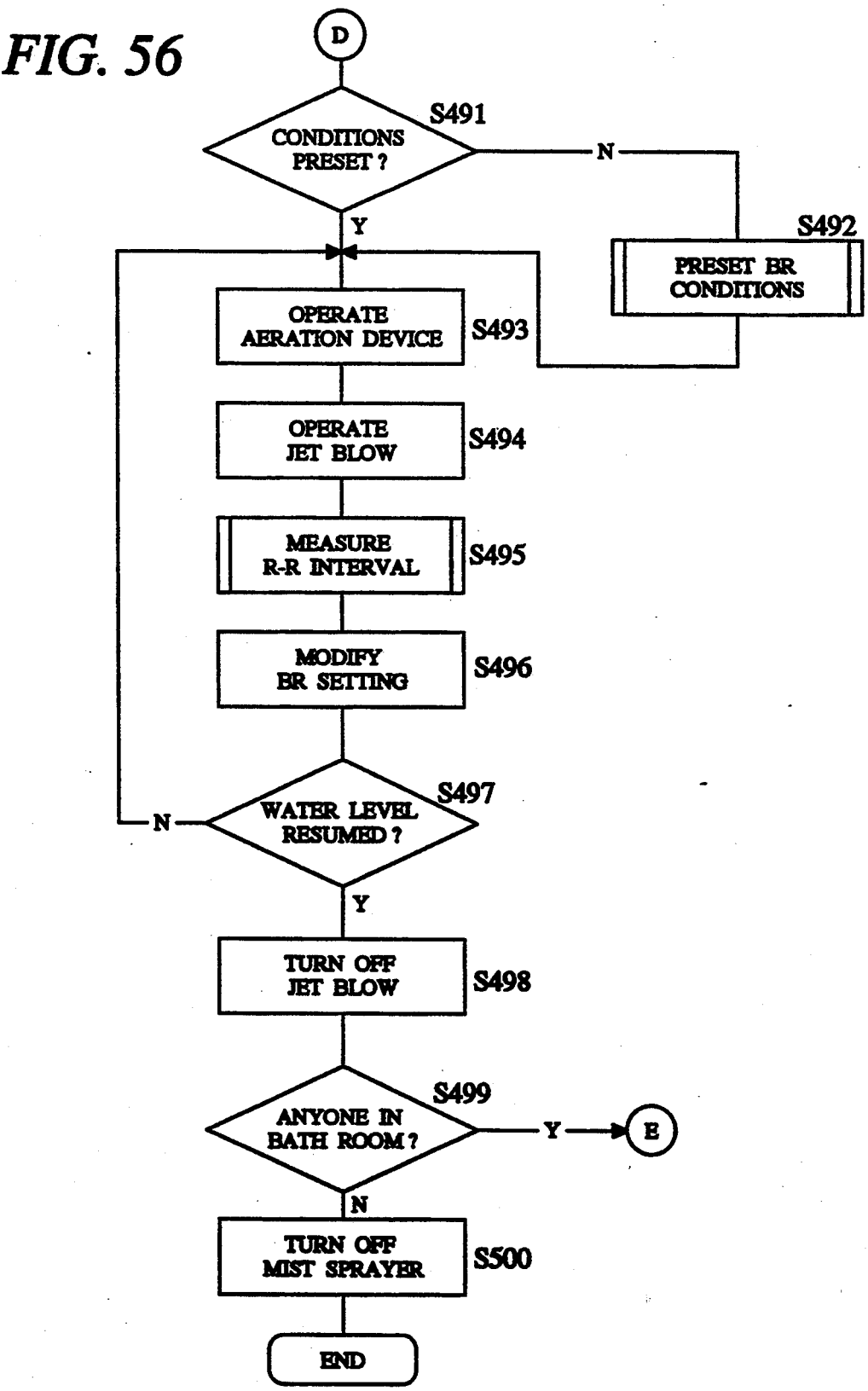
Figure 57:
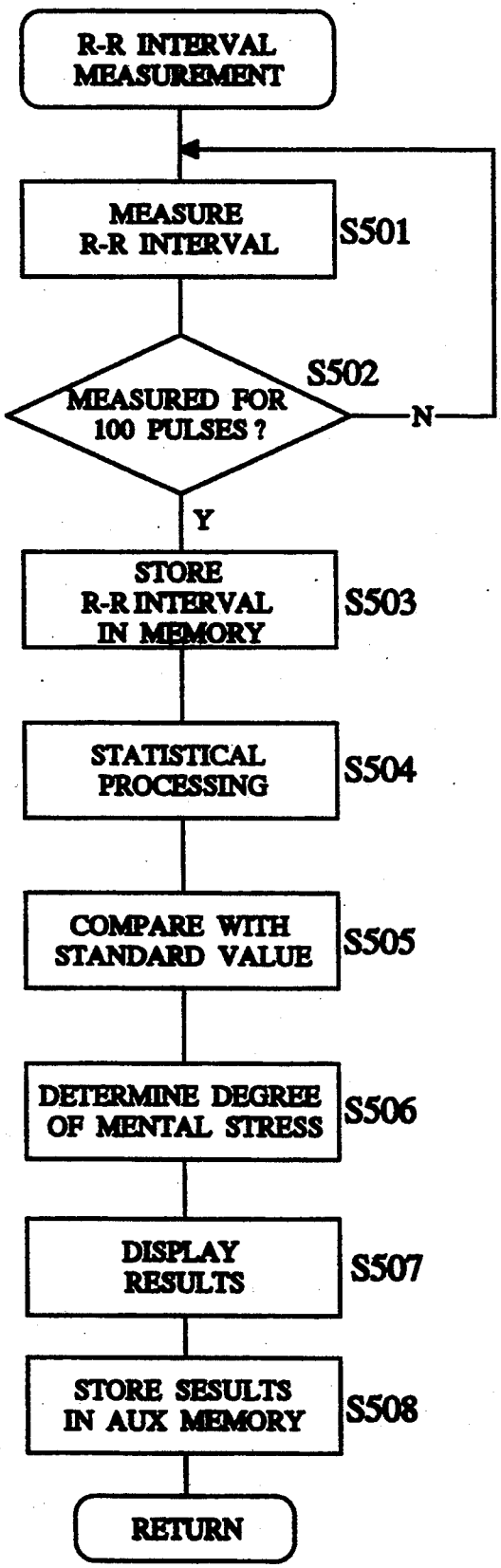

The hardware structure of the bath system 14 is also similar to that described before with reference to FIGS. 28 and 29 in connection with the centralized network configuration. FIGS. 55 and 56 illustrate the function of the microcomputer 45 of the bath system 14. As shown therein, the microcomputer 45 of the bath system 14 similarly monitors if a request-to-send is transmitted from the other appliances (S471). If the request is delivered from other appliance, the particular appliance is recognized based on the appliances ID number (S472) and the particular individual is identified based on the individuals ID number (S473). Then the table of FIG. 3 is looked up (S474) and the information required for the other appliance is transmitted thereto (S475). Accordingly, the other appliance will receive from the bath system 14 the data required for its own function. Sequence of events S476–500 for measuring and control functions following detection of the body weight is performed generally similar to the sequence S224–244 described before with reference to FIGS. 30 and 31, with presetting of the bath room conditions S478 being effected similar to the flowchart of FIG. 32, and with measurement of displacement similar to the flowchart shown in FIG. 33. With regard to measurement of the R—R interval of electrocardiogram (S495), however, in contrast to the centralized network system wherein the acquired data is transferred to the controller 20 (S278 of FIG. 34), the data acquired in the distributed network configuration is stored in the auxiliary memory for the microcomputer 45 of the bath system 14 as shown at S508 of FIG. 57.

Similarly, the hardware structure of the ergometer 15 is identical to that described with reference to FIGS. 37 and 38. Referring to the flowchart of FIG. 58 wherein operation of the microcomputer 48 of the ergometer 15 is shown, a request-to-send from the other appliances is periodically checked (S511). Upon detection of the request from other appliance, the particular appliance is recognized based on the appliances ID number (S512), the particular individual identified (S513), the table of FIG. 3 looked up (S514), and the information necessary for the other appliance transmitted (S515) to permit the other appliance to receive from the ergometer 15 the data required for its own function. Sequence of events from the body weight detection (S516) to the indication of expiration of exercise time (S527) is carried out in a manner similar to the sequence S281–292 described with reference to FIG. 41. In the distributed network arrangement, the microcomputer 48 of the ergometer 15 thereafter stores the amount of exercise and the pulse rate in the auxiliary memory thereof (S528), causes the final data displayed (S529) and terminates the routine.

Figure 59:
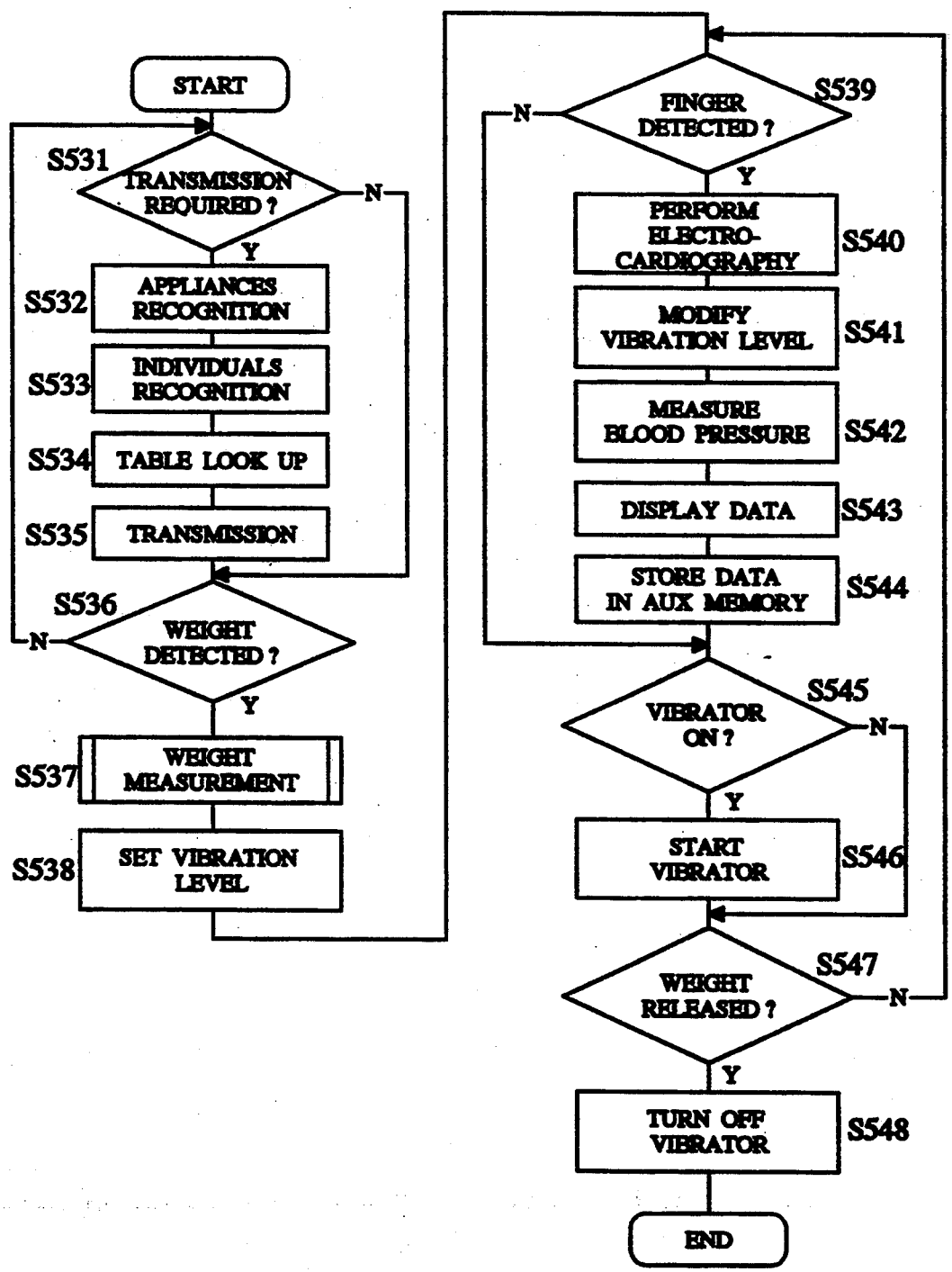

The hardware of the easy chair 16 is also similar to that described with reference to FIG. 42 in connection with the centralized network configuration. As shown in FIG. 59, the microcomputer 55 of the easy chair 16 similarly performs monitoring of request-to-send from the other appliances (S531), appliance recognition (S532), individual recognition (S533), table look-up (S534) and data transmission (S535). Sequence of events from body weight detection (S536) to deenergization of vibration (S548) is the same as the sequence S301–313 of FIG. 43, except that the derived data is stored in the memory of the microcomputer 55 associated with the easy chair 16.

The hardware and operation of the menu processor 17, the telephone 18 and the monitor 19 are the same as those of the centralized network.

Referring next to various flowcharts, the manner in which data communication is carried out between different household appliances in the distributed network system will be described, by way of an example, in conjunction with the ergometer 15 accessing via the network the toilet system 12 to acquire the vital information, such as the body fat content, detected and held by the toilet system 12.

Figure 58:
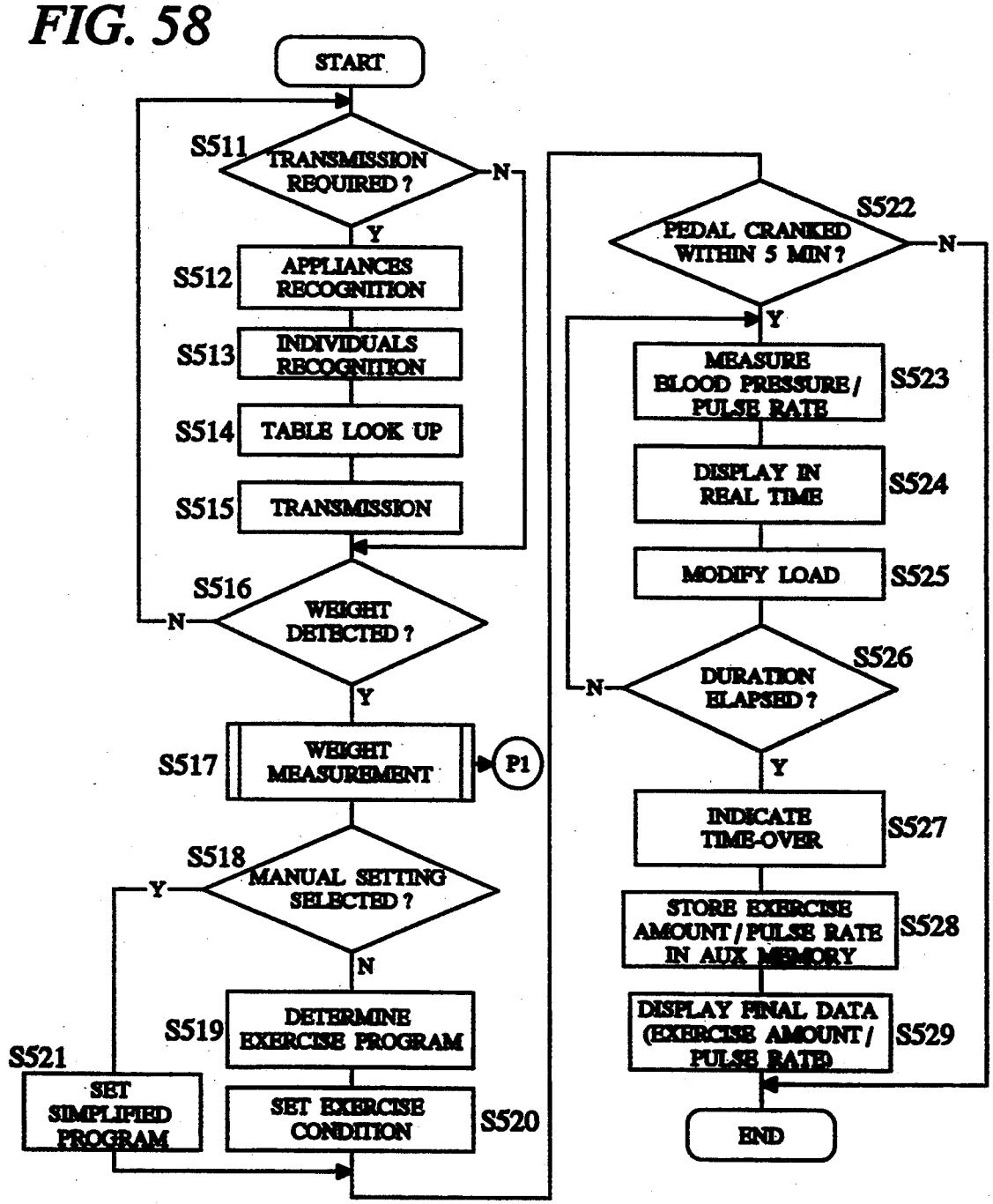

To start with the flowchart of FIG. 58, upon sensing the weight of the user (S516), the microcomputer 48 of the ergometer 15 performs the bodyweight measurement (S517). As indicated by the connector index P1 in FIGS. 58 and 21, this is done by the microcomputer 48 performing the routine shown in FIG. 21. As the routine proceeds to point S155, a transmission commence command is delivered to the IFU of the ergometer 15. As indicated by the index P2, this triggers the IFU of the ergometer 15 to perform the transmission routine S401–405 of FIG. 50 whereby the value of the bodyweight is transmitted onto the coaxial cable 11. As indicated by the index P3 in FIG. 50, the IFU of the toilet system 12 responds to the transmission from the IFU of the ergometer 15 to perform the data reception routine S401 and S406–411 shown in FIG. 50. As the reception routine of the IFU of the toilet system 12 is completed at S411, the microcomputer of the toilet system 12 proceeds to the sequence S421–425 of FIG. 52 as indicated by the index P4. At point S425, the IFU of the toilet system 12 performs the transmission routine S401–405 of FIG. 50 as indicated by the index P5. In response to the data transmission by the IFU of the toilet system 12, the IFU of the ergometer 15 conducts the data reception routine S401 and S406–411 of FIG. 50 as indicated by the index P6. As shown by the index P7 in FIGS. 50 and 21, the microcomputer of the ergometer 15 stores in the memory thereof the data transmitted from the toilet system 12 (S157). In this manner, the ergometer 15 accesses the toilet system 12 through the network to retrieve therefrom the vital information which is then used to control of the conditions of exercise.

In the foregoing description, data communication between the ergometer 15 and the toilet system 12 has been set out by way of example. It will be apparent that data communication between the other household appliances in the distributed network system is also carried out in a similar manner. Therefore, description thereof will not be necessary.

While the present invention has been described herein with reference to the specific embodiments thereof, it is contemplated that the present invention is not limited thereby and various changes and modification may be made therein for those skilled in the art within the spirit of the invention.

We claim:

1. A passive vital information monitoring system comprising:
    a data communication medium arranged in a building;
    first measuring means, connected to a household appliance used in routine physiological activities of individuals in said building, for detecting at least one physical characteristic of an individual in response to the use of said household appliance by said individual and for deriving a first data for recognizing said individual;

second measuring means connected to said household appliance for detecting at least one physiological characteristic of said individual in response to the use of said household appliance by said individual and deriving a second data indicative of the health condition of said individual;

a first communications interface unit connecting said first and second measuring means with said data communication medium for transmitting said first and second data from said first and second measuring means onto said data communication medium;

data controller means having a data storage memory; and, a second communications interface unit connecting said data controller means with said data communication medium for transmitting to said data controller means said first and second data transmitted from said first communications interface unit onto said data communication medium;

said first and second measuring means deriving, respectively, said first and second data passively in response to the use of said household appliance by said individual to cause said first and second data to be transmitted onto said data communication medium;

said memory of said data controller means structured for preliminarily storing said first data with respect to each of a plurality of predetermined individuals;

said data controller means recognizing a particular individual based on said first data transmitted onto said data communication medium and causing said second data transmitted onto said data communication medium to be stored in said memory in relation to said particular individual.

2. A passive vital information monitoring system according to claim 1, wherein said household appliance comprises a water closet system and wherein said second measuring means operates for ferforming urinalysis in connection with the use by said individual of said water closet system to derive said second data.

3. A passive vital information monitoring system according to claim 1, wherein said household appliance comprises a water closet system and wherein said second measuring means is designed to perform electrocardiography in connection with the use by said individual of said water closet system to derive said second data.

4. A passive vital information monitoring system according to claim 1, wherein said household appliance comprises a water closet system and wherein said second measuring means operates for detecting the body fat content of said individual in connection with the use by said individual of said water closet system to derive said second data.

5. A passive vital information monitoring system according to claim 1, wherein said household appliance comprises a water closet system and wherein said first measuring means operates for detecting the body weight of said individual in connection with the use by said individual of said water closet system to derive said first data.

6. A passive vital information monitoring system according to claim 1, wherein said household appliance comprises a bed system and wherein said second measuring means operates for detecting the body temperature of said individual in connection with the use by said individual of said bed system to derive said second data.

7. A passive vital information monitoring system according to claim 1, wherein said household appliance comprises a bed system and wherein said first measuring means operates for detecting the temperature distribution on said bed system in connection with the use by said individual of said bed system to derive said first data representing the stature of said individual.

8. A passive vital information monitoring system according to claim 1, wherein said household appliance comprises a bath system and wherein said second measuring means operates for detecting the R—R interval of electrocardiogram in connection with the use by said individual of said bath system to derive said second data.

9. A passive vital information monitoring system according to claim 1, wherein said household appliance comprises a bath system and wherein said first measuring means operates for detecting the volumetric displacement of said individual in connection with the use by said individual of said bath system to derive said first data.

10. A passive vital information monitoring system according to claim 1, wherein said household appliance comprises an indoor exercise device usable for health maintenance of said individual and wherein said second measuring means operates for detecting the amount of exercise in connection with the use by said individual of said device to derive said second data.

11. A passive vital information system according to claim 1, wherein said household appliance comprises an easy chair and wherein said second measuring means operates for performing electrocardiography in connection with the use by said individual of said easy chair to derive said second data.

12. A passive vital information monitoring system according to claim 1, further comprising a video monitor connected to said data communication medium for processing said second data stored in said memory and displaying processed data.

13. A passive vital information monitoring system comprising:

a data communication medium disposed in a building;

first measuring means, connected to a household appliance used in routine physiological activities of individuals in said building, for detecting at least one physical characteristic of an individual in response to the use of said household appliance by said individual and deriving a first data for recognizing said individual;

second measuring means connected to said household appliance for detecting at least one physiological characteristic of said individual in response to the use of said household appliance by said individual;

a first communications interface unit connecting said first and second measuring means with said data communication medium to permit data communication between said first and second measuring means and said data communication medium;

data controller means having a data storage memory; and, a second communications interface unit connecting said data controller means with said data communication medium to permit data communication between said data controller means and said data communication medium;

said memory of said data controller means being preliminarily installed with said first data and a second data representing another physical characteristic of individual with respect to each of a plurality of predetermined individuals;

said first measuring means operating for deriving said first data passively in response to the use of said household appliance by said individual and for causing said first data to be transmitted onto said data communication medium;

said data controller means recognizing a particular individual using said household appliance based on said first data transmitted onto said data communication medium and causing said second data of said particular individual as installed in said memory to be transmitted onto said data communication medium;

said second measuring means operating for detecting said at least one physiological characteristic of said particular individual passively in response to said use of said household appliance and for deriving a third data indicative of the health condition of said particular individual by making use of said second data on said particular individual transmitted onto said data communication medium.

14. A passive vital information monitoring system according to claim 13, wherein said household appliance comprises a water closet system, said first measuring means being associated with said water closet system for passively detecting the body weight of said particular individual in response to the use by said individual of said water closet system to cause said first data as representing the detected body weight to be transmitted onto said data communication medium, said second data including at least one of the stature and the sexuality of said predetermined individuals, said data controller means operating for recognizing said particular individual based on said body weight data transmitted onto said data communication medium and for causing said second data on said particular individual to be transmitted onto said data communication medium, said second measuring means comprising means for passively detecting the body fat content of said individual in response to the use of said water closet system, said means for detecting the body fat content deriving said third data as representing the body fat content of said particular individual by making use of said second data including at least one of the stature and the sexuality.

15. A passive vital information monitoring system according to claim 13, wherein said second measuring means further operates for causing said third data to be transmitted onto said medium and wherein said data controller means further operates for causing said third data transmitted onto said medium to be stored in said memory in connection with said particular individual.

16. A passive system for monitoring vital information on individuals comprising:

a data communication medium arranged in a building;

detection means, connected to a household appliance usable in routine physiological activities of the individuals in said building, for detecting at least one physical characteristic and at least one physiological characteristic of an individual in response to the use of said household appliance by said individual for deriving a first data useful in recognizing said individual and a second data representing the health condition of said individual;

a first communications interface unit connecting said detection means with said data communication medium for transmitting said first and second data from said detection means onto said data communication medium;

data controller means having a data storage memory; and a second communications interface unit connecting said data controller means with said data communication medium for transmitting to said data controller means said first and second data transmitted from said first communications interface unit onto said data communication medium;

said detection means deriving said first and second data passively in response to the use of said household appliance by said individual and causing said first and second data to be transmitted onto said data communication medium;

said memory of said data controller means structured for preliminarily storing said first data with respect to each of a plurality of predetermined individuals;

said data controller means recognizing a particular individual using said household appliance based on said first data transmitted onto said data communication medium and causing said second data transmitted onto said data communication medium to be stored in said memory in connection with said particular individual.

17. A passive system according to claim 16, wherein said household appliance comprises a bed system and wherein said detection means operates for detecting the temperature distribution on said bed system in connection with the use by said individual of said bed system to derive said first data representing the stature of said individual and said second data representing the body temperature of said individual.

18. A networked health care and monitoring system comprising:

a data communication medium arranged in a building;

a first household appliance disposed in said building for use in routine physiological activities of individuals;

measuring means connected to said first household appliance for detecting at least one physiological characteristic of an individual in response to the use by said individual of said first household appliance for deriving data indicative of the health condition of said individual;

a first communications interface unit connecting said measuring means with said data communication medium for transmitting said data onto said data communication medium;

a second household appliance disposed in said building for use in health maintenance activities of individuals;

control means for controlling said second household appliance;

a second communications interface unit connecting said control means with said data communication medium for controlling data communication between said control means and said data communication medium;

data controller means having a data storage memory; and a third communications interface unit connecting said data controller means with said data communication medium for controlling data communication between said data controller means and said data communication medium;

said measuring means deriving said data indicative of the health condition of said individual passively in response to the use by said individual of said first household appliance to cause said data to be transmitted onto said data communication medium;

said data controller means storing in said memory said data transmitted from said measuring means onto said data communication medium and transmitting said data onto said data communication medium in response to the use by said individual of said second household appliance;

said control means controlling said second household appliance based on said data transmitted from said data controller means onto said data communication medium.

19. A networked health care and monitoring system according to claim 18, wherein said second household appliance is a bath system provided with a massaging function and wherein said control means controls the degree of massaging effect of said second household appliance based on said data indicative of the health condition of said individual.

20. A networked health care and monitoring system according to claim 18, wherein said second household appliance is a bath system having a bath temperature control function and wherein said control means controls the bath temperature based on said data indicative of the health condition of said individual.

21. A networked health care and monitoring system according to claim 18, wherein said second household appliance is an indoor exercise device usable for health maintenance of said individual and wherein said control means controls the condition of exercise with said device based on said data indicative of the health condition of said individual.

22. A networked health care and monitoring system according to claim 18, wherein said second household appliance is an easy chair providing with a massaging function and wherein said control means controls the degree of massaging effect of said second household appliance based on said data indicative of the health condition of said individual.

23. A networked health care and monitoring system according to claim 18, wherein said second household appliance comprises data processing means for presenting alimentary menu based on said data indicative of the health condition of said individual.

24. A networked health care and monitoring system according to claim 18, wherein said first household appliance is a water closet system and wherein said measuring means performs urinalysis in response to the use by said individual of said water closet system to derive said data indicative of the health condition of said individual.

25. A networked health care and monitoring system according to claim 18, wherein said first household appliance is a water closet system and wherein said measuring means performs electrocardiography in response to the use by said individual of said water closet system to derive said data indicative of the health condition of said individual.

26. A networked health care and monitoring system according to claim 18, wherein said first household appliance is a water closet system and wherein said measuring means detects the body fat content of said individual in response to the use by said individual of said water closet system to derive said data.

27. A networked health care and monitoring system according to claim 18, wherein said first household appliance is a bed system and wherein said measuring means detects the body temperature of said individual in response to the use by said individual of said bed system to derive said data.

28. A networked health care and monitoring system comprising:

a data communication medium arranged in a building;

a first household appliance disposed in said building for use in routine physiological activities of individuals;

first measuring means connected to said first household appliance for detecting at least one physical characteristic of an individual in response to the use by said individual of said first household appliance for deriving a first data useful in recognizing said individual;

second measuring means connected to said first household appliance for detecting at least one physiological characteristic of said individual in response to the use by said individual of said first household appliance for deriving a second data indicative of the health condition of said individual;

a first communications interface unit connecting said first and second measuring means with said data communication medium for transmitting said first and second data from said first and second measuring means onto said data communication medium;

a second household appliance disposed in said building for use in health maintenance activities of individuals;

third measuring means connected to said second household appliance for detecting at least one physical characteristic of an individual in response to the use by said individual of said second household appliance for deriving a third data useful in recognizing said individual;

control means for controlling said second household appliance;

a second communications interface unit connecting said third measuring means and said control means with said data communication medium for controlling data communication between said third measuring means and control means, in the first place, and said data communication medium, in the second place;

data controller means having a data storage memory; and a third communications interface unit connecting said data controller means with said data communication medium for controlling data communication between said data controller means and said data communication medium;

said first and second measuring means operating, respectively, for deriving said first and second data passively in response to the use by an individual of said first household appliance for causing said first and second data to be transmitted onto said data communication medium;

said data controller means recognizing a particular individual using said first household appliance based on said first data transmitted onto said data communication medium and storing in said memory said second data in connection with said particular individual;

said third measuring means deriving said third data in response to the use by an individual of said second household appliance for causing said third data to be transmitted onto said data communication medium;

said data controller means being responsive to said third data as transmitted from said third measuring means onto said data communication medium for recognizing a particular individual using said second household appliance and for causing said second data representing the health condition of said particular individual using said second household appliance to be retrieved from said memory and transmitted onto said data communication medium;

said control means of said second household appliance controlling said second household appliance based on said second data transmitted from said data controller means onto said data communication medium.

29. A networked health care system comprising:
a data communication medium arranged in a building;
a household appliance disposed in said building for use in health care and maintenance activities of individuals;
measuring means connected to said household appliance for detecting at least one physical characteristic of an individual in response to the use by said individual of said household appliance for deriving a first data useful in recognizing said individual;
control means for controlling said household appliance;
a first communications interface unit connecting said measuring means and said control means with said data communication medium for controlling data communication between said measuring and control means and said data communication medium;
data controller means having a data storage memory wherein said first data and a second data representing the health condition of an individual are stored for each of a plurality of predetermined individuals; and,
a second communications interface unit connecting said data controller means with said data communication medium for controlling data communication between said data controller means and said data communication medium;
said measuring means passively deriving said first data in response to the use by an individual of said household appliance for causing said first data to be transmitted onto said data communication medium;
said data controller means being responsive to transmission of said first data onto said data communication medium for recognizing a particular individual corresponding to said first data and for causing said second data representing the health condition of said particular individual to be transmitted onto said data communication medium;
said control means controlling said household appliance based on said second data transmitted onto said data communication medium.

30. A networked health care and monitoring system comprising:
a data communication medium arranged in a building;
a first household appliance disposed in said building for use in routine physiological activities of individuals;
measuring means, including a data storage memory, connected to said first household appliance for detecting at least one physiological characteristic of an individual in response to the use by said individual of said first household appliance to derive data indicative of the health condition of said individual;
a first communications interface unit connecting said measuring means with said data communication medium for transmitting said data onto said data communication medium;
a second household appliance disposed in said building for use in health maintenance activities of individuals;
control means for controlling said second household appliance; and,
a second communications interface unit connecting said control means with said data communication medium for controlling data communication between said control means and said data communication medium;
said measuring means deriving said data indicative of the health condition of said individual in response to the use by said individual of said first household appliance to cause said data to be stored in said memory;
said control means causing said measuring means to transmit onto said data communication medium said data stored in said memory thereof in response to the use by said individual of said second household appliance;
said control means controlling said second household appliance based on said data transmitted onto said data communication medium.

31. A networked health care and monitoring system according to claim 30, wherein said measuring means operates for passively deriving said data indicative of the health condition of said individual in response to the use by said individual of said first household appliance.

32. A networked health care and monitoring system according to claim 30, wherein said first household appliance comprises a water closet system and wherein said measuring means operates for performing urinalysis in connection with the use by said individual of said water closet system to derive said data indicative of the health condition of said individual.

33. A networked health care and monitoring system according to claim 30, wherein said first household appliance comprises a water closet system and wherein said measuring means operates for performing electrocardiography in connection with the use by said individual of said water closet system to derive said data indicative of the health condition of said individual.

34. A networked health care and monitoring system according to claim 30, wherein said first household appliance comprises a water closet system and wherein said measuring means operates for detecting the body fat content of said individual in connection with the use by said individual of said water closet system to derive said data indicative of the health condition of said individual.

35. A networked health care and monitoring system according to claim 30, wherein said first household appliance comprises a water closet system and wherein said measuring means operates for detecting the artery blood pressure of said individual in connection with the use by said individual of said water closet system to derive said data indicative of the health condition of said individual.

36. A networked health care and monitoring system according to claim 30, wherein said first household appliance comprises a bed system and wherein said measuring means operates for detecting the body temperature of said individual in connection with the use by said individual of said bed system to derive said data indicative of the health condition of said individual.

37. A networked health care and monitoring system according to claim 30, wherein said first household appliance comprises a bath system and wherein said measuring means operates for detecting the R—R interval of electrocardiogram of said individual in connection with the use by said individual of said bath system to derive said data indicative of the health condition of said individual.

38. A networked health care and monitoring system according to claim 30, wherein said first household appliance comprises an easy chair and wherein said measuring means operates for performing electrocardiography in connection with the use by said individual of said easy chair to derive said data indicate of the health condition of said individual.

39. A networked health care and monitoring system according to claim 30, wherein said second household appliance comprises a bath system provided with a massaging function and wherein said control means operates for controlling the degree of massaging effect of said second household appliance based on said data indicative of the health condition of said individual.

40. A networked health care and monitoring system according to claim 30, wherein said second household appliance comprises a bath system provided with a bath temperature control function and wherein said control means operates for controlling the bath temperature based on said data indicative of the health condition of said individual.

41. A networked health care and monitoring system according to claim 30, wherein said second household appliance comprises an indoor exercise device usable for health maintenance of said individual and wherein said control means operates for controlling the condition of exercise with said device based on said data indicative of the health condition of said individual.

42. A networked health care and monitoring system according to claim 30, wherein said second household appliance comprises an easy chair provided with a massaging function and wherein said control means operates for controlling the degree of massaging effect of said second household appliance based on said data indicative of the health condition of said individual.

43. A networked health care and monitoring system according to claim 30, wherein said second household appliance comprises data processing means for presenting alimentary menu based on said data indicative of the health condition of said individual.

44. A networked health care and monitoring system of the distributed network configuration comprising:
a data communication medium arranged in a building;
a first household appliance disposed in said building for use in routine physiological activities of individuals;
first measuring means connected to said first household appliance for detecting at least one physical characteristic of an individual in response to the use by said individual of said first household appliance for deriving a first data useful in recognizing said individual;
second measuring means, including a data storage memory, connected to said first household appliance for detecting at least one physiological characteristic of said individual in response to the use by said individual of said first household appliance for deriving a second data indicative of the health condition of said individual;
a first communications interface unit connecting said first and second measuring means with said data communication medium for permitting data communication between said first and second measuring means and said data communication medium;
a second household appliance disposed in said building for use in health maintenance activities of individuals;
third measuring means connected to said second household appliance for detecting at least one physical characteristic of an individual in response to the use by said individual of said second household appliance for deriving a third data useful in recognizing said individual;
control means for controlling said second household appliance; and,
a second communications interface unit connecting said third measuring means and said second control means with said data communication medium for permitting data communication between said third measuring means and said control means, in the first place, and said data communication medium, in the second place;
said first and second measuring means deriving said first and second data, respectively, passively each time said first household appliance is used by an individual for causing said second data to be stored in said data storage memory thereby to provide a storage of said second data for a plurality of individuals;
said third measuring means deriving said third data in response to the use by an individual of said second household appliance for causing said third data to be transmitted onto said data communication medium;
said second measuring means being responsive to said third data as transmitted from said third measuring means onto said data communication medium for recognizing a particular individual using said second household appliance and for causing said second data representing the health condition of said particular individual using said second household appliance to be retrieved from said storage memory and transmitted onto said data communication medium;
said control means of said second household appliance controlling said second household appliance based on said second data transmitted from said second measuring means onto said data communication medium.

45. A networked health care and monitoring system of the distributed network configuration comprising:
a data communication medium arranged in a building;
a first household appliance disposed in said building for use in routine physiological activities of individuals;
first measuring means, including a data storage memory, connected to said first household appliance for detecting at least one physical characteristic and at least one physiological characteristic of an individual in response to the use by said individual of said first household appliance for deriving a first data useful in recognizing said individual and a second data indicative of the health condition of said individual;

a first communications interface unit connecting said first measuring means with said data communication medium for permitting data communication between said first measuring means and said data communication medium;

a second household appliance disposed in said building for use in health maintenance activities of individuals;

second measuring means connected to said second household appliance for detecting at least one physical characteristic of an individual in response to the use by said individual of said second household appliance for deriving third data useful in recognizing said individual;

control means for controlling said second household appliance; and, a second communications interface unit connecting said second measuring means and said control means with said data communication medium for permitting data communication of said second measuring means and said control means with said data communication medium;

said first measuring means deriving said first and second data passively each time said first household appliance is used by an individual to cause said second data to be stored in said data storage memory thereby to provide a storage of said second data for a plurality of individuals;

said second measuring means deriving said third data in response to the use by an individual of said second household appliance for causing said third data to be transmitted onto said data communication medium;

said first measuring means being responsive to said third data as transmitted from said second measuring means onto said data communication medium for recognizing a particular individual using said second household appliance and for causing said second data representing the health condition of said particular individual using said second household appliance to be retrieved from said storage memory and transmitted onto said data communication medium;

said control means of said second household appliance controlling said second household appliance based on said second data transmitted from said first measuring means onto said data communication medium.

* * * * *